(12) United States Patent
Barbas, III et al.

(10) Patent No.: US 6,955,900 B1
(45) Date of Patent: Oct. 18, 2005

(54) METHODS FOR PRODUCING POLYPEPTIDE BINDING SITES, MONOCLONAL ANTIBODIES AND COMPOSITIONS THEREOF

(75) Inventors: Carlos F. Barbas, III, San Diego, CA (US); Richard A. Lerner, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 08/495,606

(22) PCT Filed: Feb. 2, 1994

(86) PCT No.: PCT/US94/01258

§ 371 (c)(1),
(2), (4) Date: Aug. 21, 1995

(87) PCT Pub. No.: WO94/18221

PCT Pub. Date: Aug. 18, 1994

Related U.S. Application Data

(63) Continuation-in-part of application No. 08/084,542, filed on Jun. 28, 1993, now abandoned, which is a continuation-in-part of application No. 08/012,566, filed on Feb. 2, 1993, now abandoned.

(51) Int. Cl.[7] .......................... C12N 15/09; C12P 21/00
(52) U.S. Cl. ..................... 435/69.7; 435/69.6; 435/69.1
(58) Field of Search ............................ 536/23.4, 23.53; 424/133.1, 143.1, 152.1, 141.1; 435/69.1, 69.6, 69.7

(56) References Cited

U.S. PATENT DOCUMENTS

| | | | |
|---|---|---|---|
| 5,223,409 A | | 6/1993 | Ladner et al. |
| 5,403,484 A | | 4/1995 | Ladner |
| 5,652,110 A | * | 7/1997 | Kim et al. |
| 5,667,988 A | * | 9/1997 | Barbas et al. ............... 435/69.1 |

FOREIGN PATENT DOCUMENTS

| | | | |
|---|---|---|---|
| EP | 404003 | | 12/1990 |
| WO | WO88/06630 | | 9/1988 |
| WO | WO90/14424 | | 11/1990 |
| WO | 91/0996 | * | 7/1991 |
| WO | WO91/17271 | | 11/1991 |
| WO | WO91/18980 | | 12/1991 |
| WO | WO91/19818 | | 12/1991 |
| WO | WO92/01047 | | 1/1992 |
| WO | WO92/06204 | | 4/1992 |
| WO | WO92/07077 | | 4/1992 |

OTHER PUBLICATIONS

Rudikoff et al. PNAS 79: 1979–1983, 1982.*
Erlich, H. A PCR Technology. Stockton Press 1989, Se pp. 80–82.*
Parka et al. PNAS 85: 3080–3084, 1988.*
Barbas et al. PNAS 90: 1000–10007, Nov. 1993.*
Gram et al. PNAS 89: 3572, 1990.*
Kalyanaraman, et al., "Evidence by Peptide Mapping that the Region CD4(81–92) is Involved in gp120/CD4 Interaction Leading to HIV Infection and HIV–Induced Syncytium Formation", *J. Immunol.*, 145:4072–8 (1990).
Taub, et al., "A Monoclonal Antibody Against the Platelet Fibrinogen Receptor Contains a Sequence that Minics a Receptor Recognition Domain in Fibrinogen", *J. Biol. Chem.*, 264: 259–265 (1989).
Billetta, et al, "Immunogenicity of an Engineered Internal Image Antibody", *Proc. Natl. Acad. Sci., USA*, 88: 4713–4717 (1991).
Sollazzo, et al., "Expression of an Exogenous Peptide Epitope Genetically Engineered in the Variable Domain Of an Immunoglobulin: Implications for Antibody and Peptide Folding", *Protein Engineering*, 4:215–220 (1990).
Marks, et al., "Human Antibodies from V–gene Libraries Displayed on Phage", *J. Mol. Bio.*, 222:581–597 (1991).
Barbas, et al., "Assembly of Combinatorial Antibody Libraries on Phage Surfaces: The Gene III Site", *Proc. Natl. Acad. Sci., USA*, 88: 7978–7982 (1991).
Barbas, et al., "Semisynthetic Combinatorial Antibody Libraries: A Chemical Solution to the Diversity Problem", *Proc. Natl. Acad. Sci., USA*, 89: 4457–4461 (1992).
Cwirla, et al., "Peptides on Phage: A Vast Library of Peptides for Identifying Ligands", *Proc. Natl. Acad. Sci., USA*, 87: 6378–6382 (1992).
Devlin, et al., "Random Peptide Libraries: A Source of Specific Protein Binding Molecules", *Science*, 249: 404–406 (1990).
Kang, et al., "Linkage of Recognition and Replication Fundtions by Assembling Combinatorial Antibody Fab Libraries Along Phage Surfaces", *Proc. Natl. Acad. Sci., USA*, 88: 4363–4366 (1991).
Kang, et al., "Antibody Redesign by Chain Shuffling from Random Combinatorial Immunoglubin Libraries", *Proc. Natl. Acad. Sci., USA*, 88: 11120–11123 (1991).
O'Neil, et al., "Design of DNA–Binding Peptides Based on the Leucine Zipper Motif", *Science*, 249: 744–778 (1990).
Roberts, et al., "Protease Inhibitor Display M13 Phage: Selection of High–Affinity Neutrophil Elastase Inhibitors", *Gene*, 121: 9–15 (1992).
Roberts, et al., "Directed Evolution of a Protein: Selection of Potent Neutrophil Elastase Inhibitors Displayed on M13 Fusion Phage", *Proc. Natl. Acad. Sci., USA*, 89: 2429–2433 (1992).

(Continued)

*Primary Examiner*—Ronald B. Schwadron
(74) *Attorney, Agent, or Firm*—Thomas Fitting; Michael J. McCarthy

(57) ABSTRACT

The present invention describes methods for producing binding sites on polypeptides, and particularly for producing binding sites within the CDR regions of immunoglobulin heavy or light chains that are displayed on the surface of filamentous phage particles. The invention also describes oligonucleotides useful for preparing the binding sites, and human monoclonal antibodies produced by the present methods.

3 Claims, 5 Drawing Sheets

OTHER PUBLICATIONS

Scott and Smith, "Searching for Peptide Ligands with an Epitope Library", *Science*, 249: 386–390 (1990).

Barbas, Carlos F. and Lerner, Richard A., "Combinatorial Immunoglobulin Libraries on the Surface of Phage (Phabs): Rapid Selection of Antigen–Specific Fabs" *Methods: A Companion to Meth. in Enzym.*, 2:119–124 (1991).

Burton, et al., "A Large Array of Human Monoclonal Antibodies to Type I Human Immunodeficiency Virus From Combinatorial Libraries of Asymptomatic Seropositive Individuals" *Proc. Natl. Acad. Sci., USA*, 88:10134–10137 (1991).

Gram, et al., "In Vitro Selection and Affinity Maturation of Antibodies From a Naive Combinatorial Immunoglobulin Library" *Proc. Natl. Acad. Sci., USA*, 89:3576–3580 (1992).

Parmley, Stephen F. and Smith, George P., "Antibody–Selectable Filamentous fd Phage Vectors: Affinity Purification of Target Genes" *Gene*, 73:305–318 (1988).

Ward, et al., "Binding Activities of a Repertoire of Single Immunoglobulin Variable Domains Secreted from *Escherichia coli*" *Nature*, 341:544–546 (1989).

Osband, et al., "Problems in the Investigational Study and Clinical Use of Cancer Immunotherapy", *Immunology Today*, 11: 193–195 (1990).

Harris, et al., "Therapeutic Antibodies—the Coming of Age", *TIBTECH* 11: 42–44 (1993).

* cited by examiner

SEQUENCE LISTING

<160> NUMBER OF SEQ ID NOS: 78

<210> SEQ ID NO 1
<211> LENGTH: 18
<212> TYPE: PRT
<213> ORGANISM: Artificial Sequence

```
<220> FEATURE:
<223> OTHER INFORMATION: synthesized

<400> SEQUENCE: 1

Val Gly Cys Gly Ala Leu Arg Gly Asp Pro Trp Cys Tyr Tyr Met
 1               5                  10                  15

Asp Val

<210> SEQ ID NO 2
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 10
<223> OTHER INFORMATION: Xaa = Any Amino Acid

<400> SEQUENCE: 2

Val Gly Tyr Gly Arg Leu Arg Gly Asp Xaa Pro Trp Cys Tyr Tyr Met
 1               5                  10                  15

Asp Val

<210> SEQ ID NO 3
<211> LENGTH: 18
<212> TYPE: PRT
<213> ORGANISM: Artificial Sequence
<220> FEATURE:
<223> OTHER INFORMATION: synthesized

<400> SEQUENCE: 3

Val Gly Cys Gly Arg Leu Arg Gly Asp Asp Pro Trp Cys Tyr Tyr Met
 1               5                  10                  15

Asp Val

<210> SEQ ID NO 4
<211> LENGTH: 18
<212> TYPE: PRT
<213> ORGANISM: Artificial Sequence
<220> FEATURE:
<223> OTHER INFORMATION: synthesized

<400> SEQUENCE: 4

Val Gly Cys Ser Phe Gly Arg Gly Asp Ile Arg Asn Cys Tyr Tyr Met
 1               5                  10                  15

Asp Val

<210> SEQ ID NO 5
<211> LENGTH: 18
<212> TYPE: PRT
<213> ORGANISM: Artificial Sequence
<220> FEATURE:
<223> OTHER INFORMATION: synthesized

<400> SEQUENCE: 5

Val Gly Cys Ser Phe Gly Arg Gly Asp Asp Arg Asn Phe Tyr Tyr Met
 1               5                  10                  15

Asp Val

<210> SEQ ID NO 6
<211> LENGTH: 18
<212> TYPE: PRT
<213> ORGANISM: Artificial Sequence
```

```
<220> FEATURE:
<223> OTHER INFORMATION: synthesized

<400> SEQUENCE: 6

Val Gly Cys Thr Gln Gly Arg Gly Asp Trp Arg Ser Cys Tyr Tyr Met
 1               5                  10                  15

Asp Val

<210> SEQ ID NO 7
<211> LENGTH: 18
<212> TYPE: PRT
<213> ORGANISM: Artificial Sequence
<220> FEATURE:
<223> OTHER INFORMATION: synthesized

<400> SEQUENCE: 7

Val Gly Cys Thr Tyr Gly Arg Gly Asp Thr Arg Asn Cys Tyr Tyr Met
 1               5                  10                  15

Asp Val

<210> SEQ ID NO 8
<211> LENGTH: 18
<212> TYPE: PRT
<213> ORGANISM: Artificial Sequence
<220> FEATURE:
<223> OTHER INFORMATION: synthesized

<400> SEQUENCE: 8

Val Gly Cys Pro Ile Pro Arg Gly Asp Trp Arg Glu Cys Tyr Tyr Met
 1               5                  10                  15

Asp Val

<210> SEQ ID NO 9
<211> LENGTH: 18
<212> TYPE: PRT
<213> ORGANISM: Artificial Sequence
<220> FEATURE:
<223> OTHER INFORMATION: synthesized

<400> SEQUENCE: 9

Val Gly Cys Thr Trp Gly Arg Gly Arg Glu Arg Asn Cys Tyr Tyr Met
 1               5                  10                  15

Asp Val

<210> SEQ ID NO 10
<211> LENGTH: 18
<212> TYPE: PRT
<213> ORGANISM: Artificial Sequence
<220> FEATURE:
<223> OTHER INFORMATION: synthesized

<400> SEQUENCE: 10

Val Gly Cys Asp Lys Arg Arg Gly Asp Arg Pro Arg Cys Tyr Tyr Met
 1               5                  10                  15

Asp Val

<210> SEQ ID NO 11
<211> LENGTH: 18
<212> TYPE: PRT
<213> ORGANISM: Artificial Sequence
<220> FEATURE:
<223> OTHER INFORMATION: synthesized

<400> SEQUENCE: 11
```

```
Val Gly Cys Ser Arg Arg Gly Asp Arg Pro Gln Cys Tyr Tyr Met
 1               5                  10                  15

Asp Val

<210> SEQ ID NO 12
<211> LENGTH: 11
<212> TYPE: PRT
<213> ORGANISM: Artificial Sequence
<220> FEATURE:
<223> OTHER INFORMATION: synthesized

<400> SEQUENCE: 12

Cys Ser Phe Gly Arg Gly Asp Ile Arg Asn Cys
 1               5                  10

<210> SEQ ID NO 13
<211> LENGTH: 18
<212> TYPE: PRT
<213> ORGANISM: Artificial Sequence
<220> FEATURE:
<223> OTHER INFORMATION: synthesized

<400> SEQUENCE: 13

Val Gly Cys Ser Phe Gly Arg Ala Asp Thr Arg Asn Cys Tyr Tyr Met
 1               5                  10                  15

Asp Val

<210> SEQ ID NO 14
<211> LENGTH: 18
<212> TYPE: PRT
<213> ORGANISM: Artificial Sequence
<220> FEATURE:
<223> OTHER INFORMATION: synthesized

<400> SEQUENCE: 14

Val Gly Cys Ser Gly Phe Arg Val Asp Asp Arg Asn Cys Tyr Tyr Met
 1               5                  10                  15

Asp Val

<210> SEQ ID NO 15
<211> LENGTH: 18
<212> TYPE: PRT
<213> ORGANISM: Artificial Sequence
<220> FEATURE:
<223> OTHER INFORMATION: synthesized

<400> SEQUENCE: 15

Val Gly Cys Ser Phe Gly Arg Gln Asp Ala Arg Asn Cys Tyr Tyr Met
 1               5                  10                  15

Asp Val

<210> SEQ ID NO 16
<211> LENGTH: 18
<212> TYPE: PRT
<213> ORGANISM: Artificial Sequence
<220> FEATURE:
<223> OTHER INFORMATION: synthesized

<400> SEQUENCE: 16

Val Gly Cys Ser Phe Gly Arg Ser Asp Val Arg Asn Cys Tyr Tyr Met
 1               5                  10                  15

Asp Val
```

<210> SEQ ID NO 17
<211> LENGTH: 18
<212> TYPE: PRT
<213> ORGANISM: Artificial Sequence
<220> FEATURE:
<223> OTHER INFORMATION: synthesized

<400> SEQUENCE: 17

Val Gly Cys Ser Phe Gly Arg Ala Asp Arg Arg Asn Cys Tyr Tyr Met
 1               5                  10                  15

Asp Val

<210> SEQ ID NO 18
<211> LENGTH: 18
<212> TYPE: PRT
<213> ORGANISM: Artificial Sequence
<220> FEATURE:
<223> OTHER INFORMATION: synthesized

<400> SEQUENCE: 18

Val Gly Cys Ser Phe Gly Arg Ser Asp Val Arg Asn Phe Tyr Tyr Met
 1               5                  10                  15

Asp Val

<210> SEQ ID NO 19
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 9
<223> OTHER INFORMATION: Xaa = Any Amino Acid

<400> SEQUENCE: 19

Val Gly Cys Ser Phe Gly Arg Thr Xaa Thr Arg Asn Cys Tyr Tyr Met
 1               5                  10                  15

Asp Val

<210> SEQ ID NO 20
<211> LENGTH: 18
<212> TYPE: PRT
<213> ORGANISM: Artificial Sequence
<220> FEATURE:
<223> OTHER INFORMATION: synthesized

<400> SEQUENCE: 20

Val Gly Cys Ser Phe Gly Arg Gln Asp Val Arg Asn Cys Tyr Tyr Met
 1               5                  10                  15

Asp Val

<210> SEQ ID NO 21
<211> LENGTH: 18
<212> TYPE: PRT
<213> ORGANISM: Artificial Sequence
<220> FEATURE:
<223> OTHER INFORMATION: synthesized

<400> SEQUENCE: 21

Val Gly Cys Ser Phe Gly Arg Asp Asp Gly Arg Asn Cys Tyr Tyr Met
 1               5                  10                  15

Asp Val

```
<210> SEQ ID NO 22
<211> LENGTH: 18
<212> TYPE: PRT
<213> ORGANISM: Artificial Sequence
<220> FEATURE:
<223> OTHER INFORMATION: synthesized

<400> SEQUENCE: 22

Val Gly Cys Ser Phe Gly Arg Trp Asp Ala Arg Asn Cys Tyr Tyr Met
 1               5                  10                  15

Asp Val

<210> SEQ ID NO 23
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 7
<223> OTHER INFORMATION: Xaa = Any Amino Acid

<400> SEQUENCE: 23

Val Gly Cys Ser Phe Gly Xaa Gly Asp Arg Arg Asn Cys Tyr Tyr Met
 1               5                  10                  15

Asp Val

<210> SEQ ID NO 24
<211> LENGTH: 18
<212> TYPE: PRT
<213> ORGANISM: Artificial Sequence
<220> FEATURE:
<223> OTHER INFORMATION: synthesized

<400> SEQUENCE: 24

Val Gly Cys Ser Phe Gly Lys Arg Asp Met Arg Asn Cys Tyr Tyr Met
 1               5                  10                  15

Asp Val

<210> SEQ ID NO 25
<211> LENGTH: 18
<212> TYPE: PRT
<213> ORGANISM: Artificial Sequence
<220> FEATURE:
<223> OTHER INFORMATION: synthesized

<400> SEQUENCE: 25

Val Gly Cys Ser Phe Gly Lys Gly Asp Asn Arg Asn Cys Tyr Tyr Met
 1               5                  10                  15

Asp Val

<210> SEQ ID NO 26
<211> LENGTH: 18
<212> TYPE: PRT
<213> ORGANISM: Artificial Sequence
<220> FEATURE:
<223> OTHER INFORMATION: synthesized

<400> SEQUENCE: 26

Val Gly Cys Ser Phe Gly Arg Thr Asp Gln Arg Asn Cys Tyr Tyr Met
 1               5                  10                  15

Asp Val
```

```
<210> SEQ ID NO 27
<211> LENGTH: 18
<212> TYPE: PRT
<213> ORGANISM: Artificial Sequence
<220> FEATURE:
<223> OTHER INFORMATION: synthesized

<400> SEQUENCE: 27

Gly Val Arg Arg Val Leu Gly Asn Gln Gly Ser Phe Leu Pro Gly Trp
 1               5                  10                  15

Asp Val

<210> SEQ ID NO 28
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 8
<223> OTHER INFORMATION: Xaa = Any Amino Acid

<400> SEQUENCE: 28

Val Gly Cys Ser Phe Gly Arg Xaa Asp Gly Arg Asn Phe Tyr Tyr Met
 1               5                  10                  15

Asp Val

<210> SEQ ID NO 29
<211> LENGTH: 18
<212> TYPE: PRT
<213> ORGANISM: Artificial Sequence
<220> FEATURE:
<223> OTHER INFORMATION: synthesized

<400> SEQUENCE: 29

Val Gly Cys Ser Phe Gly Arg Arg Asp Glu Arg Asn Cys Tyr Tyr Met
 1               5                  10                  15

Asp Val

<210> SEQ ID NO 30
<211> LENGTH: 18
<212> TYPE: PRT
<213> ORGANISM: Artificial Sequence
<220> FEATURE:
<223> OTHER INFORMATION: synthesized

<400> SEQUENCE: 30

Val Gly Cys Ser Phe Gly Arg Asn Asp Ala Arg Asn Cys Tyr Tyr Met
 1               5                  10                  15

Asp Val

<210> SEQ ID NO 31
<211> LENGTH: 18
<212> TYPE: PRT
<213> ORGANISM: Artificial Sequence
<220> FEATURE:
<223> OTHER INFORMATION: synthesized

<400> SEQUENCE: 31

Val Gly Cys Ser Phe Gly Arg Arg Asp Glu Arg Asp Cys Tyr Tyr Met
 1               5                  10                  15

Asp Val
```

```
<210> SEQ ID NO 32
<211> LENGTH: 18
<212> TYPE: PRT
<213> ORGANISM: Artificial Sequence
<220> FEATURE:
<223> OTHER INFORMATION: synthesized

<400> SEQUENCE: 32

Val Gly Cys Ser Phe Gly Arg Thr Asp Thr Arg Asn Cys Tyr Tyr Met
 1               5                  10                  15

Asp Val

<210> SEQ ID NO 33
<211> LENGTH: 18
<212> TYPE: PRT
<213> ORGANISM: Artificial Sequence
<220> FEATURE:
<223> OTHER INFORMATION: synthesized

<400> SEQUENCE: 33

Val Gly Cys Ser Phe Gly Arg Ala Asp Asn Arg Asn Cys Tyr Tyr Met
 1               5                  10                  15

Asp Val

<210> SEQ ID NO 34
<211> LENGTH: 18
<212> TYPE: PRT
<213> ORGANISM: Artificial Sequence
<220> FEATURE:
<223> OTHER INFORMATION: synthesized

<400> SEQUENCE: 34

Val Gly Cys Ser Phe Gly Arg Asn Asn Ser Arg Asn Cys Tyr Tyr Met
 1               5                  10                  15

Asp Val

<210> SEQ ID NO 35
<211> LENGTH: 7
<212> TYPE: PRT
<213> ORGANISM: Human immunodeficiency virus type 1

<400> SEQUENCE: 35

Gly Asn Gln Gly Ser Phe Leu
 1               5

<210> SEQ ID NO 36
<211> LENGTH: 8
<212> TYPE: PRT
<213> ORGANISM: Epstein Barr Virus

<400> SEQUENCE: 36

Glu Asp Pro Gly Phe Phe Asn Glu
 1               5

<210> SEQ ID NO 37
<211> LENGTH: 11
<212> TYPE: PRT
<213> ORGANISM: Epstein Barr Virus

<400> SEQUENCE: 37

Glu Asp Pro Gly Lys Gln Leu Tyr Asn Val Glu
 1               5                  10
```

```
<210> SEQ ID NO 38
<211> LENGTH: 17
<212> TYPE: PRT
<213> ORGANISM: Homo sapiens

<400> SEQUENCE: 38

Arg Leu Phe Phe Asn Tyr Leu Val Ile Phe Glu Met Val His Leu Lys
 1               5                  10                  15
Glu

<210> SEQ ID NO 39
<211> LENGTH: 10
<212> TYPE: PRT
<213> ORGANISM: Artificial Sequence
<220> FEATURE:
<223> OTHER INFORMATION: synthesized

<400> SEQUENCE: 39

Ile Val Ser Tyr Ser Gly Ser Gly Leu Asn
 1               5                  10

<210> SEQ ID NO 40
<211> LENGTH: 9
<212> TYPE: PRT
<213> ORGANISM: Homo sapiens

<400> SEQUENCE: 40

Ser Thr Ser Tyr Asp Arg Gly Asp Ser
 1               5

<210> SEQ ID NO 41
<211> LENGTH: 7
<212> TYPE: PRT
<213> ORGANISM: Homo sapiens

<400> SEQUENCE: 41

Arg Ser Lys Lys Thr Met Leu
 1               5

<210> SEQ ID NO 42
<211> LENGTH: 6
<212> TYPE: PRT
<213> ORGANISM: Homo sapiens

<400> SEQUENCE: 42

Ile Thr Ser Glu Ala Thr
 1               5

<210> SEQ ID NO 43
<211> LENGTH: 6
<212> TYPE: PRT
<213> ORGANISM: Homo sapiens

<400> SEQUENCE: 43

Asn Gly Lys Leu Phe Leu
 1               5

<210> SEQ ID NO 44
<211> LENGTH: 8
<212> TYPE: PRT
<213> ORGANISM: Homo sapiens

<400> SEQUENCE: 44

Phe Ser Val Pro Val Ala Leu Ser
 1               5
```

```
<210> SEQ ID NO 45
<211> LENGTH: 20
<212> TYPE: PRT
<213> ORGANISM: Homo sapiens
<220> FEATURE:
<221> NAME/KEY: VARIANT
<222> LOCATION: 3, 13
<223> OTHER INFORMATION: Xaa is K or A
<220> FEATURE:
<221> NAME/KEY: VARIANT
<222> LOCATION: 10, 20
<223> OTHER INFORMATION: Xaa is R or A

<400> SEQUENCE: 45

Leu Arg Xaa Leu Arg Lys Arg Leu Leu Xaa Leu Arg Xaa Leu Ala Lys
 1               5                  10                  15

Arg Leu Leu Xaa
            20

<210> SEQ ID NO 46
<211> LENGTH: 10
<212> TYPE: PRT
<213> ORGANISM: Homo sapiens

<400> SEQUENCE: 46

Ile Lys Thr Lys Lys Phe Leu Lys Lys Thr
 1               5                  10

<210> SEQ ID NO 47
<211> LENGTH: 13
<212> TYPE: PRT
<213> ORGANISM: Homo sapiens

<400> SEQUENCE: 47

Pro Tyr Leu Leu Asp Phe Gln Lys Lys Trp Gln Glu Glu
 1               5                  10

<210> SEQ ID NO 48
<211> LENGTH: 7
<212> TYPE: PRT
<213> ORGANISM: Homo sapiens

<400> SEQUENCE: 48

Gln Lys Arg Leu Asp Gly Ser
 1               5

<210> SEQ ID NO 49
<211> LENGTH: 72
<212> TYPE: DNA
<213> ORGANISM: Artificial Sequence
<220> FEATURE:
<223> OTHER INFORMATION: synthesized
<220> FEATURE:
<221> NAME/KEY: repeat_unit
<222> LOCATION: (34)...(36)
<223> OTHER INFORMATION: MNNa is a repeat, preferably where a is 3
<220> FEATURE:
<221> NAME/KEY: repeat_unit
<222> LOCATION: (46)...(48)
<223> OTHER INFORMATION: MNNb is a repeat, preferably where b is 3

<400> SEQUENCE: 49
ctcctcctcc tcctcgacgt ccatataata attmnnatcg ccacgmnntg gccccactct    60
cgcacaataa ta                                                       72
```

```
<210> SEQ ID NO 50
<211> LENGTH: 72
<212> TYPE: DNA
<213> ORGANISM: Artificial Sequence
<220> FEATURE:
<223> OTHER INFORMATION: synthesized
<220> FEATURE:
<221> NAME/KEY: repeat_unit
<222> LOCATION: (34)...(36)
<223> OTHER INFORMATION: MNNa is a repeat, preferably a is 3
<220> FEATURE:
<221> NAME/KEY: repeat_unit
<222> LOCATION: (46)...(48)
<223> OTHER INFORMATION: MNNb is a repeat, preferably b is 3

<400> SEQUENCE: 50
ctcctcctcc tcctcgacgt ccatataata gcamnnatcg ccacgmnngc accccactct      60
cgcacaataa ta                                                          72

<210> SEQ ID NO 51
<211> LENGTH: 72
<212> TYPE: DNA
<213> ORGANISM: Artificial Sequence
<220> FEATURE:
<223> OTHER INFORMATION: synthesized
<220> FEATURE:
<221> NAME/KEY: repeat_unit
<222> LOCATION: (22)...(24)
<223> OTHER INFORMATION: MNNa is a repeat, preferably a is 3
<220> FEATURE:
<221> NAME/KEY: repeat_unit
<222> LOCATION: (46)...(48)
<223> OTHER INFORMATION: MNNb is a repeat, preferably b is 5

<400> SEQUENCE: 51
ctcctcctcc tcctcgacgt cmnncagaaa actcccttga ttaccmnnac ctctcgcaca      60
gtaatacagg gc                                                          72

<210> SEQ ID NO 52
<211> LENGTH: 75
<212> TYPE: DNA
<213> ORGANISM: Artificial Sequence
<220> FEATURE:
<223> OTHER INFORMATION: synthesized
<220> FEATURE:
<221> NAME/KEY: repeat_unit
<222> LOCATION: (40)...(42)
<223> OTHER INFORMATION: MNN4 is a direct repeat of MNN, four times

<400> SEQUENCE: 52
ctcctcctcc tcctcgacgt ccatataata gcaattcctm nncccaaacg agcacccac       60 tctcgcacaa taata                                                       75

<210> SEQ ID NO 53
<211> LENGTH: 4
<212> TYPE: PRT
<213> ORGANISM: Artificial Sequence
<220> FEATURE:
<223> OTHER INFORMATION: synthesized

<400> SEQUENCE: 53

Arg Gly Asp Ile
 1

<210> SEQ ID NO 54
<211> LENGTH: 22
<212> TYPE: DNA
<213> ORGANISM: Artificial Sequence
```

```
<220> FEATURE:
<223> OTHER INFORMATION: synthesized

<400> SEQUENCE: 54
gcaattaacc ctcactaaag gg                                              22

<210> SEQ ID NO 55
<211> LENGTH: 28
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 9, 10, 11, 15, 16, 17
<223> OTHER INFORMATION: Xaa = Any Amino Acid

<400> SEQUENCE: 55

Tyr Tyr Cys Ala Arg Val Gly Pro Xaa Xaa Xaa Arg Gly Asp Xaa Xaa
 1               5                  10                  15

Xaa Asn Tyr Tyr Met Asp Val Glu Glu Glu Glu Glu
             20                  25

<210> SEQ ID NO 56
<211> LENGTH: 28
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 9, 10, 11, 15, 16, 17
<223> OTHER INFORMATION: Xaa = Any Amino Acid

<400> SEQUENCE: 56

Tyr Tyr Cys Ala Arg Val Gly Cys Xaa Xaa Xaa Arg Gly Asp Xaa Xaa
 1               5                  10                  15

Xaa Cys Tyr Tyr Met Asp Val Glu Glu Glu Glu Glu
             20                  25

<210> SEQ ID NO 57
<211> LENGTH: 90
<212> TYPE: DNA
<213> ORGANISM: Artificial Sequence
<220> FEATURE:
<223> OTHER INFORMATION: synthesized
<220> FEATURE:
<221> NAME/KEY: repeat_region
<222> LOCATION: (22)...(30)
<223> OTHER INFORMATION: M is either A or C; N is A, C, G, or T
<220> FEATURE:
<221> NAME/KEY: repeat_region
<222> LOCATION: (52)...(66)
<223> OTHER INFORMATION: M is either A or C; N is A, C, G, or T

<400> SEQUENCE: 57
ctcctcctcc tcctcgacgt cmnnmnnmnn cagaaaactc ccttgattac cmnnmnnmnn    60
mnnmnnacct ctcgcacagt aatacacggc                                      90

<210> SEQ ID NO 58
<211> LENGTH: 30
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 9, 10, 11, 12, 13, 21, 22, 23
```

<223> OTHER INFORMATION: Xaa = Any Amino Acid

<400> SEQUENCE: 58

Ala Val Tyr Tyr Cys Ala Arg Gly Xaa Xaa Xaa Xaa Xaa Gly Asn Gln
 1               5                  10                  15

Gly Ser Phe Leu Xaa Xaa Xaa Asp Val Glu Glu Glu Glu
            20              25                  30

<210> SEQ ID NO 59
<211> LENGTH: 21
<212> TYPE: DNA
<213> ORGANISM: Artificial Sequence
<220> FEATURE:
<223> OTHER INFORMATION: synthesized

<400> SEQUENCE: 59
gaattctaaa ctagctagtc g                                            21

<210> SEQ ID NO 60
<211> LENGTH: 21
<212> TYPE: DNA
<213> ORGANISM: Artificial Sequence
<220> FEATURE:
<223> OTHER INFORMATION: synthesized

<400> SEQUENCE: 60
atactgctga cagtaataca c                                            21

<210> SEQ ID NO 61
<211> LENGTH: 57
<212> TYPE: DNA
<213> ORGANISM: Artificial Sequence
<220> FEATURE:
<223> OTHER INFORMATION: synthesized
<220> FEATURE:
<221> NAME/KEY: repeat_region
<222> LOCATION: (19)...(29)
<223> OTHER INFORMATION: n = A,T,C or G. k = G or T

<400> SEQUENCE: 61
tattactgtc agcagtatnn knnknnknnk actttcggcg gagggaccaa ggtggag     57

<210> SEQ ID NO 62
<211> LENGTH: 21
<212> TYPE: DNA
<213> ORGANISM: Artificial Sequence
<220> FEATURE:
<223> OTHER INFORMATION: synthesized

<400> SEQUENCE: 62
aatacgactc actatagggc g                                            21

<210> SEQ ID NO 63
<211> LENGTH: 75
<212> TYPE: DNA
<213> ORGANISM: Artificial Sequence
<220> FEATURE:
<223> OTHER INFORMATION: synthesized
<220> FEATURE:
<221> NAME/KEY: repeat_region
<222> LOCATION: (31)...(48)
<223> OTHER INFORMATION: n = A,T,C or G. k = G or T

<400> SEQUENCE: 63
gattttgcag tgtattactg tcagcagtat nnknnknnkn nknnknnkac tttcggcgga   60
gggaccaagg tggag                                                   75

```
<210> SEQ ID NO 64
<211> LENGTH: 75
<212> TYPE: DNA
<213> ORGANISM: Artificial Sequence
<220> FEATURE:
<223> OTHER INFORMATION: synthesized
<220> FEATURE:
<221> NAME/KEY: repeat_region
<222> LOCATION: (22)...(51)
<223> OTHER INFORMATION: n = A,T,C or G. k = G or T

<400> SEQUENCE: 64
gattttgcag tgtattactg tnnknnknnk nnknnknnkn nknnknnknn kttcggcgga      60
gggaccaagg tggag                                                      75

<210> SEQ ID NO 65
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 4
<223> OTHER INFORMATION: Xaa = Any Amino Acid

<400> SEQUENCE: 65

Arg Gly Asp Xaa Arg
 1               5

<210> SEQ ID NO 66
<211> LENGTH: 6
<212> TYPE: PRT
<213> ORGANISM: Artificial Sequence
<220> FEATURE:
<223> OTHER INFORMATION: synthesized

<400> SEQUENCE: 66

Gly Arg Gly Asp Ser Pro
 1               5

<210> SEQ ID NO 67
<211> LENGTH: 18
<212> TYPE: PRT
<213> ORGANISM: Artificial Sequence
<220> FEATURE:
<223> OTHER INFORMATION: synthesized
<220> FEATURE:
<221> NAME/KEY: VARIANT
<222> LOCATION: 7, 8, 9, 10
<223> OTHER INFORMATION: Xaa = Any Amino Acid

<400> SEQUENCE: 67

Val Gly Cys Ser Phe Gly Xaa Xaa Xaa Xaa Arg Asn Cys Tyr Tyr Met
 1               5                  10                  15

Asp Val

<210> SEQ ID NO 68
<211> LENGTH: 11
<212> TYPE: PRT
<213> ORGANISM: Artificial Sequence
<220> FEATURE:
<223> OTHER INFORMATION: synthesized

<400> SEQUENCE: 68

Gly Ser Phe Gly Arg Gly Asp Ile Arg Asn Gly
```

```
1               5                   10
```

<210> SEQ ID NO 69
<211> LENGTH: 11
<212> TYPE: PRT
<213> ORGANISM: Artificial Sequence
<220> FEATURE:
<223> OTHER INFORMATION: synthesized

<400> SEQUENCE: 69

```
Cys Ser Phe Gly Arg Asn Asp Ser Arg Asn Cys
 1               5                   10
```

<210> SEQ ID NO 70
<211> LENGTH: 13
<212> TYPE: PRT
<213> ORGANISM: Artificial Sequence
<220> FEATURE:
<223> OTHER INFORMATION: synthesized

<400> SEQUENCE: 70

```
Gly Cys Ser Phe Gly Arg Asn Asp Ser Arg Asn Cys Tyr
 1               5                   10
```

<210> SEQ ID NO 71
<211> LENGTH: 11
<212> TYPE: PRT
<213> ORGANISM: Artificial Sequence
<220> FEATURE:
<223> OTHER INFORMATION: synthesized

<400> SEQUENCE: 71

```
Cys Ser Phe Gly Arg Thr Asp Gln Arg Asn Cys
 1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: synthesized

<400> SEQUENCE: 72

```
Gly Cys Ser Phe Gly Arg Thr Asp Gln Arg Asn Cys Tyr
 1               5                   10
```

<210> SEQ ID NO 73
<211> LENGTH: 4
<212> TYPE: PRT
<213> ORGANISM: Artificial Sequence
<220> FEATURE:
<223> OTHER INFORMATION: synthesized

<400> SEQUENCE: 73

```
Arg Trp Asp Ala
 1
```

<210> SEQ ID NO 74
<211> LENGTH: 4
<212> TYPE: PRT
<213> ORGANISM: Artificial Sequence
<220> FEATURE:
<223> OTHER INFORMATION: synthesized

<400> SEQUENCE: 74

```
Arg Ala Asp Arg
 1
```

-continued

```
<210> SEQ ID NO 75
<211> LENGTH: 4
<212> TYPE: PRT
<213> ORGANISM: Artificial Sequence
<220> FEATURE:
<223> OTHER INFORMATION: synthesized

<400> SEQUENCE: 75

Lys Arg Asp Met
 1

<210> SEQ ID NO 76
<211> LENGTH: 4
<212> TYPE: PRT
<213> ORGANISM: Artificial Sequence
<220> FEATURE:
<223> OTHER INFORMATION: synthesized

<400> SEQUENCE: 76

Arg Val Asp Asp
 1

<210> SEQ ID NO 77
<211> LENGTH: 5
<212> TYPE: PRT
<213> ORGANISM: Artificial Sequence
<220> FEATURE:
<223> OTHER INFORMATION: synthesized

<400> SEQUENCE: 77

Ala Gln Val Lys Leu
 1               5

<210> SEQ ID NO 78
<211> LENGTH: 5
<212> TYPE: PRT
<213> ORGANISM: Artificial Sequence
<220> FEATURE:
<223> OTHER INFORMATION: synthesized

<400> SEQUENCE: 78

Gly Gly Gly Gly Ser
 1               5
```

METHODS FOR PRODUCING POLYPEPTIDE BINDING SITES, MONOCLONAL ANTIBODIES AND COMPOSITIONS THEREOF

This application is a 371 of PCT/US94/01258 filed Feb. 2, 1994, which is a continuation-in-part of Ser. No. 08/084,542 filed Jun. 28, 1993 now abandoned, which is a continuation-in-part of Ser. No. 08/012,566 filed Feb. 2, 1993 now abandoned.

This invention was made with government support under Contract No. 1RO1 CA56483 by the National Institutes of Health. The government has certain rights in the invention.

TECHNICAL FIELD

The present invention relates generally to the field of protein biochemistry and immunology, and relates specifically to methods for producing polypeptide binding sites specific for preselected targets.

BACKGROUND

Protein interactions with other molecules is basic to biochemistry. Protein interactions include receptor-ligand interactions, antibody-antigen interactions, cell-cell contact and pathogen interactions with target tissues. Protein interactions can involve contact with other proteins, with carbohydrates, oligosaccharides, lipids, metal ions and the like materials.

The basic unit of protein interaction is the region of the protein involved in contact and recognition, and is referred to as the binding site.

There is an increasing need to find new molecules which can effectively modulate a wide range of biological processes, for applications in medicine and agriculture. Thus, there is a need for systematic and rapid development of binding sites on proteins for use in the construction of protein binding site analogs and antagonists, proteins with improved or altered binding specificities and the attendant altered function associated with the altered specificity, and antibodies with unique antigen specificities.

Numerous strategies have been developed for preparing proteins having new binding specificities besides the conventional technique of random screening of natural products. These approaches generally involve the synthetic production of large numbers of random molecules followed by some selection procedure to identify the molecule of interest. For example, epitope libraries have been developed using random polypeptides displayed on the surface of filamentous phage particles. The library is made by synthesizing a repertoire of random oligonucleotides to generate all combinations, followed by their insertion into a phage vector. Each of the sequences is separately cloned and expressed in phage, and the relevant expressed peptide can be selected by finding those phage that bind to the particular target. The phages recovered in this way can be amplified and the selection repeated. The sequence of the peptide is decoded by sequencing the DNA. See for example Cwirla et al., *Proc. Natl. Acad. Sci., USA*, 87:6378–6382 (1990); Scott et al., *Science*, 249:386–390 (1990); and Devlin et al., *Science*, 249:404–406 (1990).

Another approach involves large arrays of peptides that are synthesized in parallel and screened with acceptor molecules labelled with fluorescent or other reporter groups. The sequence of any effective peptide can be decoded from its address in the array. See for example Geysen et al., *Proc. Natl. Acad. Sci., USA*, 81:3998–4002 (1984); Maeji et al., *J. Immunol. Met.*, 146:83–90 (1992); and Fodor et al., *Science*, 251: 767–775 (1991).

In another approach, Lam et al., *Nature*, 354:82–84 (1991) describes combinatorial libraries of peptides that are synthesized on resin beads such that each resin bead contains about 20 pmoles of the same peptide. The beads are screened with labelled acceptor molecules and those with bound acceptor are searched for by visual inspection, physically removed, and the peptide identified by direct sequence analysis. In principle, this method could be used with other chemical entities but it requires sensitive methods for sequence determination.

A different method of solving the problem of identification in a combinatorial peptide library is used by Houghten et al., *Nature*, 354:84–86 (1991). For hexapeptides of the 20 natural amino acids, 400 separate libraries are synthesized, each with the first two amino acids fixed and the remaining four positions occupied by all possible combinations. An assay, based on competition for binding or other activity, is then used to find the library with an active peptide. Then twenty new libraries are synthesized and assayed to determine the effective amino acid in the third position, and the process is reiterated in this fashion until the active hexapeptide is defined. This is analogous to the method used in searching a dictionary; the peptide is decoded by construction using a series of sieves or buckets and this makes the search logarithmic.

Large libraries of wholly or partially synthetic antibody combining sites, or paratopes, have been constructed utilizing filamentous phage display vectors, referred to as phagemids, yielding large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991). Combinatorial libraries of antibodies have been produced using both the cpVIII membrane anchor (Kang et al., supra) and the cpIII membrane anchor. Barbas et al., *Proc. Natl. Acad. Sci., USA*, 88:7978–7982 (1991).

The diversity of a filamentous phage-based combinatorial antibody library can be increased by shuffling of the heavy and light chain genes (Kang et al., *Proc. Natl. Acad. Sci., USA*, 88:11120–11123, 1991), by altering the CDR3 regions of the cloned heavy chain genes of the library (Barbas et al., *Proc. Natl. Acad. Sci. USA*, 89:4457–4461, 1992), and by introducing random mutations into the library by error-prone polymerase chain reactions (PCR). Gram et al., *Proc. Natl. Acad. Sci., USA*, 89:3576–3580, 1992).

Mutagenesis of proteins has been utilized to alter the function, and in some cases the binding specificity, of a protein. Typically, the mutagenesis is site-directed, and therefore laborious depending on the systematic choice of mutation to induce in the protein. See, for example Corey et al., *J. Amer. Chem. Soc.*, 114:1784–1790 (1992), in which rat trypsins were modified by site-directed mutagenesis. Partial randomization of selected codons in the thymidine kinase (TK) gene was used as a mutagenesis procedure to develop variant TK proteins. Munir et al., *J. Biol. Chem.*, 267:6584–6589 (1992).

Using the random synthetic hexapeptide library displayed on filamentous phage, O'Neil et al., *Science*, 249:774–778 (1990), described the identification of a variety of different hexapeptides that contain the sequence Arg-Gly-Asp (RGD) or Lys-Gly-Asp (KGD) and that bind to the integrin GPIIb/IIIa.

In another approach, Roberts et al., *Gene*, 121:9–15 (1992), describes the point mutation of a protease inhibitor (BPTI) as a fusion protein with gene III of a phagemid, and demonstrated a change in binding specificity such that the mutant binds human neutrophil elastase rather than trypsin. Similarly, Roberts et al., *Proc. Natl. Acad. Sci., USA*, 89:2429–2433 (1992), produced by mutagenesis a library of phage displaying mutant trypsin inhibitor, and isolated variant enzymes with increased affinity.

Tomiyama described an antibody designated PAC-1 which binds the integrin GPIIb-IIIa and contains the sequence Arg-Tyr-Asp (RYD) in the antibody's third complementarity determining region of the heavy chain. Tomiyama et al., *J. Biol. Chem.*, 267:18085–18092 (1992). Antibody PAC-1 is a marker for platelet activation and its binding to GPIIb-IIIa can be blocked using peptides that contain the RGD sequence.

BRIEF DESCRIPTION OF THE INVENTION

Methods have now been discovered using the phagemid vectors to produce a binding site capable of binding (interacting with) any of a large variety of target molecules.

Thus, in one embodiment, the invention describes a method for producing in a polypeptide a binding site capable of binding a preselected agent comprising introducing a nucleotide sequence that codes for an amino acid residue sequence defining the binding site into a CDR region of a nucleic acid comprising an immunoglobulin heavy or light chain gene by amplifying the CDR region of the immunoglobulin gene by a primer extension reaction using a primer oligonucleotide. The oligonucleotide has 5' and 3' termini and comprises:

i) a nucleotide sequence at the 3' termini capable of hybridizing to a first framework region of the immunoglobulin gene;

ii) a nucleotide sequence at the 5' termini capable of hybridizing to a second framework region of the immunoglobulin gene; and iii) a nucleotide sequence between the 5' and 3' termini according to the formula:

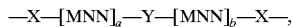

where the sum of a and b is from 5 to 50, X is a trinucleotide encoding cysteine or a native amino acid residue coded by the immunoglobulin gene, N is independently any nucleotide, M is adenine (A) or cytosine (C) or analogs thereof, Y is a nucleotide sequence that encodes a minimum recognition domain of the binding site, and the 5' and 3' terminal nucleotide sequences have a length of about 6 to 50 nucleotides in length.

In preferred embodiments, the immunoglobulin is human, and more preferably the CDR is CDR3.

Additionally contemplated for use in this invention is the complementary nucleotide sequence of the preferred oligonucleotide formulation and identified sequences. Specifically, the complementary nucleotide has 5' and 3' termini between which is the nucleotide formulation —X—[NNK]$_a$—Y—[NNK]$_b$—X—. This alternative embodiment of a complementary oligonucleotide thus hybridizes to the non-coding (antisense) strand of the template DNA.

Insofar as the method can be applied to any of a variety of known protein binding sites, the binding site can be an RGD-dependent binding site, a CD4 receptor binding site on HIV gp120, or a vitronectin receptor binding site on vitronectin to name but a few possibilities.

Also contemplated is an oligonucleotide useful as a primer for producing a binding site in a polypeptide coded for by a immunoglobulin heavy or light chain gene. The oligonucleotide has 5' and 3' termini and comprises:

i) a nucleotide sequence at the 3' termini capable of hybridizing to a first framework region of the immunoglobulin gene;

ii) a nucleotide sequence at the 5' termini capable of hybridizing to a second framework region of the immunoglobulin gene; and iii) a nucleotide sequence between the 5' and 3' termini according to the formula:

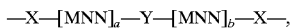

where the sum of a and b is from 5 to 50, X is a trinucleotide encoding cysteine or a native amino acid residue coded by the immunoglobulin gene, N is independently any nucleotide, M is adenine (A) or cytosine (C) or analogs thereof, Y is a nucleotide sequence that encodes a minimum recognition domain of the binding site, the 5' and 3' terminal nucleotide sequences have a length of about 6 to 50 nucleotides in length, and sequences complementary thereto.

In preferred embodiments, the oligonucleotide hybridizes to a human immunoglobulin, and more preferably defines a heavy chain CDR3 domain.

In another embodiment, the invention describes human monoclonal antibodies produced by the methods of the invention.

Preferred antibodies bind platelet glycoprotein gpIIb/IIIa, and inhibit platelet aggregation. Other antibodies described herein exhibit binding specificity for one and not other vitronectin receptor molecules. Particularly preferred antibodies immunoreact with target with an affinity of at least $1 \times 10^{-9}$ molar (M).

Polypeptides are described which inhibit fibrinogen binding to gpIIb/IIIa, and are also useful in therapeutic methods for inhibiting platelet aggregation. Further polypeptides are described which inhibit vitronectin binding to vitronectin receptor $\alpha_v\beta_3$, and are also useful in therapeutic methods for inhibiting vitronectin binding to vitronectin receptor $\alpha_v\beta_3$.

Therapeutic compositions containing the monoclonal antibodies or polypeptides of this invention are also described.

DNA expression vectors capable of expressing a phagemid immunoglobulin display protein are described which comprise a polynucleotide sequence that codes an immunoglobulin heavy chain polypeptide that includes in the CDR3 portion of the heavy chain a binding site able to bind a preselected target molecule.

Other embodiments will be apparent to one skilled in the art in view of the teachings within.

A major advantage of the methods of the invention derives from the fact that new binding specificities can be rapidly developed for use in a variety of ways, including the development of ligands with altered specificity for receptor, receptors with altered specificity for ligand, altered and/or increased antibody binding specificity, and new proteins or polypeptides that can bind oligosaccharides, nucleic acids, and the like.

BRIEF DESCRIPTION OF THE DRAWINGS

In the drawings forming a portion of this disclosure.

TABLE OF CORRESPONDENCE

Figure 1:
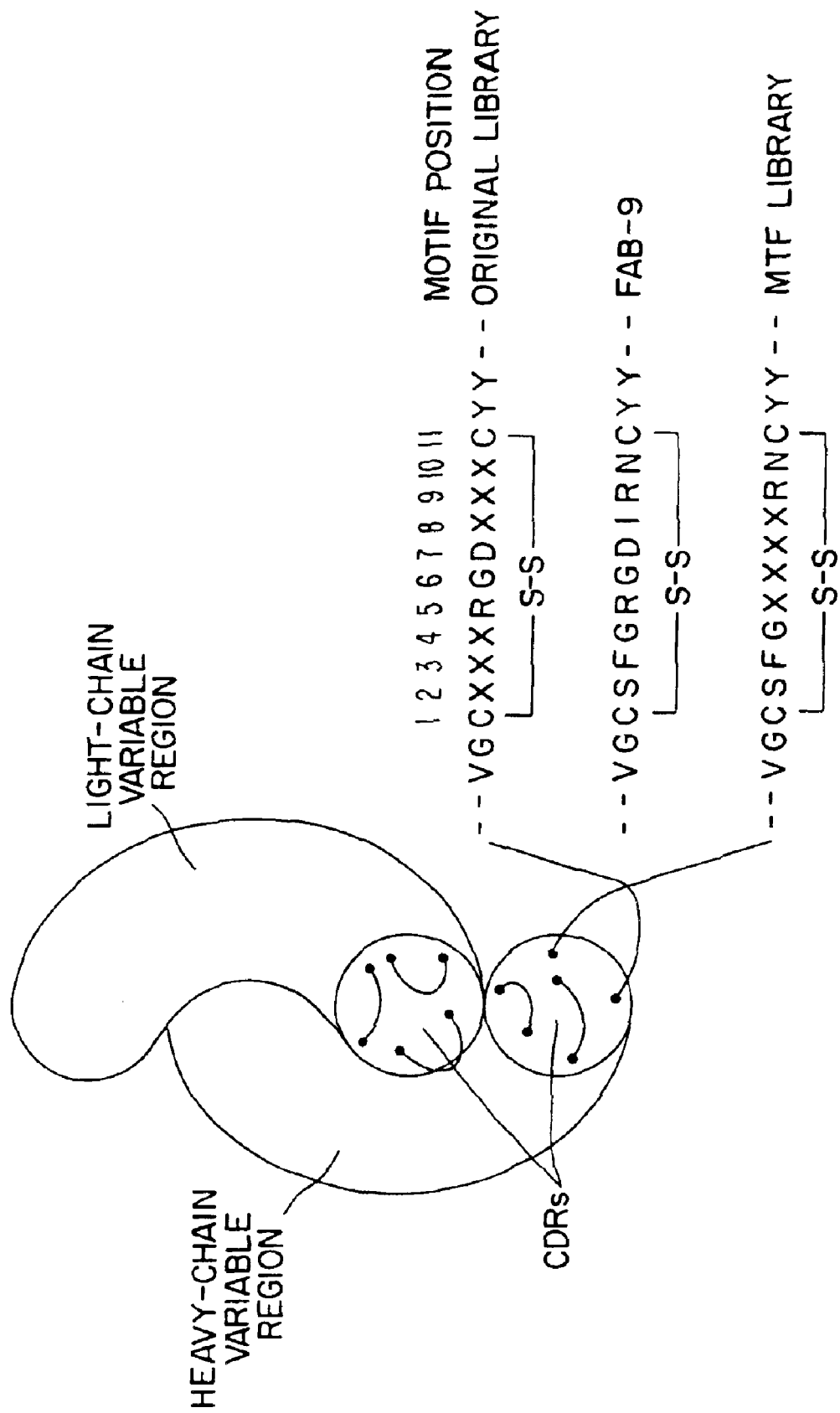
FIG. 1 illustrates the engineering and selection of synthetic anti-integrin antibodies as taught by the methods of this invention. Many RGD motifs are displayed at the apex of a flexible loop. Since antibody CDR's, particularly HCDR3, often exist as flexible loops, an integrin recognition sequence into this region. To optimize antibody binding affinity a -continued

| SYMBOL | | |
|---|---|---|
| 1-Letter | 3-Letter | AMINO ACID |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) molecule: a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

Vector: A rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) that are produced from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: A sequence of nucleotides in a DNA molecule coding for an amino acid residue sequence and including upstream and downstream DNA expression control elements.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: A particular sequence of contiguous nucleotide triplets (codons) employed in translation. The reading frame depends on the location of the translation initiation codon.

B. Methods for Producing Binding Sites

The present invention relates generally to methods for producing polypeptide-defined binding sites. The method involves the preparation of libraries of different binding sites on a phage display protein using degenerate oligonucleotides and primer extension reactions to incorporate the degeneracies into the binding site region of the display protein.

A binding site, described in more detail below, is any region of a protein or polypeptide that participates in protein-target molecule interactions, and therefore the identification of the primary sequence of a binding site is important in constructing a functional binding site-containing molecule.

The display of a binding site on a filamentous phage is essential to the present invention as it provides the ability to screen for capacity of the displayed binding site to bind to a preselected target molecule. Display is described in more detail but generally involves the preparation of a fusion protein containing a membrane anchor of the filamentous phage gene III or gene VIII protein fused to the polypeptide to be displayed that forms a binding site to be tested. Peptide display vectors using hexapeptides have been generally described before by Cwirla et al., *Proc. Natl. Acad. Sci., USA*, 87:6378–6382 (1990); Scott et al., *Science*, 249:386–390 (1990); and Devlin et al., *Science*, 249:404–406 (1990).

According to the present methods, the use of an antibody heavy or light chain as the display support structure on a recombinant filamentous phage, or phagemid, is particularly preferred. The use of an antibody support for a binding site provides a "scaffold" for presenting a conformationally constrained polypeptide to preselected binding conditions.

In this embodiment, a binding site is engineered into a complementarity determining region (CDR) of an immunoglobulin heavy or light chain that is presented on a phagemid, and the phagemid can be screened for binding to a preselected target molecule.

The introduction of a binding site onto a display phagemid involves the use of degenerate oligonucleotides to introduce into an immunoglobulin CDR region a series of different but related polypeptides defining a family of binding sites. The degenerate oligonucleotides contain regions of degeneracy to produce a library of different binding site structures, but also contain a region that is conserved that define a minimum binding site polypeptide known to represent an important recognition portion of the binding site to be developed. An example of a minimum binding site polypeptide is the RGD tripeptide found in many ligands that bind to integrins.

Thus, the method comprises the basic step of introducing a nucleotide sequence that codes for an amino acid sequence that defines a binding site into a gene that codes a phagemid display protein. The introduction step is conducted by amplifying a display region of the display protein gene by a primer extension reaction using a primer oligonucleotide having (1) regions complementary to the display protein gene, (2) regions that code a minimum binding site and (3) regions of degeneracy that introduce the variability into the resulting pool of display proteins having binding sites.

After the primer extension reaction, which may be accomplished in a variety of modes including polymerase chain reaction (PCR), crossover PCR, and the like, the resulting population of display protein genes are expressed in phagemids to form a population of phagemid particles having the display proteins with binding sites on the particle surface. The population of particles are then screened for the presence of particles containing a binding site that binds to a preselected target molecule.

In one preferred embodiment, a library was prepared having the RGD binding site introduced into a display protein comprised of immunoglobulin variable domain. In this approach, the domains immediately adjacent to the codons for "RGD" were randomized using degenerate oligonucleotides in a primer extension reaction.

By this approach, large populations of antibody molecules were obtained which contain the RGD tripeptide in the binding site, and which bind to selected integrins against which they were screened for binding. Exemplary antibodies produced by this are described herein.

In a related embodiment, the invention provides a method for preparing additional binding sites using a binding site produced by the above methods as a starting material, which can be further mutagenized and screened for binding activity. By using a binding site having a desired engineered binding specificity as a starting material, one can increase the binding affinity or binding specificity, or both, to produce improved binding sites. In particular, it may be desirable to preserve aspects of the binding site, referred to as motifs, and at the same time selectively mutagenize other portions of the binding site. The combination of random mutagenesis of regions of the binding site together with preservation of selected motifs is referred to as selected binding site motif engineering.

In a particularly preferred embodiment, selected binding site motif engineering involves first optimizing one motif, and then optimizing a second motif. As an example, described in detail in the Examples, the RGD motif was first introduced into an antibody to produce a binding site specific for the integrins $\alpha_{IIb}\beta_3$ and $\alpha_v\beta_3$. Subsequently, a preferred antibody produced in the first step was sequenced, and a second oligonucleotide was designed that preserves sites flanking the RGD motif, but intentionally randomizes the RGD domain, in order to identify a motif in place of RGD that exhibits enhanced specificity.

Exemplary oligonucleotides useful for such selected motif engineering are described herein.

C. Binding Site Polypeptides

A binding site can be any polypeptide sequence, typically about 3 to 20 amino acid residues in length but can be from 3 up to 50 amino acid residues in length, that defines a region of a protein or polypeptide which selectively interacts with another molecule or family of related molecules, referred to as target molecules.

As is known in protein biochemistry, proteins, and therefore binding sites as defined herein, can interact with a wide diversity of molecules including other proteins, in the form of receptors, tissue structures, and soluble proteins, polypeptides including degraded proteins, polypeptide hormones and ligands, lipid, oligosaccharides and carbohydrates, nucleic acids and inorganic molecules.

As shown herein and by other work in the field, the amino acid residue sequence of a binding site can tolerate some degree of variability and still retain a degree of capacity to bind the target molecule. Furthermore, changes in the sequence can result in changes in the binding specificity and in the binding constant between a preselected target molecule and the binding site. Thus, the present method is ideally suited to producing binding sites derived from a reference binding site in which the binding constant is increased, making a more potent binding reagent, or in which the specificity is altered or increased, making a more selective binding reagent.

The "reference" binding site is any known, or yet to be described, amino acid sequence having the ability to selectively bind a preselected agent. These reference binding sites can be taken from any protein known to be involved in protein-target interactions in which the amino acid reside sequence of the binding domain of the protein is known.

Exemplary reference binding sites are derived from the RGD-dependent integrin ligands, namely fibronectin, fibrinogen, vitronectin, von Willebrand factor and the like, from the envelope glycoprotein of viruses such as HIV gp120, EBV gp350/220, reovirus hemagglutinin, and the like, from cellular receptors such as CR2 or CD4, from protein hormones such as thyroid stimulating hormone (TSH), insulin, transferrin and the like, from apolipoproteins such as ApoE and ApoAI, from immunoglobulin CDRs, and from major histocompatibility complex class I or class II proteins.

In producing a binding site according to the present invention, the minimum binding or recognition domain of the binding site can be identified to increase the degree of possible variant binding sites based on the reference binding site. A minimum recognition domain is the minimum sequence of amino acids required to confer binding specificity to an otherwise random polypeptide. Where a minimum recognition domain is not known, a polypeptide having known binding properties can be used. An exemplary and prototype minimum recognition domain is the RGD tripeptide required in polypeptides which bind integrins in an RGD-dependent manner.

1. RGD-dependent Binding Sites

A preferred binding site is an RGD tripeptide-containing binding site, and is exemplary of the general methods described herein. Ligands having the RGD motif as a minimum recognition domain are well known, a partial list of which includes, with the corresponding integrin target in parenthesis, fibronectin ($\alpha_3\beta_1$, $\alpha_5\beta_1$, $\alpha_v\beta_1$, $\alpha_v\beta_1$, $\alpha_{IIb}\beta_3$, $\alpha_v\beta_3$ and $\alpha_v\beta_b$) fibrinogen ($\alpha_M\beta_2$ and $\alpha_{IIb}\beta_1$) von Willebrand factor ($\alpha_{IIb}\beta_3$ and $\alpha_v\beta_3$) vitronectin ($\alpha_{IIb}\beta_3$, $\alpha_v\beta_3$ and $\alpha_v\beta_5$). See, for example D'Souza et al., *Trends in Bioch. Sci.*, 16:246–250 (1991).

Particularly preferred RGD dependent binding sites identified by the present methods have an amino acid residue sequence shown below, and are shown to bind the human platelet glycoprotein gpIIb/IIIa ($\alpha_{IIb}\beta_3$) when present in a phagemid display protein:

| Designation | (SEQ ID NO) | Amino Acid Residue Sequence |
|---|---|---|
| IIb/IIIa-1 | 1 | VGCGALRGDDPWCYYMDV |
| IIb/IIIa-17 | 2 | VGYGRLRGDXPWCYYMDV[a] |
| IIb/IIIa-19 | 3 | VGCGRLRGDDPWCYYMDV |
| VnRβ$_3$-5 (Fab 9) | 4 | VGCSFGRGDIRNCYYMDV |
| MTFIIb/IIIa-1 | 5 | VGCSFGRGDDRNFYYMDV |
| MTFIIb/IIIa-5 | 4 | VGCSFGRGDIRNCYYMDV |

[a]The amino acid residue sequence at residue "X" has not been accurately determined.

Other preferred RGD-dependent binding sites identified by the present methods have an amino acid residue sequence shown below, and are shown to bind human vitronectin receptor (VnR) $\alpha_v\beta_3$ when present in a phagemid display protein:

| Designation | (SEQ ID NO) | Amino Acid Residue Sequence |
|---|---|---|
| VnRβ$_3$-4 | 6 | VGCTQGRGDWRSCYYMDV |
| VnRβ$_3$-5 (Fab 9) | 4 | VGCSFGRGDIRNCYYMDV |
| VnRβ$_3$-7 | 7 | VGCTYGRGDTRNCYYMDV |
| VnRβ$_3$-8 | 8 | VGCPIPRGDWRECYYMDV |
| VnRβ$_3$-10 | 9 | VGCTWGRGDERNCYYMDV |
| MTFVnRβ$_3$-3 | 4 | VGCSFGRGDIRNCYYMDV |

Still other preferred RGD-dependent binding sites identified by the present methods have an amino acid residue sequence shown below, and are shown to bind human vitronectin receptor (VnR) $\alpha_v\beta_5$ when present in a phagemid display protein:

| Designation | (SEQ ID NO) | Amino Acid Residue Sequence |
|---|---|---|
| VnRβ$_5$-6 | 10 | VGCDKRRGDRPRCYYMDV |
| VnRβ$_5$-11 | 11 | VGCSRRRGDRPQCYYMDV |

The specificity of the resulting phagemid display proteins were shown in the Examples to distinguish species of RGD-dependent receptors. That is, some selectively bound IIb/IIIa, some bound vitronectin receptor $\alpha_v\beta_3$, and some bound vitronectin receptor $\alpha_v\beta_5$, establishing the power of the present methods to produce unique and specific binding sites.

As described further herein, a preferred and exemplary phage display protein is an immunoglobulin heterodimer in which the fusion to a phagemid membrane anchor is through an immunoglobulin heavy chain polypeptide. In addition, a human monoclonal antibody in the form of a soluble Fab fragment can readily be prepared from the phagemid display vector. In this regard, the resulting human monoclonal antibody (Mab), whether a Mab, Fab and the like, produced having, for example, binding site IIb/IIIa-1 above is referred to generally as Mab IIb/IIIa-1 to connote the presence of the IIb/IIIa-1 binding site.

A preferred embodiment is a peptide containing the amino acid residue sequence of the binding site derived from an immunoglobulin heterodimer having a preselected binding specificity, such as IIb/IIIa-1. The corresponding peptide is referred to generally as peptide IIb/IIIa-1 to connote the presence of the IIb/IIIa-1 binding site. A preferred peptide has the amino acid residue sequence CSFGRGDIRNC (SEQ ID NO 12) derived from the binding site of VnRβ$_3$-5, also referred to as Fab 9. Peptides of this invention are contemplated for use in both linear and circularized topologies. As described in the Examples, the VnRB3-5-derived peptide inhibits the binding of the high affinity ligand, vitronectin, to the vitronectin receptor, $\alpha_v\beta_3$, equivalent to that seen with the soluble Fab from which the peptide is derived.

2. Non-RGD-dependent Integrin Binding Sites

In a further embodiment, a binding site that mimics a non-RGD-dependent binding site on an integrin receptor and having the binding specificity of a high affinity ligand that recognizes the selected integrin is contemplated. Preferred non-RGD-dependent binding sites identified by the present methods as described in herein have an amino acid residue sequence shown below and are shown to bind human vitronectin receptor (VnR) $\alpha_v\beta_3$ when present in a phagemid display protein.

| Designation | (SEQ ID NO) | Amino Acid Residue Sequence |
|---|---|---|
| MTFVβ$_3$-18 | 13 | VGCSFGRADTRNCYYMDV |
| MTFVβ$_3$-1 | 14 | VGCSGFRVDDRNCYYMDV |
| MTFVβ$_3$-9 | 15 | VGCSFGRQDARNCYYMDV |
| MTFVβ$_3$-15 | 16 | VGCSFGRSDVRNCYYMDV |
| MTFVβ$_3$-12 | 17 | VGCSFGRADRRNCYYMDV |
| MTFVβ$_3$-19 | 18 | VGCSFGRSDVRNFYYMDV |

Still other preferred non-RGD-dependent binding sites identified by the present methods as described herein have an amino acid residue sequence shown below, and are shown to bind human platelet glycoprotein gpIIb/IIIa when present in a phagemid display protein:

| Designation | (SEQ ID NO) | Amino Acid Residue Sequence |
|---|---|---|
| MTFIIb-IIIa-8 | 19 | VGCSFGRTXTRNCYYMDV |
| MTFIIb/IIIa-14 | 20 | VGCSFGRQDVRNCYYMDV |
| MTFIIb/IIIa-12 | 21 | VGCSFGRDDGRNCYYMDV |
| MTFIIb/IIIa-13 | 22 | VGCSFGRWDARNCYYMDV |
| MTFIIb/IIIa-16 | 23 | VGCSFGXGDRRNCYYMDV |
| MTFIIb/IIIa-7 | 24 | VGCSFGKRDMRNCYYMDV |
| MTFIIb/IIIa-10 | 25 | VGCSFGKGDNRNCYYMDV |
| MTFIIb/IIIa-2 | 26 | VGCSFGRTDQRNCYYMDV |
| MTFIIb/IIIa-19 | 27 | GVRRVLGNQGSFLPGWDV |
| MTFIIb/IIIa-21 | 28 | VGCSFGRXDGRNFYYMDV |
| MTFIIb/IIIa-23 | 29 | VGCSFGRRDERNCYYMDV |
| MTFIIb/IIIa-25 | 30 | VGCSFGRNDARNCYYMDV |
| MTFIIb/IIIa-31 | 31 | VGCSFGRRDERNCYYMDV |
| MTFIIb/IIIa-32 | 32 | VGCSFGRTDTRNCYYMDV |
| MTFIIb/IIIa-33 | 33 | VGCSFGRADNRNCYYMDV |
| MTFIIb/IIIa-40 | 34 | VGCSFGRNDSRNCYYMDV |

The amino acid residue sequence at residue "X" in SEQ ID NOs 19, 23, and 28 have not been accurately determined.

3. HIV Gp120 Binding Site

In another embodiment, a binding site that mimics a binding site on the CD4 lymphocyte receptor and having binding specificity for HIV gp120 is contemplated. The minimum recognition domain of a preferred gp120 site has the amino acid residue sequence GNQGSFL (SEQ ID NO 35).

4. EBV Gp350/220 Binding Site

In another embodiment, a binding site that mimics a binding site on the cell receptor CR2 and having binding specificity for the EBV gp350/220 receptor is contemplated. The minimum recognition domain of a preferred EBV gp350/220 binding site has the amino acid residue sequence EDPGFFNE (SEQ ID NO 36) or EDPGKQLYNVE (SEQ ID NO 37).

5. Other Binding Sites

Numerous other binding sites are contemplated by the present invention, and are readily obtainable by the present screening methods. Preferred minimum recognition domains of binding sites for use in the invention are described below.

The insulin receptor binding site on insulin has the amino acid residue sequence: RLFFNYLVIFEMVHLKE (SEQ ID NO 38).

The reovirus receptor binding site on the viral hemagglutinin protein has the sequence: IVSYSGSGLN (SEQ ID NO 39).

The fibrinogen receptor binding site on fibrinogen A alpha has the sequence: STSYDRGDS (SEQ ID NO 40).

Thyroid hormone receptor has two preferred binding sites on thyroid stimulating hormone (TSH), and TSH has two forms. The TSHα binding site sequences are RSKKTML (SEQ ID NO 41) and ITSEAT (SEQ ID NO 42). The TSHβ binding site sequences are NGKLFL (SEQ ID NO 43) and FSVPVALS (SEQ ID NO 44).

The LDL receptor binding site on the ApoE protein has the sequence: $(LRX_1LRKRLLX_2)_2$ (SEQ ID NO 45), where $X_1$ can be K or A, and where $X_2$ can be R or A.

The lipid A binding site has the sequence: IKTKKFLKKT (SEQ ID NO 46).

The lecithin-cholesterol acyltransferase (LCAT) binding site on the ApoAI protein has the sequence: PYLLDFQKKWQEE (SEQ ID NO 47).

The Mac-1 integrin receptor binding site on fibrinogen D-30 fragment has the sequence: QKRLDGS (SEQ ID NO 48).

D. Phagemid Display Proteins

The display of the binding site on a phagemid can be accomplished on any of the surface proteins of the filamentous phage particle, although particularly preferred are display proteins comprising gene III or gene VIII protein, as described herein. The use of gene III or gene VIII protein as a display protein on filamentous phage has been extensively described elsewhere herein.

Particularly preferred display proteins are fusions involving the use of the phage particle membrane anchor derived from gene III or gene VIII fused to an immunoglobulin heavy or light chain as described herein. In this embodiment, the binding site is displayed in a complementary determining region (CDR) of the immunoglobulin heavy or light chain, which in turn is a fusion to the membrane anchor domain of the phage's gene III or gene VIII protein.

When using an immunoglobulin heavy or light chain as the display protein, it is preferred to position the binding site within one or more complementary determining regions, CDR1, CDR2 or CDR3. Using the Kabat immunoglobulin amino acid residue sequence position numbering system, the light chain CDR's are as follows: CDR1 (residues 23–35), CDR2 (residues 49–57), and CDR3 (residues 88–98); and the heavy chain CDRs are as follows: CDR1 (residues 30–36), CDR2 (residues 49–66), and CDR3 (residues 94–103). See, Kabat et al., "Sequences of Proteins of Immunological Interest", Fourth ed., NIH, (1987).

When inserting a binding site into a CDR of an immunoglobulin fusion display protein, some, most or all of the CDR domain can be removed and substituted by the inserted binding site. It has been learned that the CDR is very accommodating to variably sized inserts without disrupting the ability of the immunoglobulin to assemble and display the inserted amino acid residue sequence.

In one embodiment, the phage display protein is engineered to include stabilization features in addition to the stabilization provided by the native structure of the display protein. To that end, cysteine residues can be coded for by the oligonucleotide, such that disulfide bridges can be formed. The placement of the cysteine residues can be varied, such that a loop structure of from about 5 to 20 amino acid residues is formed. An exemplary construction with cysteines is shown in the binding sites IIb/IIIa-1, IIb/IIIa-19, $VnR\beta_3$ sites -4, -5, -7, -8 and -10, and $VnR\beta_5$ sites -6 and -11.

In another embodiment, a phage display protein can be engineered to contain multiple binding sites. For example, using the heavy chain immunoglobulin as exemplary, binding sites can be introduced separately into one or more of the CDRs designated CDR1, CDR2 and CDR3. Additionally, one can introduce binding sites into a heavy chain CDR and a light chain CDR, into multiple heavy and light chain CDRs, and the like combinations.

E. Oligonucleotides

The preparation of a binding site according to the present invention involves the use of synthetic oligonucleotides designed to introduce a putative binding site into a display protein. Furthermore, the oligonucleotide strategies described herein have particular advantages in creating in a single reaction an extremely large population of different binding sites by the use of degenerate oligonucleotides.

1. Oligonucleotides Used to Engineer a Minimum Binding Site

The general structure of an oligonucleotide for use in one of the present methods has the general formula JOYOQ, where J and Q define regions of homology to regions of the display protein gene which flank the site in which a binding site is to be inserted, O defines region of degeneracy in which variable amino acid residues are introduced, and Y defines a minimum recognition domain of the binding site that is being introduced into the display protein's binding site.

The number of nucleotides for regions O or Y can vary widely, but must be in triplets so as to preserve the reading frame of the display protein. Typically, J and Q are of sufficient length to confer hybridization specificity with the template during the primer extension reaction. Thus, J and Q are typically each at least 6 nucleotides, and preferably each at least 9 nucleotides in length, although they can be 12, 15, 18, 21 and up to about 24 nucleotides in length. The O's are typically of a widely variable length coding typically from 3 to 20 amino acid residues. Y defines a minimum recognition domain of about 3 to 40 amino acids residues in length, although, typically 3 to 10 residues are preferred.

Where the display protein is an immunoglobulin, the homologies are directed to the immunoglobulin framework regions (FR) that flank the CDR into which the binding site is to be inserted.

Thus, in one embodiment, the invention contemplates an oligonucleotide useful as a primer for producing a binding site in a polypeptide coded for by a hybrid immunoglobulin heavy or light chain gene. The oligonucleotide has 5' and 3' termini and comprises:

i) a nucleotide sequence of about 5 to 50 nucleotides in length at the 3' termini capable of hybridizing to a first (upstream) framework region of the immunoglobulin gene;

ii) a nucleotide sequence of about 5 to 50 nucleotides in length at the 5' termini capable of hybridizing to a second (downstream) framework region of the immunoglobulin gene; and iii) a nucleotide sequence between said 5' and 3' termini according to the formula:

—X—[MNN]$_a$—Y—[MNN]$_b$—X—, where a and b are whole integers greater than zero, the sum of a and b is from 5 to 50, X is a trinucleotide encoding cysteine or a native amino acid residue coded by the immunoglobulin gene, N is independently any nucleotide, M is adenine (A) or cytosine (C) or analogs thereof, and Y is a nucleotide sequence that encodes a minimum recognition domain of said binding site, and wherein said 5' and 3' terminal nucleotide sequences have a length of about 6 to 50 nucleotides in length, and sequences complementary thereto.

Additionally contemplated for use in this invention is the complementary nucleotide sequence of an oligonucleotide formulation and identified sequence. Specifically, the complementary nucleotide for use in the invention may have 5' and 3' termini between which is the nucleotide formulation —X—[NNK]$_a$—Y—[NNK]$_b$—X—. This alternative embodiment of a complementary oligonucleotide thus hybridizes to the non-coding (antisense) strand of the template DNA.

Insofar as the use of a primer extension oligonucleotide (primer) in this invention is for the purpose of introducing directed mutations into a known immunoglobulin gene sequence, and insofar as one can mutagenize either the sense or antisense strand of a double stranded nucleic acid molecule, the use of the term "encode" in its various expressions is meant to refer to either the sense or antisense nucleotide sequence with the understanding that it is the sense strand which is used to define the corresponding amino acid residue sequence.

The choice of framework regions depends on the CDR into which the binding site is to be inserted. Thus, for example, for an insertion into CDR3, the 3' and 5' regions are selected as to be complementary in nucleotide sequence to the coding strand defining FR3 and FR4 that flank CDR3, respectively, where the oligonucleotide is to be complementary to the coding (sense) strand of the template DNA.

A preferred and exemplary CDR for insertion of a binding site is the CDR3 of immunoglobulin heavy chain. Particularly preferred is the immunoglobulin heavy chain display protein present in the vectors pC3AP313 and p7EIII, described herein.

Oligonucleotides used in the present methods that are particularly preferred for producing an RGD-dependent binding site have the formula: 5' CTCCTCCTCCTCCTCGACGTCCATATAATAATT [MNN]$_a$ATCGCCACG[MNN]$_b$ TGGCCCCACTCTCGCACAATAATA3' (SEQ ID NO 49), and preferably a is 3 and b is 3. An additional preferred oligonucleotide of this type has the formula: 5' CTCCTCCTCCTCCTCGACGTCCATATAATAGCA [MNN]$_a$ATCGCCACG[MNN]$_b$ GCACCCCACTCTCGCACAATAATA3' (SEQ ID NO 50), and preferably a is 3 and b is 3. This latter oligonucleotide is designed to introduce cysteine residues into the display protein flanking the binding site.

Oligonucleotides used in the present methods that are particularly preferred for producing an HIV gp120 binding site have the formula: 5' CTCCTCCTCCTCCTCGACGTC [MNN]$_a$ CAGAAAACTCCCTTGATTACC[MNN]$_b$ ACCTCTCGCACAGTAATACACGGC3' (SEQ ID NO 51), and preferably a is 3 and b is 5.

Other oligonucleotides are described in the Examples.

2. Oligonucleotides Used to Create Motif Switching Engineered Sites

In another embodiment, the invention describes oligonucleotides for use in the present methods which are designed to introduce (switch) a new motif into an engineered site. The oligonucleotide contains regions of degeneracy as before to produce a library of binding sites, except that selected regions of the oligonucleotide are designed to preserve regions of a preselected binding site.

For example, described herein, oligonucleotides were designed to introduce a known binding site motif "RGD" into a CDR region of an immunoglobulin, with the redundancies flanking the RDG motif. In the present example, the oligonucleotide used is based on a known binding site directed to an RGD-dependent ligand. The oligonucleotide is designed such that known sequences adjacent to the RGD motif are preserved, and the redundancy is introduced upon the RGD motif itself. The resulting binding sites do not necessarily contain the RGD motif, and in some cases a binding site is produced that does not contain RGD, but that does bind the target (receptor) with higher affinity.

A structure of an oligonucleotide for use in this motif switching embodiment has the general formula JLOPQ, where J and Q define regions of homology to regions of the display protein gene which flank the site in which a binding site is to be inserted (e.g., immunoglobulin framework domains as before), O defines a region of degeneracy in which variable amino acid residues are introduced, and L and P define domains of the binding site that is being preserved in the mutagenesis procedure. For the case of RGD, the region "O" overlays the RGD motif, resulting in scrambling of the sequence at that position, whereas the regions "L" and "P" adjacent to the RGD region are conserved. The inclusion of regions J and Q is optional.

Thus, in one embodiment, the invention describes an oligonucleotide useful as a primer for producing a binding site while preserving a motif in a polypeptide coded for by a immunoglobulin heavy or light chain gene, wherein the oligonucleotide has 5' and 3' termini according to the general formula: -LOP-. The oligonucleotide comprises:

i) a nucleotide sequence at said 3' termini capable of hybridizing to a first framework region of said immunoglobulin gene;

ii) a nucleotide sequence at said 5' termini capable of hybridizing to a second framework region of said immunoglobulin gene; and iii) a nucleotide sequence between said 5' and 3' termini according to the formula:

-L-[MNN]$_4$—P— where L and P are each one to ten trinucleotides encoding preselected CDR sequences, N is independently any nucleotide, M is adenine (A) or cytosine (C) or analogs thereof, and sequences complementary thereto.

In a preferred embodiment, L is 5 trinucleotides in length, and P is 8 trinucleotides in length. More preferably, L and P correspond in sequence to a heavy chain immunoglobulin variable region amino acid residue sequence. In a particularly preferred embodiment, the oligonucleotide has the nucleotide sequence 5'

CTCCTCCTCCTCCTCGACGTCCATATAATAGCAA TTCCT[MNN]₄CCCAAAC GAGCACCCCACTCTCG-CACAATAATA3' (SEQ ID NO 52).

Oligonucleotides for use in the present invention can be synthesized by a variety of chemistries as is well known. An excellent review is "Oligonucleotide Synthesis: A Practical Approach", ed. M. J. Gait, JRL Press, New York, N.Y. (1990). Suitable synthetic methods include, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979). Purification of synthesized oligonucleotides for use in primer extension and PCR reactions is well known. See, example Ausubel et al., "Current Protocols in Molecular Biology", John Wiley & Sons, New York, (1987). Exemplary synthesis is described in the Examples.

F. Primer Extension Reactions

The term "polynucleotide" as used herein in reference to primers, probes and nucleic acid fragments or segments to be synthesized by primer extension is defined as a molecule comprised of two or more deoxyribonucleotides or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarily with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nuc. Acids Res.*, 12:7057–70 (1984); Studier et al., *J. Mol. Biol.*, 189:113–130 (1986); and *Molecular Cloning: A Laboratory Manual, Second Edition*, Sambrook et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197–1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719–736 (1974).

The choice of a primer's nucleotide sequence depends on factors such as the distance on the nucleic acid from the region of the display protein gene into which a binding site is being introduced, its hybridization site on the nucleic acid relative to any second primer to be used, and the like.

The PCR reaction is performed using any suitable method. Generally it occurs in a buffered aqueous solution, i.e., a PCR buffer, preferably at a pH of 7–9, most preferably about 8. Preferably, a molar excess of the primer is admixed to the buffer containing the template strand. A large molar excess of about 104:1 of primer to template is preferred to improve the efficiency of the process.

The PCR buffer also contains the deoxyribonucleotide triphosphates DATP, dCTP, dGTP, and dTTP and a polymerase, typically thermostable, all in adequate amounts for primer extension (polynucleotide synthesis) reaction. The resulting solution (PCR admixture) is heated to about 90 degrees Celsius (90 C) to 100 C for about 1 to 10 minutes, preferably from 1 to 4 minutes. After this heating period the solution is allowed to cool to 54 C, which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40 C. An exemplary PCR buffer comprises the following: 50 millimolar (mM) KCl; 10 mM Tris-HCl; pH 8.3; 1.5 mM MgCl₂; 0.001% (wt/vol) gelatin, 200 micromolar (uM) dATP; 200 uM dTTP; 200 uM dCTP; 200 uM dGTP; and 2.5 units *Thermus aquaticus* DNA polymerase I (U.S. Pat. No. 4,889,818) per 100 microliters (ul) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acids Res.*, 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process, as is known for PCR.

PCR is typically carried out by thermocycling i.e., repeatedly increasing and decreasing the temperature of a PCR reaction admixture within a temperature range whose lower limit is about 10 C to about 40 C and whose upper limit is about 90 C to about 100 C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990), the teachings of which are hereby incorporated by reference.

Preferred PCR reactions using the oligonucleotides and methods of this invention are described in the Examples.

G. Phage Display Vectors

The methods of the present invention for preparing binding sites involve the use of phage display vectors for their particular advantage of providing a means to screen a very large population of expressed display proteins and thereby locate one or more specific clones that code for a desired binding reactivity.

The use of phage display vectors derives from the previously described use of combinatorial libraries of antibody molecules based on phagemids. The combinatorial library production and manipulation methods have been extensively described in the literature, and will not be reviewed in detail herein, except for those feature required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci., USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), the disclosures of which are hereby incorporated by reference.

1. Phage Display Vector Structure

A preferred phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa et al., *J. Biol. Chem.*, 256:9951–9958, 1981). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.*, 50:401–427 (1986); and Model et al., in "The Bacteriophages: Vol. 2", R. Calendar, ed. Plenum Publishing Co., pp. 375–456 (1988).

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei et al., *Nature*, 331:543–546 (1988).

The leader sequence of the pelB protein has previously been used as a secretion signal for fusion proteins (Better et al., *Science*, 240:1041–1043 (1988); Sastry et al., *Proc. Natl. Acad. Sci., USA*, 86:5728–5732 (1989); and Mullinax et al., *Proc. Natl. Acad. Sci., USA*, 87:8095–8099 (1990)). Amino acid residue sequences for other secretion signal polypeptide domains from *E. coli* useful in this invention as described in Oliver, *Escherichia coli* and *Salmonella Typhimurium*, Neidhard, F. C. (ed.), American Society for Microbiology, Washington, D.C., 1:56–69 (1987).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on PACYC and its derivatives. The ColE1 and p15A replicon have been extensively utilized in molecular biology, are available on a variety of plasmids and are described at least by Sambrook et al., in "Molecular Cloning: a Laboratory Manual", 2nd edition, Cold Spring Harbor Laboratory Press (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook et al., supra, at pages 1.3–1.4). This feature is particularly important when using binary vectors because a single host cell permissive for phage replication must support the independent and simultaneous replication of two separate vectors, for example when a first vector expresses a heavy chain polypeptide and a second vector expresses a light chain polypeptide.

In addition, those embodiments that include a prokaryotic replicon can also include a gene whose expression confers a selective advantage, such as drug resistance, to a bacterial host cell transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which a transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched et al., *Microbiol. Rev.*, 50:401–427, 1986; and Horiuchi, *J. Mol. Biol.*, 188:215–223, 1986). A preferred filamentous phage origin of replication for use in the present invention is an M13, f1 or fd phage origin of replication (Short et al., *Nucl. Acids Res.*, 16:7583–7600, 1988).

Preferred DNA expression vectors for cloning and expressing a phagemid display protein of this invention are the dicistronic plasmid expression vectors pC3AP313 and p7EIII described herein.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

Insofar as the expression vector for producing a human monoclonal antibody of this invention is carried in a host cell compatible with expression of the antibody, the invention contemplates a host cell containing a vector or polynucleotide of this invention. A preferred host cell is *E. coli*, as described herein.

Preferred expression vectors and plasmids that produce a phagemid display protein of this invention were deposited pursuant to Budapest Treaty requirements with the American 2. Use of Phagemid Display Vectors to Produce a Binding Site The method for producing a binding site in a phagemid display protein generally involves (1) introducing a binding site into a phagemid display protein vector by primer extension with an oligonucleotide as described herein, to form a large population of display vectors each capable of expressing different putative binding sites displayed on a phagemid surface display protein, (2) expressing the display protein and binding site on the surface of a filamentous phage particle, and (3) isolating the surface-expressed phage particle using affinity techniques such as panning of phage particles against a preselected target molecule, thereby isolating one or more species of phagemid containing a display protein containing a binding site that binds a preselected target molecule.

As a further characterization of the present invention the nucleotide and corresponding amino acid residue sequence of the gene coding the binding site is determined by nucleic acid sequencing. The primary amino acid residue sequence information provides essential information regarding the binding site's reactivity.

An exemplary preparation of a binding site in the CDR3 region of a heavy chain of an immunoglobulin is described in the Examples. The isolation of a particular vector capable of expressing a binding site of interest involves the introduction of the dicistronic expression vector able to express the phagemid display protein into a host cell permissive for expression of filamentous phage genes and the assembly of phage particles. Typically, the host is *E. coli*. Thereafter, a helper phage genome is introduced into the host cell containing the phagemid expression vector to provide the genetic complementation necessary to allow phage particles to be assembled. The resulting host cell is cultured to allow the introduced phage genes and display protein genes to be expressed, and for phage particles to be assembled and shed from the host cell. The shed phage particles are then harvested (collected) from the host cell culture media and screened for desirable binding properties. Typically, the harvested particles are "panned" for binding with a preselected molecule. The strongly binding particles are then collected, and individual species of particles are clonally isolated and further screened for binding to the target molecule. Phage which produce a binding site of desired binding specificity are selected.

As described in the Examples, one can use the preferred phagemid expression vectors as a starting material to introduce any of a variety of modifications into the expressed antibody's CDR region(s). Any of the desired antibody CDR sequences disclosed herein can be introduced by well known methods, including, but not limited to, the PCR-based mutagenesis methods, oligonucleotide synthesis and other recombinant DNA methodologies.

H. Human Monoclonal Antibodies

The present invention describes, in one embodiment, human monoclonal antibodies which contain a binding site as described herein and which bind specifically to a preselected target molecule. The invention also describes cell lines which produce the antibodies, methods for producing the cell lines, and methods for producing the human monoclonal antibodies.

Insofar as a display protein of this invention on a phagemid particle is, in preferred embodiments, a fusion protein between an immunoglobulin heavy or light chain and a filamentous phage membrane anchor, it is to be understood that the display protein is, in effect, an engineered immunoglobulin heavy or light chain into which a binding site has been introduced. Furthermore, in many embodiments, the expression of the display protein is prepared on the phagemid surface as a heterodimer formed between immunoglobulin heavy and light chain polypeptides, with one or the other being a fusion protein with the membrane anchor. Thus, where the heavy chain is used as the fusion protein, a display protein in preferred embodiments comprises a Fab fragment having an anchored heavy chain associated with a light chain.

The preparation of cell lines producing monoclonal antibodies of the invention is described in great detail further herein, and can be accomplished using the phagemid vector mutagenesis methods described herein, and using routine screening techniques which permit determination of the elementary binding patterns of the monoclonal antibody of interest indicative that the binding site has been produced. Thus, if a human monoclonal antibody being tested binds to the preselected target molecule, then the human monoclonal antibody being tested and the human monoclonal antibody produced by the cell lines of the invention are considered equivalent.

It is also possible to determine, without undue experimentation, if a human monoclonal antibody has the same (i.e., equivalent) specificity as a human monoclonal antibody of this invention by ascertaining whether the former prevents the latter from binding to a preselected target molecule. If the human monoclonal antibody being tested competes with the human monoclonal antibody of the invention, as shown by a decrease in binding by the human monoclonal antibody of the invention in standard competition assays for binding to the target molecule when present in the solid phase, then it is likely that the two monoclonal antibodies bind to the same, or a closely related, epitope.

Still another way to determine whether a human monoclonal antibody has the specificity of a human monoclonal antibody of the invention is to pre-incubate the human monoclonal antibody of the invention with the target molecule with which it is normally reactive, and then add the human monoclonal antibody being tested to determine if the human monoclonal antibody being tested is inhibited in its ability to bind the target molecule. If the human monoclonal antibody being tested is inhibited then, in all likelihood, it has the same, or functionally equivalent, epitopic specificity as the monoclonal antibody of the invention.

An additional way to determine whether a human monoclonal antibody has the specificity of a human monoclonal antibody of the invention is to determine the amino acid residue sequence of the CDR regions of the antibodies in question. Antibody molecules having identical, or functionally equivalent, amino acid residue sequences in their CDR regions have the same binding specificity. Methods for sequencing polypeptides is well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence.

Particularly preferred is a human monoclonal antibody having the binding specificity of the monoclonal antibody produced by an *E. coli* microorganism or produced by a plasmid vector that is deposited with the ATCC, as described further herein, or that is derived from a deposited plasmid vector, as described further herein.

Use of the term "having the binding specificity of" indicates that equivalent monoclonal antibodies exhibit the same or similar immunoreaction (binding) properties and compete for binding to a preselected target molecule.

The term "conservative variation or substitution" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

The term "conservative variation" also includes the use of a substituted amino acid in place of an unsubstituted parent amino acid provided that antibodies having the substituted polypeptide also bind to the preselected target molecule. Analogously, another preferred embodiment of the invention relates to polynucleotides which encode the above noted heavy and/or light chain polypeptides and to polynucleotide sequences which are complementary to these polynucleotide sequences. Complementary polynucleotide sequences include those sequences which hybridize to the polynucleotide sequences of the invention under stringent hybridization conditions.

Human monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies.

The invention contemplates, in one embodiment, a monoclonal antibody of this invention produced by the present methods.

In another preferred embodiment, the invention contemplates a truncated immunoglobulin molecule comprising a Fab fragment derived from a human monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods. A preferred method of producing a soluble Fab fragment is described herein.

1. RGD-dependent Human Monoclonal Antibodies a. Anti-GPIIb/IIIA Human Monoclonal Antibodies In one embodiment, the invention describes a class of human monoclonal antibodies which immunoreact with human platelets and the platelet glycoprotein gpIIb/IIIa. One set of antibodies were produced by the present methods in which a binding site in a CDR3 domain of an immunoglobulin heavy chain was designed to contain an RDG minimum recognition domain, as described in the Examples. Another set of preferred antibodies containing an RGD-dependent binding site were produced by the present methods for motif switching an existing binding site.

The resulting population of display vectors containing an RGD tripeptide in the display protein obtained by either of the methods of this invention were screened first for gpIIb/IIIa binding activity in an ELISA assay in which gpIIb/IIIa were in the solid phase to identify a population of display vectors which bound gpIIb/IIIa. Thereafter, selected members of the population of display vectors with gpIIb/IIIa binding activity were isolated, soluble Fab expression was engineered into each of the selected vectors as described in the Examples, and the resulting soluble Fab were expressed, and screened for binding or other functional activities.

Anti-gpIIb/IIIa human monoclonal antibodies were identified which have the desirable property of inhibiting gpIIb/IIIa function in platelets and other fibrinogen-gpIIb/IIIa ligand-receptor complex-mediated events, including inhibiting platelet aggregation and inhibiting thrombus formation. Data presented in the Examples illustrates anti-gpIIb/IIIa human monoclonal antibodies that are potent inhibitors of platelet aggregation at concentrations of about 1–100 nanomolar (nM). The human monoclonal antibody designated Mab IIb/IIIa-19 exhibited particularly high platelet aggregation inhibition $IC_{50}$ concentrations (concentration required for 50% inhibition of platelet aggregation). The human monoclonal antibody designated Fab 9 exhibited an affinity of $5 \times 1^{-9}$ M towards gpIIb/IIIa under the binding conditions reported in the Examples.

A preferred anti-gpIIb/IIIa human monoclonal antibody of this invention has the binding specificity of a monoclonal antibody comprising a heavy chain immunoglobulin variable region amino acid residue sequence selected from the group of binding site sequences consisting of IIb/IIIa-1, IIb/IIIa-17, IIb/IIIa-19, Fab 9, MTFIIb/IIIa-1, respectively, SEQ ID NOs 1–5, and MTFIIb/IIIa-5 (SEQ ID NO 4) and conservative substitutions thereof.

Particularly preferred human monoclonal antibodies are those having the immunoreaction (binding) specificity of a monoclonal antibody having heavy and light chain immunoglobulin variable region amino acid residue sequences in pairs (H:L) where the light chain is the light chain encoded by the plasmid vector pC3AP313 described herein, and referred to as light chain 313, or L313, and the heavy chain has one of the recited binding sites, and conservative substitutions thereof. The designation of a human monoclonal antibody with a colon, e.g., H:L313 is to connote a H:L pair formed by the heavy and light chain, respectively, in which the light chain is the preferred L313 light chain described herein.

b. Anti-vitronectin Receptor Antibodies

In one embodiment, the invention describes a class of human monoclonal antibodies which immunoreact with human vitronectin receptor (VnR) and cells that contain the receptor. The antibodies were produced by the present methods in which a binding site in a CDR3 domain of an immunoglobulin heavy chain was designed to contain an RDG minimum recognition domain, as described in the Examples.

The resulting population of display vectors containing an RGD tripeptide in the display protein were screened first for VnR binding activity in an ELISA assay in which either $\alpha_v\beta_3$ or $\alpha_v\beta_5$ were in the solid phase to identify a population of display phagemid vectors which bound the solid phase antigen. Thereafter, selected members of the population of display vectors with VnR binding activity were isolated, soluble Fab expression was engineered into each of the selected vectors as described in the Examples, and the resulting soluble Fab were expressed, and screened for binding or other functional activities.

Anti-VnR human monoclonal antibodies are thereby identified which have the desirable property of inhibiting VnR-mediated cell adhesion and cell motility, and tumor metastasis.

A preferred anti-VnR human monoclonal antibody of this invention has the binding specificity for $\alpha_v\beta_3$ or $\alpha_v\beta_5$, and more preferably is specific for one but not the other VnR species. The human monoclonal antibody designated Fab 9 is particularly preferred because it exhibited an affinity of $1 \times 1^{-10}$ M towards $\alpha_v\beta_3$ under the binding conditions reported in the Examples, and was substantially less immunoreactive with $\alpha_v\beta_5$.

Preferred antibodies which preferentially bind to $\alpha_v\beta_3$ include antibodies that include a sequence shown in SEQ ID NOs 4, 6, 7, 8 or 9. Preferred antibodies which preferentially bind to $\alpha_v\beta_5$ include antibodies that include a sequence shown in SEQ ID NOs 10 or 11.

Particularly preferred human monoclonal antibodies are those having the immunoreaction (binding) specificity of a monoclonal antibody having heavy and light chain immunoglobulin variable region amino acid residue sequences in pairs (H:L) where the light chain is the light chain encoded by the plasmid vector pC3AP313 described herein, and referred to as light chain 313, or L313, and the heavy chain has one of the recited binding sites, and conservative substitutions thereof. Particularly preferred are antibodies in which the heavy chain is derived from the plasmid pC3AP313.

Therefore, in preferred embodiments the antibody composition contains antibody molecules that bind the $\alpha_v\beta_3$ vitronectin receptor (VnR), and that contain the $\alpha_v\beta_3$-4, $\alpha_v\beta_3$-5 (Fab 9), $\alpha_v\beta_3$-7, $\alpha_v\beta_3$-8, $\alpha_v\beta_3$-10 or MTFVnRB3-3 binding site. One of the preferred antibody molecules, Fab 9, is unique in that it immunoreacts with both gpIIb/IIIa and $\alpha_v\beta_3$ but does not immunoreact with $\alpha_v\beta_5$ as described in the Examples. Particularly preferred are human monoclonal antibodies having the heavy and light chain coded by the vector pC3AP313, and wherein the heavy chain includes one of the above-recited binding sites in the CDR3 domain.

In another preferred embodiment, the antibody composition contains antibody molecules that bind the $\alpha_v\beta_5$ vitronectin receptor (VnR), and that contain the $\alpha_v\beta_5$-6 or $\alpha_v\beta_5$-11 binding site. Particularly preferred are human monoclonal antibodies having the heavy and light chain coded by the vector pC3AP313, and wherein the heavy chain includes one of the above-recited binding sites in the CDR3 domain.

c. Anti-HIV GP120 Human Monoclonal Antibody

Another preferred human monoclonal antibody produced by the present methods is prepared using the CD4 minimum recognition site described herein, and is screened and selected for binding to the V3 loop polypeptide of HIV gp120.

2. Non-RGD-Dependent Human Monoclonal Antibodies a. Anti-GPIIb/IIIA Human Monoclonal Antibodies In one embodiment, the invention describes a class of human monoclonal antibodies which immunoreact with human platelets and the platelet glycoprotein gpIIb/IIIa. One set of preferred antibodies that immunoreact with selected integrin receptors through an RGD-independent binding site were produced by the present methods for motif switching an existing binding site.

The resulting population of display vectors containing a newly engineered motif in place of the existing RGDI (SEQ ID NO 53) obtained by the motif switching method of this invention performed in an originally selected display protein were screened first for gpIIb/IIIa binding activity in an ELISA assay in which gpIIb/IIIa were in the solid phase to identify a population of display vectors which bound gpIIb/IIIa. Thereafter, selected members of the population of display vectors with gpIIb/IIIa binding activity were isolated, soluble Fab expression was engineered into each of the selected vectors as described in the Examples, and the resulting soluble Fab were expressed, and screened for binding or other functional activities.

Anti-gpIIb/IIIa human monoclonal antibodies were identified which have the desirable property of inhibiting gpIIb/IIIa function in platelets and other fibrinogen-gpIIb/IIIa ligand-receptor complex-mediated events, including inhibiting platelet aggregation and inhibiting thrombus formation. Data presented in the Examples illustrates anti-gpIIb/IIIa human monoclonal antibodies that are potent inhibitors of fibrinogen binding to the receptor at concentrations of about 1–100 nanomolar (nM). The human monoclonal antibody designated MTFIIb/IIIa-10 (MTF-10) also inhibited the binding of vitronectin to $\alpha_v\beta_3$ but it required $1\times10^{-7}$ M to only partially inhibit the binding. The human monoclonal antibody designated MTFIIb/IIIa-40 exhibited an affinity of about $1-4\times1^{-9}$ M towards gpIIb/IIIa, depending upon the assay conditions, and particularly depending upon the cation ($Ca^{2+}$ or $Mn^{2+}$). Similarly, MTF-32 exhibited an affinity of about $1-3\times1^{-9}$ M towards gpIIb/IIIa, depending upon the assay conditions, and particularly depending upon the cation. Antibody MTF-10 exhibited an affinity of about $7-8\times 1^{-9}$ M towards gpIIb/IIIa, depending upon the assay conditions and cation.

Insofar as the MTF series antibodies were produced by the methods of the present invention using Fab 9 as a starting material, it is noted that the resulting antibodies do not contain the "RGD" tripeptide in the resulting CDR region, although Fab 9 did contain an RGD motif. Thus, in one embodiment, a preferred monoclonal antibody, in its various forms, has a complementarity determining region amino acid residue sequence that does not contain the RGD sequence. The preparation of high affinity antibodies which lack the RGD sequence in the CDR is unexpected because (1) RGD is well known to be an important motif for ligand binding specificity to gpIIb/IIIa, (2) natural ligands of gpIIb/IIIa (e.g., fibrinogen) contain RGD, (3) the starting antibody Fab 9 used to prepare the MTF series antibodies contained RGD in its CDR domain, and (4) RGD-containing ligands competed with both Fab 9 and the MTF series antibodies for binding to gpIIb/IIIa.

A preferred anti-gpIIb/IIIa human monoclonal antibody of this invention has the binding specificity of a monoclonal antibody comprising a heavy chain immunoglobulin variable region amino acid residue sequence selected from the group of binding site sequences consisting of SEQ ID NOs 19–34 corresponding to the designated motif switched antibodies, and conservative substitutions thereof.

One preferred embodiment of the invention contemplates a human monoclonal antibody capable of immunoreacting with human platelet glycoprotein gpIIb/IIIa and inhibiting platelet aggregation, where the antibody immunoreacts with gpIIb/IIIa with an affinity of at least $1\times10^{-9}$ molar (M), and has a CDR sequence that does not contain the RGD sequence. 10 Particularly preferred in this embodiment is an anti-gpIIb/IIIa human monoclonal antibody having the binding specificity of a monoclonal antibody that comprises a heavy chain immunoglobulin variable region amino acid residue sequence that has the sequence characteristics of a sequence selected from the group of binding site sequences consisting of SEQ ID NOs 25, 32 and 34, and conservative substitutions thereof.

By the phrase "at least $1\times10^{-9}$ M" is meant that, when measured using standard immunoreaction association and dissociation rate measurements to determine binding affinity, the recited antibody has the specified affinity, and preferably a greater binding affinity, such as $5\times10^{-9}$ M, or even more ($1\times10^{-10}$ M). Immunoaffinity can be determined by any of a variety of methods, including standard radioimmuno assay, Skatchard analysis, surface plasmon resonance, and the like methods, some of which are described in the Examples.

Particularly preferred human monoclonal antibodies are those having the immunoreaction (binding) specificity of a monoclonal antibody having heavy and light chain immunoglobulin variable region amino acid residue sequences in pairs (H:L) where the light chain is the light chain encoded by the plasmid vector pC3AP313 described herein, and referred to as light chain 313, or L313, and the heavy chain has one of the recited binding sites, and conservative substitutions thereof. The designation of a human monoclonal antibody with a colon, e.g., H:L313 is to connote a H:L pair formed by the heavy and light chain, respectively, in which the light chain is the preferred L313 light chain described herein.

b. Anti-vitronectin Receptor Antibodies

In one embodiment, the invention describes a class of human monoclonal antibodies which immunoreact with human vitronectin receptor (VnR) and cells that contain the receptor. The antibodies that immunoreact with selected integrin receptors through an RGD-independent binding site were produced by the present methods for motif switching an existing binding site.

The resulting population of display vectors containing a newly engineered motif in place of the existing RGDI (SEQ ID NO 53) obtained by the motif switching method of this invention performed in an originally selected display protein were screened first for VnR binding activity in an ELISA assay in which either $\alpha_v\beta_3$ or $\alpha_v\beta_5$ were in the solid phase to identify a population of display phagemid vectors which bound the solid phase antigen. Thereafter, selected members of the population of display vectors with VnR binding activity were isolated, soluble Fab expression was engineered into each of the selected vectors as described in the Examples, and the resulting soluble Fab were expressed, and screened for binding or other functional activities.

Anti-VnR human monoclonal antibodies are thereby identified which have the desirable property of inhibiting VnR-mediated cell adhesion and cell motility, and tumor metastasis.

A preferred anti-VnR human monoclonal antibody of this invention has the binding specificity for $\alpha_v\beta_3$ or $\alpha_v\beta_5$, and more preferably is specific for one but not the other VnR species.

Particularly preferred human monoclonal antibodies are those having the immunoreaction (binding) specificity of a monoclonal antibody having heavy and light chain immunoglobulin variable region amino acid residue sequences in pairs (H:L) where the light chain is the light chain encoded by the plasmid vector pC3AP313 described herein, and referred to as light chain 313, or L313, and the heavy chain has one of the recited binding sites, and conservative substitutions thereof. Particularly preferred are antibodies in which the heavy chain is derived from the plasmid pC3AP313.

Therefore, in preferred embodiments the antibody composition contains antibody molecules that bind the $\alpha_v\beta_3$ vitronectin receptor (VnR), and that contain the motif switched human monoclonal antibodies having the amino acid residues sequences listed in SEQ ID NOs 13–18 corresponding to the designations described herein. One of the preferred antibody molecules, Fab 9, is unique in that it immunoreacts with both gpIIb/IIIa and $\alpha_v\beta_3$ but does not immunoreact with $\alpha_v\beta_5$ as described in the Examples. Particularly preferred are human monoclonal antibodies having the heavy and light chain coded by the vector pC3AP313, and wherein the heavy chain includes one of the above-recited binding sites in the CDR3 domain.

In another preferred embodiment, the antibody composition contains antibody molecules that bind the $\alpha_v\beta_5$ vitronectin receptor (VnR), and that contain the $\alpha_v\beta_3$-6 or $\alpha_v\beta_3$-11 binding site. Particularly preferred are human monoclonal antibodies having the heavy and light chain coded by the vector pC3AP313, and wherein the heavy chain includes one of the above-recited binding sites in the CDR3 domain.

I. Peptides Derived from Human Monoclonal Antibodies

Following the present invention, polypeptides having a desired binding activity have been produced using the present methods, and can be utilized in the form of an isolated polypeptide.

A polypeptide of the present invention comprises no more than about 100 amino acid residues, preferably no more than about 60 residues, more preferably no more than about 30 residues, and includes an amino acid residue sequence defining a binding site of the present invention. A polypeptide has the ability to bind with the ligand to which it was developed using the present mutagenesis and screening methods. A preferred polypeptide has the capacity to bind to the integrin $\alpha_{IIb}\beta_3$ or $\alpha_v\beta_3$.

In one embodiment the invention contemplates a polypeptide that includes an amino acid residue sequence that defines a binding site sequence derived from a monoclonal antibody of this invention. Insofar as a polypeptide is derived from the sequence of a monoclonal antibody with the ability to immunoreact with a preselected receptor, the polypeptide also binds to the preselected receptor, and can thereby function as an analog to the native ligand for the receptor.

In one embodiment, a polypeptide of this invention includes an amino acid residue sequence having the sequence characteristics of a sequence according to the formula: -CSFGRGDIRNC- (SEQ ID NO 12). Preferably, a polypeptide includes an amino acid residue sequence according to the formula: -VGCSFGRGDIRNCYYMDV- (SEQ ID NO 4) or -GSFGRGDIRNG- (SEQ ID NO 68). These polypeptides were derived from antibody Fab 9, and have the ability to inhibit vitronectin binding to purified vitronectin receptor $\alpha_v\beta_3$. A particularly preferred polypeptide has a sequence selected from the group consisting of CSFGRGDIRNC (SEQ ID NO 12), VGCSFGRGDIRNCYYMDV (SEQ ID No 4) and GSFGRGDIRNG (SEQ ID NO 68).

Thus, an exemplary polypeptide described herein was obtained from the binding site of a monoclonal antibody immunoreactive with the integrins $\alpha_{IIb}\beta_3$ or $\alpha_v\beta_3$.

In addition, polypeptides according to the formula -CSFGRNDSRNC- or -GCSFGRNDSRNCY-, shown in SEQ ID NOs 69 and 70, respectively, were obtained from the binding site of antibody MTF-40 described herein. Polypeptides including these sequences bind gpIIb/IIIa, and therefore can be used to inhibit platelet adhesion and/or fibrinogen binding to gpIIb/IIIa, and the functions accompanying binding.

Furthermore, polypeptides according to the formula -CSFGRTDQRNC- or -GCSFGRTDQRNCY-, shown in SEQ ID NOs 71 and 72, respectively, were obtained from the binding site of antibody MTF-32 described herein. Polypeptides including these sequences also bind gpIIb/IIIa, and therefore can be used to inhibit platelet adhesion and/or fibrinogen binding to gpIIb/IIIa, and the functions accompanying binding.

Although the amino acid residue sequences that flank the specified sequence may vary, in one embodiment, the preferred flanking sequences are those residues defining an immunoglobulin variable domain.

Polypeptides that bind to the integrins $\alpha_{IIb}\beta_3$ or $\alpha_v\beta_3$ described herein inhibit normal interactions between the integrin and their normal ligands. Thus, a polypeptide functions as an analog to the known ligands for the recited integrins. The polypetides can inhibit ligand binding to integrin both in vitro in standardized assay conditions and in vivo.

Methods to measure the inhibition of binding between ligand and integrin are conveniently carried out in vitro in a standardized ELISA binding. Exemplary assays are detailed in the Examples herein, and can be used to detect the presence of inhibition.

It should be understood that a subject polypeptide need not be identical to the amino acid residue sequence of the binding site of the monoclonal antibody from which it was derived, so long as it includes the required sequence and is able to inhibit the binding of ligand to integrin as described. Therefore, a polypeptide of this invention can have the sequence characteristics of a recited polypeptide, i.e., tolerate non-essential amino acid substitutions or modifications, so long as the polypeptide functions substantially the same, i.e., is substantially equivalent.

A subject polypeptide includes any analog, fragment or chemical derivative of a polypeptide whose amino acid residue sequence is shown herein so long as the polypeptide exhibits the expressed binding activity. Therefore, a present polypeptide can be subject to various changes, substitutions, insertions, and deletions where such changes provide for certain advantages in its use. In this regard, a polypeptide of this invention corresponds to, rather than is identical to, the sequence of the corresponding binding site where one or more changes are made and it retains its binding ability as defined herein.

The term "analog" includes any polypeptide having an amino acid residue sequence substantially identical to a sequence specifically shown herein in which one or more residues have been conservatively substituted with a functionally similar residue and which displays the binding ability as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A polypeptide is free of homoserine lactone when there is no detectable homoserine lactone present in the polypeptide when subjected to conventional amino acid analysis able to indicate the presence of homoserine lactone or other amino acids. Amino acid analysis methods suitable to detect homoserine lactone are generally well known in the art.

The term "fragment" refers to any subject polypeptide having an amino acid residue sequence shorter than that of a polypeptide whose amino acid residue sequence is shown herein.

When a polypeptide of the present invention has a sequence that is not identical to the sequence of antibody from which it was derived, it is typically because one or more conservative or non-conservative substitutions have been made, usually no more than about 30 number percent, and preferably no more than number percent of the amino acid residues are substituted.

"Substantially homologous" means that a particular subject sequence or molecule, for example, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous.

Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Additional residues may also be added at either terminus of a polypeptide of this invention for the purpose of providing a "linker" by which the polypeptides of this invention can be conveniently affixed to a label or solid matrix, or carrier.

Labels, solid matrices and carriers that can be used with the polypeptides of this invention are described hereinbelow.

Amino acid residue linkers are usually at least one residue and can be 40 or more residues, more often 1 to 10 residues, but do not form epitopes cross-reactive with the corresponding integrin. Typical amino acid residues used for linking are tyrosine, cysteine, lysine, glutamic and aspartic acid, or the like. In addition, a subject polypeptide can differ, unless otherwise specified, from the natural sequence of the corresponding antibody, the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W.H. Freeman Co., San Francisco, 1969; M. Bodanszky, et al., "Peptide Synthesis", John Wiley & Sons, Second Edition, 1976 and J. Neienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A polypeptide of this invention can be used in the therapeutic methods of this invention, inter alia, to inhibit the activity of the corresponding integrin where inhibition is desired. Particularly preferred is the use of the integrin-binding polypeptides as inhibitors of integrin function by blocking ligand binding.

A polypeptide can be prepared and utilized in both a linear or in a cyclized form. The preparation of cyclized polypeptides is discussed in the Examples.

J. Therapeutic Compositions

The present invention contemplates therapeutic compositions useful for practicing the therapeutic methods described herein. Therapeutic compositions of the present invention contain a physiologically tolerable carrier together with at least one species of human monoclonal antibody or polypeptide derived therefrom as described herein, dissolved or dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. Thus, an antibody molecule-containing composition can take the form of solutions, suspensions, tablets, capsules, sustained release formulations or powders, or other compositional forms.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol, and other solutes.

Liquid compositions can also contain liquid phases in addition to and to the exclusion of water.

Exemplary of such additional liquid phases are glycerin, vegetable oils such as cottonseed oil, organic esters such as ethyl oleate, and water-oil emulsions.

A therapeutic composition contains a human monoclonal antibody of the present invention, typically in an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

Preferably, an antibody-containing therapeutic composition typically contains about 10 microgram (ug) per milliliter (ml) to about 100 milligrams (mg) per ml of antibody as active ingredient per volume of composition, and more preferably contains about 1 mg/ml to about 10 mg/ml (i.e., about 0.1 to 1 weight percent).

A therapeutic composition in another embodiment contains a polypeptide of the present invention, typically in an amount of at least 0.1 weight percent of polypeptide per weight of total therapeutic composition. A weight percent is a ratio by weight of polypeptide to total composition. Thus, for example, 0.1 weight percent is 0.1 grams of polypeptide per 100 grams of total composition.

Preferably, an polypeptide-containing therapeutic composition typically contains about 10 microgram (ug) per milliliter (ml) to about 100 milligrams (mg) per ml of polypeptide as active ingredient per volume of composition, and more preferably contains about 1 mg/ml to about 10 mg/ml (i.e., about 0.1 to 1 weight percent).

K. Therapeutic Methods

In view of the benefit of using human monoclonal antibodies in vivo in human patients, the presently described antibodies are particularly well suited for in vivo use as a therapeutic reagent for blocking or inhibiting the function of the target molecule which the antibody binds. The peptides derived from the monoclonal antibodies described herein are also contemplated for use in the therapeutic methods of this invention. The method comprises contacting a sample believed to contain the target molecule with a composition comprising a therapeutically effective amount of a human monoclonal antibody or peptide of this invention which binds the target molecule.

For in viva modalities, the method comprises administering to the patient a therapeutically effective amount of a physiologically tolerable composition containing a human monoclonal antibody or peptide of the invention.

The dosage ranges for the administration of the monoclonal antibodies and peptides of the invention are those large enough to produce the desired effect in which the disease symptoms mediated by the target molecule are ameliorated. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

A therapeutically effective amount of a polypeptide of this invention is typically an amount of polypeptide such that when administered in a physiologically tolerable composition is sufficient to achieve a plasma concentration of from about 0.1 microgram (ug) per milliliter (ml) to about 100 ug/ml, preferably from about 1 ug/ml to about 10 ug/ml. Stated differently, the dosage can vary from about 0.1 mg/kg to about 300 mg/kg, and preferably from about 0.2 mg/kg to about 200 mg/kg, in one or more dose administrations daily, for one or several days.

The human monoclonal antibodies or polypeptides of the invention can be administered parenterally by injection or by gradual infusion over time. Although the target molecule can typically be accessed in the body by systemic administration and therefore most often treated by intravenous administration of therapeutic compositions, other tissues and delivery means are contemplated where there is a likelihood that the tissue targeted contains the target molecule. Thus, human monoclonal antibodies or polypeptides of the invention can be administered intravenously, intraperitoneally, intramuscularly, subcutaneously, intracavity, transdermally, and can be delivered by peristaltic means.

The therapeutic compositions containing a human monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

1. Methods for Inhibiting Platelet GpIIb/IIIa Function

An anti-gpIIb/IIIA human monoclonal antibody or peptide derived therefrom containing a gpIIB/IIIa-binding site can be used to in vivo or in vitro modulate the function of gpIIb/IIIa on platelets. For instance, the human monoclonal antibody or peptide can be used in a pharmaceutically acceptable composition that, when administered to a human subject in an effective amount, is capable of inhibiting the aggregation of platelets, and thereby decreasing the rate of thrombus formation. Thus, in vivo administration of an anti-gpIIb/IIIa human monoclonal antibody that inhibits platelet aggregation can be used in vivo to modulate any physiological response initiated by platelet adhesion, such as coagulation and some inflammatory responses.

When this method is carried out in vivo, an effective amount of an antibody or peptide composition containing a physiologically tolerable diluent and antibody molecules that immunoreact with gpIIb/IIIa and that inhibit platelet aggregation is intravenously administered to a mammal, and the mammal is maintained for a sufficient time period to allow the antibody molecules to immunoreact with any gpIIb/IIIa present and form an immunoreaction product and to allow the binding site containing the peptide to bind to gpIIb/IIIa and form a peptide-receptor complex such that the normal ligand can no longer bind to the receptor.

In preferred embodiments the antibody composition contains antibody molecules having a heavy chain that includes a binding site selected from the group consisting of SEQ ID NOs 1–5, and 19–34 and having the light chain L313. Particularly preferred are the monoclonal antibodies when expressed in the vector pC3AP313. In preferred embodiments, the peptide composition for inhibiting platelet aggregation includes a polypeptide sequence selected from the group consisting of SEQ ID NOs 12, 69, 70, 71 and 72, and conservative substitutions thereof.

2. Methods for Inhibiting HIV Gp120-mediated Events

The present invention describes in one embodiment a method for providing passive immunotherapy to HIV disease in a human comprising administering to the human an immunotherapeutically effective amount of an anti-HIV gp120 envelope glycoprotein monoclonal antibody of this invention.

A representative patient for practicing the present passive immunotherapeutic methods is any human exhibiting symptoms of HIV-induced disease, including AIDS or related conditions believed to be caused by HIV infection, and humans at risk of HIV infection. Patients at risk of infection by HIV include babies of HIV-infected pregnant mothers, recipients of transfusions known to contain HIV, users of HIV contaminated needles, individuals who have participated in high risk sexual activities with known HIV-infected individuals, and the like risk situations.

In one embodiment, the passive immunization method comprises administering a composition comprising more than one species of anti-HIV gp120 human monoclonal antibody of this invention, preferably directed to non-competing epitopes or directed to distinct serotypes or strains of HIV, as to afford increased effectiveness of the passive immunotherapy.

A therapeutically (immunotherapeutically) effective amount of a human monoclonal antibody is a predetermined amount calculated to achieve the desired effect, i.e., to neutralize the HIV present in the sample or in the patient, and thereby decrease the amount of detectable HIV in the sample or patient. In the case of in vivo therapies, an effective amount can be measured by improvements in one or more symptoms associated with HIV-induced disease occurring in the patient, or by serological decreases in HIV antigens.

In preferred embodiments the antibody composition contains antibody molecules expressed by the plasmid pC3AP313.

3. Methods for Inhibiting Vitronectin Receptor-mediated Events

An anti-vitronectin receptor human monoclonal antibody of this invention can be used to in vivo or in vitro to modulate the function of vitronectin receptor present on a variety of cells.

The receptor for vitronectin (VnR) has been identified to be any one of the integrin heterodimers referred to as $\alpha_v\beta_3$ or $\alpha_v\beta_5$. Cell adhesion to vitronectin is therefore mediated by VnR, and it has been determined that VnR-mediated adhesion is particularly important in tumor cell adhesion, migration and tumor metastases. See, for example, Leavesly et al., *J. Cell Biol.*, 117:1101–1107 (1992). Thus, inhibition of vitronectin interaction with VnR will perturb cell attachment events associated with vitronectin, and will thereby block VnR-mediated events such as tumor cell adhesion and migration.

Therefore, the invention also contemplates the use of an anti-VnR human monoclonal antibody or peptide-derived therefrom containing a VnR binding site in a pharmaceutically acceptable composition that, when administered to a human subject in an effective amount, is capable of inhibiting VnR binding to vitronectin, and thereby decreasing malignant cell adhesion and c ell migration. Thus, in vivo administration of an anti-VnR human monoclonal antibody or a VnR-specific peptide that inhibits metastatic cell adhesion and migration can be used in vivo to modulate any physiological response mediated by vitronectin binding to VnR, such as tumor cell attachment, and metastases.

When this method is carried out in vivo, an effective amount of an antibody or peptide composition respectively containing a physiologically tolerable diluent and antibody or peptide molecules that immunoreact with VnR and that inhibit tumor cell migration is intravenously administered to a mammal, and the mammal is maintained for a sufficient time period to allow the antibody molecules or peptides to immunoreact with any VnR present and form an immunoreaction product or a peptide/receptor complex.

In preferred embodiments the antibody composition contains antibody molecules that bind the $\alpha_v\beta_3$ vitronectin receptor (VnR) containing the binding sites described herein and in SEQ ID NOs 4, 6, 7, 8, 9, and 13–18. Particularly preferred are human monoclonal antibodies having the heavy and light chain coded by the vector pC3AP313, and wherein the heavy chain includes one of the above-recited binding sites in the CDR3 domain.

In a related preferred embodiment, the antibody composition contains antibody molecules that bind the $\alpha_v\beta_5$ vitronectin receptor (VnR), and that contain the binding sites listed in SEQ ID NOs 10 and 11. Particularly preferred are human monoclonal antibodies having the heavy and light chain coded by the vector pC3AP313, and wherein the heavy chain includes one of the above-recited binding sites in the CDR3 domain.

In other preferred embodiments, a polypeptide composition for inhibiting vitronectin binding to VnR includes a polypeptide having a sequence characteristic of a sequence selected from the group consisting of SEQ ID NOs 4, 12, and 68, and conservative substitutions thereof.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Preparation of Synthetic Binding Sites Within the Heavy Chain CDR3 Domain of a Phagemid Fab Display Protein Produced by a Dicistronic Expression Vector A. Preparation of Nucleotide Sequences for Encoding Synthetic Binding sites Containing the Peptide, Arginine-Glycine-Aspartic Acid (RGD)

The immunoglobulin gene phagemid expression vector, pMT12, containing the heavy and light chain sequences for expressing the soluble form of an antibody was used to prepare the synthetic binding site proteins containing the peptides, arginine-glycine-aspartic acid (RGD), of this invention as described below in Example 1A1). The phagemid Fab display of an RGD peptide is one of the preferred binding sites prepared by the methods of this invention. The term "binding site" as defined herein is any region of a protein or polypeptide that participates in protein-target molecule interactions. In the context of an RGD binding site, integrin receptors which bind RGD are contemplated as target molecules. For a review of RGD-dependent integrin receptors, see Ginsberg et al., *TIBS*, 16:246–250 (1991).

The RGD sequence has been shown to occur in 4 known structures, shake venom "disintegrins" kistrin, echistatin, tenascin and the foot and mouth disease virus. In each of these structures, RGD is found in an extended flexible loop at the apex of the turn. The simple RGD motif is insufficient for high affinity binding to RGD-specific receptors such as $\alpha_v/\beta_3$ and gpIIb/IIIa. Binding is dependent on the correct conformational display of the motif as evidenced by perturbations in affinity of peptides as a function of flanking sequences and conformational constraint conferred by cyclization. Simple placement of the RGD motif within a complementary determining region (CDR) of a variable region of an antibody thus would be insufficient to confer binding with a useful affinity and specificity. For example, a natural antibody containing a RGD motif at the C-terminal portion of the heavy chain CDR3 failed to bind the vitronectin or gpIIb/IIIa integrin receptors. Therefore, this invention has provided for the methods to oligonucleotides that result in the positioning of a RGD motif at the apex of an extended loop in the heavy chain CDR3 with flanking regions that conformationally optimize the display of the motif.

The binding sites of this invention as described herein thus were incorporated into a CDR in the antibody heavy chain of pMT12. The preparation and characterization of the pMT12 phagemid expression vector containing heavy and light chain sequences for the expression of human monoclonal antibodies has been described by Burton et al., *Proc. Natl. Acad. Sci., USA*, 88:10134–10137 (1991), the disclosure of which is hereby incorporated by reference.

The *E. coli* bacterial cells containing pMT12 soluble Fab-producing phagemids were deposited on Sep. 30, 1992, with the American Type Culture Collection, 1301 Parklawn Drive, Rockville, Md., USA (ATCC). The deposit of the plasmid-containing cells is listed under the name MT12 and has been assigned the ATCC designation number 69079. This deposit was made under the provisions of the Budapest Treaty on the International Recognition of the Deposit of Microorganisms for the Purpose of Patent Procedure and the Regulations thereunder (Budapest Treaty).

The phagemid pMT12 was used in polymerase chain reaction (PCR) amplifications to create unique binding sites within the CDR3 of the Fab heavy chain in the phagemid. This human antibody was chosen as the presenting scaffold as it was produced efficiently in *E. coli* and had an extended heavy chain CDR3 consisting of 18 instead of 16 amino acid residues. Residues at the amino and carboxy terminal portion of the heavy chain CDR3 were maintained so as to retain the stem of the extended hair-pin loop. The RGD motif was introduced at Kabat positions 100a–c ensuring its placement hear the apex of the turn.

For the PCR amplification, the 5' end of the heavy chain beginning at framework 1 and extending to the 3' end of CDR3 was amplified with two oligonucleotide primers. The position of the heavy chain CDR3 of pMT12 corresponds to Kabat numbers 94–103. For preparing a synthetic RGD-containing binding site of this invention, a pool of oligonucleotide primers shown below were synthesized with the complementary sequence for encoding the RGD peptide bordered by a degenerate region ((NNK)$_3$ where K is G or T and N is A, C, G or T) that encoded 3 amino acids on both sides of the RGD sequence. This region was further bordered by the nucleotide sequence for encoding the 5' and 3' CDR3 amino acid residues present in the pMT12 expression vector. Also contemplated for use in the methods of this invention for incorporating the RGD binding site into the CDR3 is an oligonucleotide having the complementary sequence to the RGD primer described below. One having ordinary skill in the art can design complementary oligonucleotides that will allow for the amplification of the same RGD-containing CDR3 in pMT12 as described below.

Amplification products resulting from the procedure as described below had sequences for encoding an RGD peptide bordered by sequences for randomly encoding 3 amino acids in the CDR3 region. The sequence NNK represents the coding strand sequence having the complementary sequence NNM in the primer as read from the 3' to 5' direction. Thus, in the primer as listed below the noncoding strand sequence is MNN as read in the 5' to 3' direction. The coding triplet sequence NNK was designed to prevent the production of deleterious stop codons. The only stop codon that could result from the expression of NNK would be an amber mutation that is suppressed when the phagemid is expressed an amber-suppressing host cell.

The PCR reaction resulted in the amplification of the region of the heavy chain fragment in the pMT12 phagemid vector clone beginning at framework region 1 (FR1) and extending to the end of the CDR3 domain which is approximately 450 base pairs (bp) in length. To amplify this region, the following primer pairs were used. The 5' oligonucleotide primer, FTX3, having the nucleotide sequence 5' GCAATTAACCCTCACTAAAGGG3' (SEQ ID NO 54), hybridized to the noncoding strand of the heavy chain corresponding to the region 5' of and including the beginning of FR1. The 3' oligonucleotide primer, RGD, having the nucleotide sequence 5' CTCCTCCTCCTCCTCGACGTC-CCATATAATAATTMNNMNNMNNATCGCCACG MNNMNNMNNTGGCCCCACTCTCGCACAATAATA3' (SEQ ID NO 49) where M is A or C and N is A, C, G or T, hybridized to the coding strand of the heavy chain corresponding to CDR3. The oligonucleotide primers were synthesized by operon Technologies, Alameda, Calif. The expected amino acid residue sequences in the CDR3 and flanking framework regions resulting from the PCR amplification with the 3' primer above have the formula: -NH$_2$-YYCARVGPXXXRGDXXXNYYMDVEEEEE-COOH (SEQ ID NO 55), where X is Xaa, any amino acid. Refer to the Table of Correspondence and the Sequence Listing for the identification of the amino acid residues presented in single letter format.

The PCR reaction was performed in a 100 microliter (ul) reaction containing one microgram (ug) of each of oligonucleotide primers FTX3 and RGD, 8 ul 2.5 millimolar (mM) dNTP's (dATP, dCTP, dGTP, dTTP), 1 ul TAQ POLYMERASE (Perkin-Elmer Corp., Norwalk, Conn.) 10 nanograms (ng) of template pMT12, and 10 ul of 10× PCR buffer purchased commercially (Perkin-Elmer Corp.). Thirty-five rounds of PCR amplification in a Perkin-Elmer Cetus 9600 GeneAmp PCR System thermocycler were then performed. The amplification cycle consisted of denaturing at 94 degrees C. (94 C) for one minute, annealing at 47 C for one minute, followed by extension at 72 C for two minutes. To obtain sufficient quantities of amplification product, 15 identical PCR reactions were performed.

The resultant PCR amplification products containing the sequence for encoding an RGD peptide were then gel purified on a 1.5% agarose gel using standard electroelution techniques as described in "Molecular Cloning: A Laboratory Manual", Sambrook et al., eds., Cold Spring Harbor, N.Y. (1989). Briefly, after gel electrophoresis of the digested PCR amplified Fab-display encoding synthetic binding sites, the region of the gel containing the DNA fragments of predetermined size was excised, electroeluted into a dialysis membrane, ethanol precipitated and resuspended in buffer containing 10 millimolar (mM) Tris-HCl [Tris (hydroxymethyl)aminomethane-hydrochloride] at pH 7.5 and 1 mM EDTA (ethylenediaminetetraacetic acid) to a final concentration of 50 nanograms/milliliter (ng/ml).

The purified RGD-expressing PCR products were then digested with the restriction enzymes XhoI and AatII to form a heavy chain antibody fragment for directional ligation into a similarly digested phagemid expression vector, designated pC3AP313, for the surface display of the expressed antibodies containing the newly created synthetic binding sites. The surface display phagemid expression vector, pC3AP313, has been deposited with ATCC on Feb. 2, 1993 for use in this invention. The deposited vector has been assigned the ATCC accession number 75408. The PC3AP313 expression vector containing the coat protein encoded by bacteriophage gene 3 was prepared as described in Example 2. The ligation procedure in creating expression vector libraries and the subsequent expression of the synthetic binding site-containing antibodies is performed as described in Example 2.

B. Preparation of Nucleotide Sequences Encoding Cyclized Synthetic Binding Sites Containing the Peptide, Arginine-Glycine-Aspartic Acid (RGD)

For preparing a cyclized version of the synthetic RGD-containing binding site within CDR3 of a human Fab antibody of this invention, a pool of oligonucleotide primers shown below were synthesized with the sequence encoding the RGD peptide bordered by a coding strand degenerate region ((NNK)$_3$ where K is G or T and N is A, C, G or T) for encoding 3 amino acids on both sides of the RGD sequence. This region was further bordered by the nucleotide sequence for encoding the 5' and 3' CDR3 amino acid residues in the pMT12 expression vector. The resulting amplification products had sequences for encoding an RGD peptide bordered by sequences for randomly encoding 3 amino acids in the CDR3 region further bordered by sequences for encoding cysteine residues to provide for an intra-loop disulfide linkage around the RGD synthetic binding site. This thereafter enabled the sequences to be directly synthesized using standard peptide methodology and cyclized to provide for the conformationally correct peptide.

The PCR reaction resulted in the amplification of the region of the heavy chain fragment in the pMT12 phagemid vector clone beginning at framework region 1 (FR1) and extending to the end of the CDR3 domain which is approximately 450 base pairs (bp) in length. To amplify this region, the following primer pairs were used. The 5' oligonucleotide primer, FTX3, having the nucleotide sequence 5' GCAATTAACCCTCACTAAAGGG3' (SEQ ID NO 54), hybridized to the noncoding strand of the heavy chain corresponding to the region 5' of and including the beginning of FR1. The 3' oligonucleotide primer, RGDC2, having the nucleotide sequence 5' CTCCTCCTCCTCGACGTCCATATAATAGCAMNNMNNMNNATCGCCACGM NNMNNMNNGCACCCCACTCTCGCACAATAATA3' (SEQ ID NO 50) where M is A or C and N is A, C, G or T, hybridized to the coding strand of the heavy chain corresponding to CDR3. The oligonucleotide primers were synthesized by Operon Technologies, Alameda, Calif. The expected amino acid residue sequences in CDR3 and flanking framework regions resulting from the PCR amplification with the 3' primer have the formula: -NH$_2$-YYCARVGCXXXRGDXXXCYYMDVEEEEE-COOH (SEQ ID NO 56), where X is Xaa, any amino acid. Refer to the Table of Correspondence and the Sequence Listing for the identification of the amino acid residues presented in single letter format.

The PCR reaction was performed as described in Example 1A. The resultant PCR products were purified, digested with XhoI and AatII and inserted into the similarly digested pC3AP313 surface display expression vector for preparation of an expression library as described in Example 2.

C. Preparation of Nucleotide Sequences Encoding Synthetic Binding Sites Containing the Binding Site on CD4 that is Specific for the HIV Glycoprotein gp120

The binding site of the HIV glycoprotein, gp120, on CD4 has been suggested to reside within the amino acid residues of 37 to 49 on CD4. These residues were amplified into CDR3 of the heavy chain in the pC3AP313 surface display expression vector to form a synthetic binding site within CDR3 of a human Fab antibody that would be recognized by gp120. The library of clones produced as described in Example 2 were then selected or screened for binding to gp120.

For preparing the binding site residues on CD4 specific for gp120, a pool of oligonucleotide primers shown below were synthesized with the complementary sequence encoding the CD4 amino acid peptide bordered by a coding strand degenerate region ((NNK)$_3$ where K is G or T and N is A, C, G or T) for encoding 5 amino acids on the amino terminal side of the CD4 sequence and 3 amino acids on the carboxy terminal side of the CD4 sequence. This region was further bordered by the nucleotide sequence for encoding the 5' and 3' CDR3 amino acid residues in the pC3AP313 expression vector. The resulting amplification products had sequences for encoding the CD4 sequences specific for binding to gp120 bordered by sequences for randomly encoding 3 amino acids in CDR3.

The PCR reaction resulted in the amplification of the region of the heavy chain fragment in the pC3AP313 phagemid vector clone beginning at framework region 1 (FR1) and extending to the end of the CDR3 which is approximately 450 base pairs (bp) in length. To amplify the heavy chain region in PC3AP313, the following primer pairs were used. The 5' oligonucleotide primer, FTX3, having the nucleotide sequence 5' GCAATTAACCCTCACTAAAGGG3' (SEQ ID NO 54), hybridized to the noncoding strand of the heavy chain corresponding to the region 5' of and including the beginning of FR1. The 3' oligonucleotide primer, CD4, having the nucleotide sequence 5' CTCCTCCTCCTCGACGTCMNNMNNMNNCA-GAAAACTCCCTTGATTACCM NNMNNMNNMN-NMNNACCTCTCGCACAGTAATACACGGC3' (SEQ ID NO 57) where M is A or C and N is A, C, G or T, hybridized to the coding strand of the heavy chain corresponding to CDR3. The oligonucleotide primers were synthesized by Operon Technologies Alameda, Calif. The expected encoded amino acid residue sequences in CDR3 and flanking framework regions resulting from the PCR amplification with the 3' primer have the formula: -NH$_2$-AVYYCARGXXXXXGNQGSFLXXXDVEEEEE-COOH (SEQ ID NO 58), where X is Xaa, any amino acid. Refer to the Table of Correspondence and the Sequence Listing for the identification of the amino acid residues presented in single letter format.

The PCR reaction was performed as described in Example 1A. The resultant PCR products were purified, digested with XhoI and AatII and inserted back into the similarly digested pC3AP313 surface display expression vector for preparation of an expression library as described in Example 2.

D. Preparation of Motif Switched CDR3 Synthetic Binding Sites that Bind Integrins Since the study of integrin function is complicated by native ligands that are difficult to work with and often yield data that are difficult to interpret, high affinity, well behaved, integrin ligands have been designed in this invention. The first step in this process was accomplished by building a synthetic human antibody to target the integrin ligand binding site as described in the Examples above. The target integrin was a because of its therapeutic importance in tumor metastasis and osteoporosis.

As described in Examples 1A and 1B, Fab antibodies were engineered to bind integrin $\alpha_v\beta_3$ using a semi-synthetic strategy that involved the insertion of an RGD motif into the sequence of the heavy chain CDR3 of a human antibody. A schematic representation of this process is shown in FIG. 1. In this case, the parent antibody bound to the HIV coat protein gp120. The RGD motif inserted into this CDR was loosely based on the "disintegrin" motif present in numerous snake venoms where the RGD is at the apex of a disulfide bonded loop. By incorporating a similar motif into a phage library where the six residues flanking the RGD sequence were randomized, a series of antibodies were obtained by panning this library on purified $\alpha_v\beta_3$. Interestingly, these semi-synthetic, RGD-containing antibodies bind $\alpha_v\beta_3$ nearly 1000-fold better than $\alpha_v\beta_5$, and $\alpha_5\beta_1$. However, in ligand inhibition studies the selected antibodies did not distinguish the two $\beta_3$-containing integrins, $\alpha_v\beta_3$ and $\alpha_{IIb}\beta_3$. Consequently, this invention contemplates the use of the methods as described herein to generate Fab antibodies that exhibit specificity for each of the two $\beta_3$ integrins.

As shown herein, antibody specificity for the ligand binding site of platelet integrin $\alpha_{IIb}\beta_3$ was obtained through an engineering strategy referred to as "motif optimization" or "motif switching". The backbone structure of one of the previous RGD-containing antibodies, Fab 9, was used as a scaffold because of its high affinity for the $\beta_3$-integrins. The positions corresponding to adhesion motif amino acid residue positions 5–8 in the heavy chain CDR3 (FIG. 1), that replaces the RGDI amino acid residue sequence in HCDR3 of Fab 9 (SEQ ID NO 4 from position number 7 to 10), were randomized. Optimal binding motifs specific for $\alpha_{IIb}\beta_3$ were selected by panning the new phage library on purified $\alpha_{IIb}\beta_3$, also referred to as gpIIb/IIIa, as described in Example 3. As shown below, the selected antibodies do not contain the RGD sequence, but all still block function, i.e., the binding of ligands to gpIIb/IIIa. These synthetic anti-integrin antibodies have great promise for simplifying the study of the integrin ligand binding pocket and also for inhibiting platelet activity in vivo. Since peptide ligands for many other integrins have been identified, the methods of this invention are useful for synthesizing highly specific antibodies that bind the ligand binding pocket of other members of this protein family.

In order to obtain antibodies that exhibited a higher affinity to the selected receptors and have greater sequence heterogeneity, a second cycle of mutagenesis was performed on a RGD-containing monoclonal antibody obtained as described in Example 1B. For this mutagenesis procedure, referred to as CDR motif switching or motif optimization, Fab 9 (SEQ ID NO 4) that exhibited the highest affinity towards $\alpha_v/\beta_3$ and gpIIb/IIIa was selected as the motif scaffold for incorporating new binding sites.

An oligonucleotide was designed for use in PCR amplification of the Fab 9 heavy chain that would result in the mutagenesis of the amino acid residue sequence in Fab 9, RGDI, beginning at position 7 and ending at position 10 in SEQ ID NO 4. This region corresponded to amino acid residue 5–8 in the heavy chain CDR3 as shown in FIG. 1. Thus, the oligonucleotide was randomized for 12 nucleotides with the triplet codon sequence MNN. The complementary nucleotide would contain the triplet codon NNK written in the 5' to 3' direction. The oligonucleotide as shown below was also designed to retain the nucleotide sequence bordering the RGDI sequence such that the resulting motif switched antibodies would only contain mutations in the RGDI site and not in the flanking regions. In addition, the oligonucleotide contained sequences that were from the framework 3 and 4 regions bordering the heavy chain CDR3 to maintain that portion of the nucleotide sequence of Fab 9.

Thus, for preparing motif optimized binding sites within CDR3 of a human Fab antibody of this invention, specifically Fab 9, a pool of oligonucleotide primers shown below were synthesized with a coding strand degenerate region ((NNK)$_3$ where K is G or T and N is A, C, G or T) for encoding 4 mutated amino acids flanked by Fab 9 CDR3 amino acid sequences as listed in SEQ ID NO 4. This region was further bordered by the nucleotide sequence for encoding the flanking amino acid residues in the pMT12 expression vector that was present in Fab 9.

The PCR reaction resulted in the amplification of the region of the heavy chain fragment in the pMT12 phagemid vector clone beginning at framework region 1 (FR1) and extending to the end of the CDR3 domain which is approximately 450 base pairs (bp) in length. To amplify this region, the following primer pairs were used. The 5' oligonucleotide primer, FTX3, having the nucleotide sequence 5' GCAAT-TAACCCTCACTAAAGGG3' (SEQ ID NO 54), hybridized to the noncoding strand of the heavy chain corresponding to the region 5' of and including the beginning of FR1. The 3' oligonucleotide primer, MOTIF, having the nucleotide sequence 5' CTCCTCCTCCTCCTCGACGTC-CATATAATAGCAATTCTMNNMNNMNNMNNC CCAAACGAGCACCCCACTCTCGCACAATAATA3' (SEQ ID NO 52) where M is A or C and N is A, C, G or T, hybridized to the coding strand of the heavy chain corresponding to the CDR3 Fab 9. The oligonucleotide primers were synthesized by Operon Technologies, Alameda, Calif. The expected encoded amino acid residue sequences in CDR3 resulting from the PCR amplification with the 3' primer have the formula: -NH$_2$-VGCSFGXXXXRNCYYMDV-COOH (SEQ ID NO 67), where X is Xaa, any amino acid. Refer to the Table of Correspondence and the Sequence Listing for the identification of the amino acid residues presented in single letter format.

The PCR reaction was performed as described in Example 1A. The resultant PCR products were purified, digested with XhoI and AatII and inserted into the similarly digested pC3AP313 surface display expression vector for preparation of an expression library as described in Example 2. The amino acid residue sequences resulting from the selection of motif switch CDR3 antibodies of this invention are described below in Examples 4 and 5 and are listed in the Section entitled "Binding Site Polypeptides".

2. Production of Phagemid Fab-displayed Synthetic Binding Sites

In practicing this invention to obtain expression of Fab-display proteins containing a synthetic binding site on a phage surface, the heavy (Fd consisting of $V_H$ and $C_H1$) and light (kappa) chains ($V_L$, $C_L$) of antibodies were first targeted to the periplasm of *E. coli* for the assembly of heterodimeric Fab molecules.

In this system, the first cistron encoded a periplasmic secretion signal (pelB leader) operatively linked to the fusion protein, Fd-cpIII. The second cistron encoded a second pelB leader operatively linked to a kappa light chain. The presence of the pelB leader facilitated the coordinated but separate secretion of both the fusion protein containing the synthetic binding site and light chain from the bacterial cytoplasm into the periplasmic space.

In this process, each chain was delivered to the periplasmic space by the pelB leader sequence, which was subsequently cleaved. The heavy chain containing the synthetic binding was anchored in the membrane by the cpIII membrane anchor domain while the light chain was secreted into the periplasm. Fab molecules were formed from the binding of the heavy chain with the soluble light chains.

Figure 2:
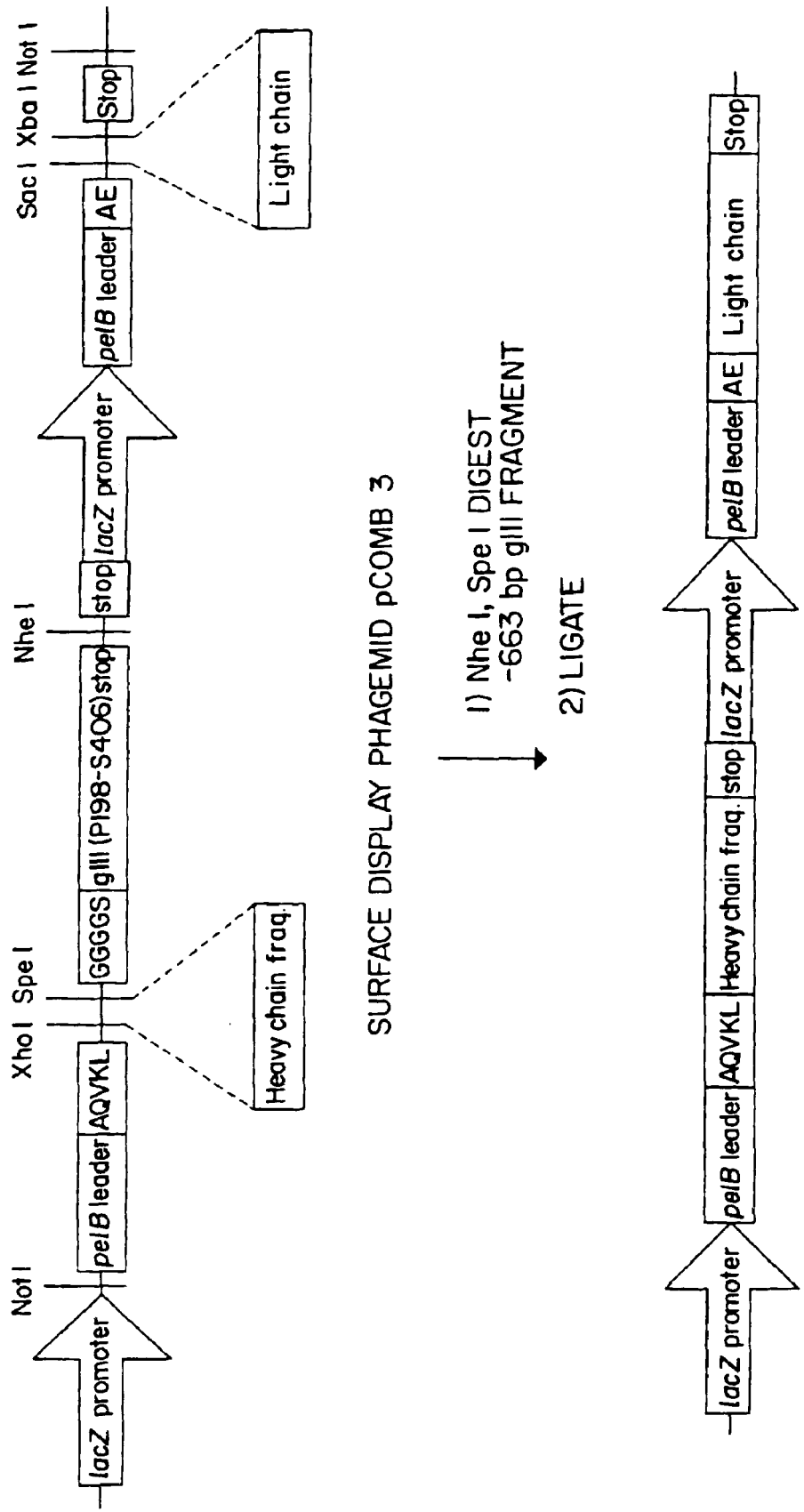

A. Preparation of a Dicistronic Expression Vector, pComb3, Capable of Expressing a Phagemid Fab Display Protein A schematic of the pComb3 phagemid expression vector for use in expressing the synthetic binding site-containing antibodies of this invention is shown in FIG. 2. The antibody Fd chain comprising variable ($V_H$) and constant ($C_H1$) domains of the heavy chain were fused with the C-terminal domain of bacteriophage gene III (3) coat protein. Gene III of filamentous phage encodes a 406-residue minor phage coat protein, cpIII (cp3), which is expressed prior to extrusion in the phage assembly process on a bacterial membrane and accumulates on the inner membrane facing into the periplasm of *E. coli*.

The phagemid vector, designated pComb3, allowed for both surface display and soluble forms of Fabs. The vector was designed for the cloning of combinatorial Fab libraries. The XhoI and SpeI site were provided for cloning complete PCR-amplified heavy chain (Fd) sequences consisting of the region beginning with framework 1 and extending through framework 4. An AatII restriction site is also present but not identified in FIG. 2. The presence of the AatII site allows for the insertion of XhoI/AatII digests of the PCR products prepared in Example 1 that contain sequences beginning with framework 1 and extending to the end of the CDR3 domain in which the sequences for encoding the synthetic binding sites are located. The insertion of an XhoI/AatII digest into pC3AP313 results in the fusion of the insert with the framework 4 domain in the pC3AP313 vector. Thus, the insertion results in the in-frame ligation of a complete heavy chain fragment consisting of PCR amplified framework 1 through CDR3 and retained pC3AP313 retained framework 4. The SacI and XbaI sites were provided for cloning PCR amplified antibody light chains. The cloning sites were compatible with previously reported mouse and human PCR primers as described by Huse et al., *Science*, 246:1275–1281 (1989) and Persson et al., *Proc. Natl. Acad. Sci., USA*, 88:2432–2436 (1991). The nucleotide sequence of the pelB, a leader sequence for directing the expressed protein to the periplasmic space, was as reported by Huse et al., supra.

The vector also contained a ribosome binding site as described by Shine et al., *Nature*, 254:34 (1975). The sequence of the phagemid vector, pBluescript, which includes ColE1 and F1 origins and a beta-lactamase gene, has been previously described by Short et al., *Nuc. Acids Res.*, 16:7583–7600 (1988) and has the GenBank Accession Number 52330 for the complete sequence. Additional restriction sites, SalI, AccI, HincII, ClaI, HindIII, EcoRV, PstI and SmaI, located between the XhoI and SpeI sites of the empty vector were derived from a 51 base pair stuffer fragment of pBluescript as described by Short et al., supra.

A nucleotide sequence that encodes a flexible 5 amino acid residue tether sequence which lacks an ordered secondary structure was juxtaposed between the Fab and cp3 nucleotide domains so that interaction in the expressed fusion protein was minimized.

Thus, the resultant combinatorial vector, pComb3, consisted of a DNA molecule having two cassettes to express one fusion protein, Fd/cp3, and one soluble protein, the light chain. The vector also contained nucleotide residue sequences for the following operatively linked elements listed in a 5' to 3' direction: a first cassette consisting of LacZ promoter/operator sequences; a NotI restriction site; a ribosome binding site; a pelB leader; a spacer region; a cloning region bordered by 5' XhoI and 3' SpeI restriction sites; the tether sequence; the sequences encoding bacteriophage cp3 followed by a stop codon; a NheI restriction site located between the two cassettes; a second lacZ promoter/operator sequence followed by an expression control ribosome binding site; a pelB leader; a spacer region; a cloning region bordered by 5' SacI and a 3' XbaI restriction sites followed by expression control stop sequences and a second NotI restriction site.

In the above expression vector, the Fd/cp3 fusion and light chain proteins were placed under the control of separate lac promoter/operator sequences and directed to the periplasmic space by pelB leader sequences for functional assembly on the membrane. Inclusion of the phage F1 intergenic region in the vector allowed for the packaging of single-stranded phagemid with the aid of helper phage. The use of helper phage superinfection allowed for the expression of two forms of cp3. Consequently, normal phage morphogenesis was perturbed by competition between the Fd/cp3 fusion and the native cp3 of the helper phage for incorporation into the virion. The resulting packaged phagemid carried native cp3, which is necessary for infection, and the encoded Fab fusion protein, which is displayed for selection. Fusion with the C-terminal domain was necessitated by the phagemid approach because fusion with the infective N-terminal domain would render the host cell resistant to infection.

The pComb3 expression vector described above forms the basic construct of pC3AP313, p7EIII, and pMT12 Fab display phagemid expression vectors used in this invention for the production of human Fab antibodies containing synthetic binding sites. The pC3AP313 and p7EIII phagemid expression vectors described in Example 1 having the respective ATCC accession numbers, 75408 and 75409, are pComb3-based vectors containing heavy and light chain sequences for encoding human Fab antibodies against tetanus toxin. The pMT12 phagemid expression vector, while based on pComb3, has been digested with NheI and SpeI to delete the sequence that encodes the bacteriophage coat protein 3, thereby resulting in the expression of soluble human anti-gp120 Fab. The pMT12 phagemid was deposited with ATCC in a bacterial host and has the accession number 69079.

B. Preparation of Expression Vector Libraries for the Expression of the Phagemid Fab-display Proteins 1) Phagemid Library Construction In order to obtain expressed human Fab antibodies having both heavy and light chain fragments, phagemid libraries were constructed. The libraries provided for the expression of recombinant human Fab antibodies having heavy and light chains where the synthetic binding sites of this invention are displayed in the heavy chain CDR3. The PCR products resulting from each of the amplification reactions prepared in Example 1 were separately inserted into a phagemid expression vector to prepare phagemid libraries.

As described below, the resultant gel purified heavy chain PCR fragments prepared in Examples 1A–1D were digested with the restriction enzymes and separately ligated into the pC3AP313 phagemid expression vector that was similarly digested.

For preparation of phagemid libraries for expressing the PCR products prepared in Examples 1A–1D, the PCR products were separately digested with XhoI and AatII and separately ligated with a similarly digested pC3AP313 phagemid expression vector prepared as described in Examples 1 and 2A. The ligation resulted in operatively linking the framework 1 through CDR3 PCR products with the framework 4 domain present in the pC3AP313 vector.

Phagemid libraries for expressing each of the Fab display synthetic binding sites of this invention were prepared in the following procedure. To form circularized vectors containing the PCR product insert, 640 ng of the digested PCR products were admixed with 2 ug of the linearized pC3AP313 phagemid vector and ligation was allowed to proceed overnight at room temperature using 10 units of BRL ligase (Gaithersburg, Md.) in BRL ligase buffer in a reaction volume of 150 ul. Five separate ligation reactions were performed to increase the size of the phage library having synthetic binding site CDR3 regions. Following the ligation reactions, the circularized DNA was precipitated at −20 C for two hours by the admixture of 2 ul of 20 mg/ml glycogen, 15 ul of 3 M sodium acetate at pH 5.2 and 300 ul of ethanol. DNA was then pelleted by microcentrifugation at 4 C for 15 minutes. The DNA pellet was washed with cold 70% ethanol and dried under vacuum. The pellet was resuspended in 10 ul of water and transformed by electroporation into 300 ul of $E.$ $coli$ XL1-Blue cells to form a phage library. The total yield from the PCR amplification and transformation procedure described herein was approximately $5 \times 10^7$ transformants for each library with the exception that the motif optimized library, prepared from the PCR products described in Example 1D, contained $3 \times 10^7$.

After transformation, to isolate phage on which Fabs displaying synthetic binding sites been induced for subsequent panning on target antigens such as the integrin receptors $\alpha_v\beta_3$, $\alpha_v\beta_5$, $\alpha IIb/\beta_3$, and gp120 protein, 3 ml of SOC medium (SOC was prepared by admixture of 20 grams (g) bacto-tryptone, 5 g yeast extract and 0.5 g NaCl in 1 liter of water, adjusting, the pH to 7.5 and admixing 20 ml of glucose just before use to induce the expression of the Fd-cpIII and light chain heterodimer) were admixed and the culture was shaken at 220 rpm for 1 hour at 37 C, after which 10 ml of SB (SB was prepared by admixing 30 g tryptone, 20 g yeast extract, and 10 g Mops buffer per liter with pH adjusted to 7) containing 20 ug/ml carbenicillin and 10 ug/ml tetracycline and the admixture was shaken at 300 rpm for an additional hour. This resultant admixture was admixed to 100 ml SB containing 50 ug/ml carbenicillin and 10 ug/ml tetracycline and shaken for 1 hour, after which helper phage VCSM13 ($10^{12}$ pfu) were admixed and the admixture was shaken for an additional 2 hours.

After this time, 70 ug/ml kanamycin was admixed and maintained at 30 C overnight. The lower temperature resulted in better heterodimer incorporation on the surface of the phage. The supernatant was cleared by centrifugation (4000 rpm for 15 minutes in a JA10 rotor at 4 C). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4 C). Phage pellets were resuspended in 2 ml of PBS and microcentrifuged for three minutes to pellet debris, transferred to fresh tubes and stored at −20 C for subsequent screening as described below.

For determining the titering colony forming units (cfu), phage (packaged phagemid) were diluted in SB and 1 ul was used to infect 50 ul of fresh ($A_{OO600}=1$) $E.$ $coli$ XL1-Blue cells grown in SB containing 10 ug/ml tetracycline. Phage and cells were maintained at room temperature for 15 minutes and then directly plated on LB/carbenicillin plates.

3. Selection of the Phagemid Fab-Displayed Synthetic Binding Site Proteins

A. Multiple Pannings of the Phage Library Having Phagemid Fab-displayed Synthetic Binding Site Proteins The phage libraries produced in Example 2 having heavy chain fragments with Fab display synthetic binding site regions were panned as described herein on microtiter plates coated with selected target molecules. The target molecules used in screening the phagemid-anchored Fab-displayed synthetic binding site proteins included the following: purified vitronectin receptor (also referred to as VNR) comprised by the pairs of integrin subunits alpha v/beta 3 ($\alpha_v\beta_3$), alpha v/beta 5 ($\alpha_v\beta_5$) or $\alpha IIb/\beta_3$ (gpIIb/IIIa); and the HIV glycoprotein, gp120.

All the vitronectin receptors are commercially for available from Telios Pharmaceutical, San Diego, CA. Alternatively, the $\alpha_v/\beta_3$ and $\alpha_3/\beta_5$ VNRs were purified as described by Smith et al., $J.$ $Biol.$ $Chem.$, 265:11008–11013 (1990), the disclosure of which is hereby incorporated by reference. Briefly, human placentas were obtained, cut into small pieces and extracted by incubation with 100 mM octyl glucose, 2 mM $CaCl_2$, 1 mM phenylmethylsulfonyl fluoride in PBS for 30–40 minutes at room temperature. After filtering the extract through gauze and centrifugation at 12,000×g for 27 minutes, the supernatant was pumped over an anti-VNR antibody Affi-gel column (Bio-Rad, Richmond, Calif.) in which an antibody specific for the particular VNR subunit was previously coupled according to manufacturer's instructions. A monoclonal antibody, LM 609, described by Cheresh et al., $J.$ $Biol.$ $Chem.$, 262:17703–17711 (1987), was used in the purification of $\alpha_v/\beta_3$. An antibody, LM 142, described by Cheresh et al., $Cell$, 57:59–69 (1989), was used in the purification of $\alpha_v/\beta_5$. In addition, antibodies against all 3 VNRs are commercially available for use in purifying target molecules used in screening for Fab-displayed synthetic binding sites of this invention.

After the placenta extract was pumped through the anti-$\alpha_v/\beta_3$ column, the flow through was collected for application on an anti-$\alpha_v/\beta_5$ column. The column was then washed with 50 column volumes of PBS, 0.1% NONIDET P-40, 2 mM $CaCl_2$ and 50 column volumes of 0.01 M acetic acid at pH 4.5 containing 0.1% NP-40 and 2 mM $CaCl_2$. VNR having the $\alpha_v/\beta_5$ subunits was eluted with 0.01 M acetic acid at pH 3.0 containing 0.1% NP-40 and 2 mM $CaCl_2$. The flow through was then applied to the anti-$\alpha_v/\beta_5$ SEPHAROSE column (Pharmacia, Piscataway, N.J.) prepared according to manufacturer's instructions to isolate the specific VNR receptor. The VNR was eluted with 0.01 M acetic acid at pH 3.0 containing 1 mM of $CaCl_2$, $MnCl_2$ and 0.1% NP-40. The fractions from both columns were neutralized by addition of 1.0 ml of 3.0 M Tris-HCl at pH 8.8. The VNR having the $\alpha IIb/\alpha_3$ subunits (also referred to as gpIIb/IIIa) was isolated according to the procedure in U.S. Pat. No. 5,114,842. The above-purified VNRs were used in the panning procedure described below at a concentration of 1 ug/well in a coating buffer consisting of 20 mM Tris-HCl at pH 7.4, 150 mM NaCl and 1 mM each of $CaCl_2$, $MgCl_2$ and $MnCl_2$.

The recombinant gp120 of HIV-1 strain IIIb was commercially available from American Biotechnologies, Ossining, N.Y. The reagent was used at a concentration of 40 ug/ml in the coating buffer, 0.1 M bicarbonate at pH 8.6.

The panning procedure described was a modification of that originally described by Parmley et al., *Gene*, 73:305–318 (1988). Two to four wells of a microtiter plate (Costar 3690) were coated overnight at 4 C with the purified target proteins (VNRs and gp120) prepared above. The wells were washed twice with water and blocked by completely filling the well with 3% (w/v) bovine serum albumin (BSA) in PBS and incubating the plate at 37 C for 1 hour. Blocking solution was removed by shaking, 50 ul of the phage library prepared above (typically 1011 cfu) were added to each well, and the plate was incubated for 2 hours at 37 C.

Phage were removed and the plate was washed once with water. Each well was then washed 10 times with TBS/TWEEN (50 mM Tris-HCl at pH 7.5, 150 mM NaCl, 0.5% TWEEN 20) over a period of 1 hour at room temperature then pipetted up and down to wash the well, each time allowing the well to remain completely filled with TBS/TWEEN between washings. The plate was washed once more with distilled water and adherent phage were eluted by the addition of 50 ul of elution buffer (0.1 M HCl, adjusted to pH 2.2 with solid glycine, containing 1 mg/ml BSA) to each well and incubation at room temperature for 10 minutes. The elution buffer was pipetted up and down several times, removed, and neutralized with 3 ul of 2 M Tris base per 50 ul of elution buffer used. Eluted phage were used to infect 2 ml of fresh ($OD_{600}$=1) *E. coli* XL1-Blue cells for 15 minutes at room temperature, after which 10 ml of SB containing 20 ug/ml carbenicillin and 10 ug/ml tetracycline was admixed. Aliquots of (20, 10, and 1/10 ul were removed for plating to determine the number of phage (packaged phagemids) that were eluted from the plate. The culture was shaken for 1 hour at 37 C, after which it was added to 100 ml of SB containing 50 ug/ml carbenicillin and 10 ug/ml tetracycline and shaken for 1 hour. Helper phage VCSM13 ($10^{12}$ pfu) were then added and the culture was shaken for an additional 2 hours. After this time, 70 ug/ml kanamycin was added and the culture was incubated at 37 C overnight. Phage preparation and further panning were repeated as described above.

To select antibodies with specificity for each integrin from the phage library, integrins $\alpha_v\beta_3$ or $\alpha_{IIb}\beta_3$ were immobilized in Costar 3690 microtiter plates in 50 mM Tris-HCl, 150 mM NaCl, 1 mM $MgCl_2$, 1 mM $CaCl_2$ and 1 mM $MnCl_2$. Selection of phage bearing antigen-specific antibody fragments was performed by panning for six rounds as described above, but with the following modification. In order to select for antibodies with specificity for one or the other integrin, the second integrin was used as a soluble competitor at 20 ug/ml during panning of the phage with the immobilized target integrin. For example, to select antibodies specific for $\alpha_{IIb}\beta_3$, this receptor was immobilized in microtiter wells and $\alpha_{IIb}\beta_3$ was added, in solution, to the phage library during the panning step.

Following each round of panning, the percentage yield of phage were determined, where % yield=(number of phage eluted/number of phage applied)×100.

As an alternative to elution with acid, phage bound to the wells of the microtiter plate were eluted by admixing 50 ul of a solution of $10^{-5}$M of the particular purified coat protein prepared above diluted in PBS followed by a maintenance period of 1 hour at 37 C. The solution was then pipetted up and down to wash the wells. The resultant eluate was transferred to 2 ml of fresh *E. coli* XL1-Blue cells for infection as described above for preparing phage and further panning.

The final phage output ratio was determined by infecting 2 ml of logarithmic phase XL1-Blue cells as described above and plating aliquots on selective plates. In the first panning, approximately $10^{11}$ phage were applied to four wells and approximate yields ranged from 5.0 to 8.0×$10^5$ eluted phage. After the fourth panning, eluted phage ranged from 1.0×$10^6$ to 1.0×$10^8$ phage. The motif switched CDR3 antibodies with their amino acid residue sequences listed in SEQ ID NOs from 19–24 were obtained after five rounds of panning on gpIIb/IIIa. The remainder of the gpIIb/IIIa-reactive clones listed in SEQ ID NOs 25–34, after 10 rounds of panning to select for higher affinity binders that had greater amino acid sequence heterogeneity. From this procedure, clones were selected from each of the Fab libraries for their ability to bind to their respective selected target proteins. The panned phage surface libraries were then converted into ones expressing soluble Fab-displayed synthetic binding site proteins for further characterization as described in Examples 4 and 5.

B. Preparation of Soluble Fab-displayed Binding Site Proteins

In order to further characterize the specificity of the Fab-displayed synthetic binding site proteins expressed on the surface of phage as described above, soluble heterodimers were prepared and analyzed in ELISA assays on target-coated plates and by competitive ELISA with increasing concentrations of soluble competitor protein as described below.

To prepare soluble Fabs consisting of heavy and light chains (i.e., heterodimers), phagemid DNA from positive clones selected in Example 2A above was isolated and digested with SpeI and NheI. Digestion with these enzymes produced compatible cohesive ends. The 4.7 kb DNA fragment lacking the gIII portion was gel-purified (0.6% agarose) and self-ligated. Transformation of *E. coli* XL1-Blue afforded the isolation of recombinants lacking the gIII fragment. Clones were examined for removal of the gIII fragment by XhoI/XbaI digestion, which yielded an 1.6 kb fragment.

Clones were then grown in 100 ml SB containing 50 ug/ml carbenicillin and 20 mM $MgCl_2$ at 37 C until an $OD_{600}$ of 0.2 was achieved. IPTG (1 mM) was added and the culture grown overnight at 30 C (growth at 37 C provides only a light reduction in heterodimer yield). Cells were pelleted by centrifugation at 4000 rpm for 15 minutes in a JA10 rotor at 4 C. Cells were resuspended in 4 ml PBS containing 34 ug/ml phenylmethylsulfonyl fluoride (PMSF) and lysed by sonication on ice (2–4 minutes at 50% duty). Debris was pelleted by centrifugation at 14,000 rpm in a JA20 rotor at 4 C for 15 minutes. The supernatant was used directly for ELISA analysis and was stored at −20 C. For the study of a large number of clones, 10-ml cultures provided a sufficient amount of Fab-displayed synthetic binding site proteins for analysis. In this case, sonications were performed in 2 ml of buffer.

The soluble heterodimers prepared above were assayed by ELISA where applicable as described in Example 4 and 5.

4. Characterization of Soluble Fab-RGD and Gp120 Specific Binding Site Proteins

A. Determination of Specificity of the Binding Site Proteins
 1) ELISA

Three major criteria for a probe of an integrin ligand binding site are the following: 1) The antibody must block the binding of the natural ligand for the receptor; 2) RGD-peptides should block the binding of the antibody; and 3) The binding between the antibody and the integrin should be divalent cation-dependent. Preliminary ELISA assays were performed to first characterize the binding specificity of the panned phage monoclonal antibodies prepared above toward related integrins. For ELISA, 1 ug/well of the purified VNRs prepared in Example 3A was separately admixed to individual wells of a microtiter plate and maintained at 4 C overnight to allow the protein solution to adhere to the walls of the well. After the maintenance period, the wells were washed once with PBS and thereafter maintained with a solution of 3% BSA to block nonspecific sites on the wells. The plates were maintained at 37 C for 1 hour after which time the plates were inverted and shaked to remove the BSA solution. Soluble Fab heterodimers expressing the synthetic binding site proteins-prepared in Example 3B were then admixed separately to each well and maintained at 37 C for 1 hour to form a immunoreaction products. Following the maintenance period, the wells were washed 10 times with PBS to remove unbound soluble antibody and then maintained with a secondary goat anti-human FAB conjugated to alkaline phosphatase diluted in PBS containing 1% BSA. The wells were maintained at 37 C for 1 hour after which the wells were washed 10 times with PBS followed by development with p-nitrophenyl phosphate.

The results of the ELISA assays showed that the Fab-displayed RGDC2 binding site (Mab 8, also referred to as VnR$\beta_3$) as listed in SEQ ID NO 8 bound specifically to $\alpha_v/\beta_3$ and not to $\alpha_v/\beta_5$ as compared to background binding with BSA. Similarly, the Fab-displayed RGDC2 binding site (Mab 11, also referred to as VnR$\beta_5$) as listed in SEQ ID NO 11 bound specifically to $\alpha_v/\beta_5$ and not to $\alpha_v/\beta_3$ as compared to background binding with BSA. Thus, the these two selected Fab-displaying RGD binding site proteins of this invention exhibited specificity to one VNR receptor and not another depending of the subunit composition. This specificity has not been demonstrated before this invention with a RGD-containing sequence for a particular receptor.

In addition, with ELISA performed on gpIIB/IIIa-coated surfaces prepared as described for VnR-coated surfaces, the selected Fab-displaying RGDC2 binding site protein (MAb 19, also referred to as IIb/IIIa-19) as listed in SEQ ID NO 3 was shown to be specific for gpIIb/IIIa and not cross-react with the other VNR receptors. Thus, the method of preparing Fab-displayed synthetic binding site proteins allows for the production of binding site molecules that exhibit heightened specificity for single target molecules as shown herein.

Another monoclonal antibody designated Fab 9 (also referred to as Mab 9, as VnRB3-5 and has the CDR3 amino acid residue sequence in SEQ ID NO 4) was prepared in soluble form and evaluated for its ability to inhibit the binding of vitronectin, fibronectin and fibrinogen to both $\alpha_v/\beta_3$ and gpIIb/IIIa receptors. Fab 9 blocked the binding of the highest affinity ligand for its respective receptor, namely vitronectin for $\alpha_v/\beta_3$ and fibrinogen for gpIIb/IIIa. In the same assay, Fab 9 failed to block vitronectin binding to $\alpha_v/\beta_5$ with any appreciable affinity. Thus, Fab 9 exhibited unique specificity in that $\alpha_v/\beta_5$ has an $\alpha_v$ subunit and the $\beta_5$ subunit is 55% identical to $\beta_3$. Therefore, the appropriate display of the RGD sequence with CDR effectively programmed receptor specificity into the antibody. All Fabs produced by the methods of this invention, including Fab 9, competed with vitronectin for the binding to the receptor in subnanomolar range with $IC_{50}$'s ranging from $1 \times 10^{-10}$ to $5 \times 10^{-10}$. The most potent snake venoms in contrast compete only in the nanomolar range. The affinity of Fab 9 was further characterized by surface plasmon resonance, the procedure of which is described in Example 5 to yield a $K_d$ of $2.5 \times 10^{-10}$ M.

2) Cell Adhesion Assays and Competitive ELISA

Immunoreactive Fabs as determined in the above ELISAs were then analyzed by cell adhesion assays and by competition ELISA to determine the affinity of the Fab-displayed synthetic binding site proteins. In cell adhesion assays, receptor clustering can increase cellular avidity and cells have the potential to metabolize inhibitors. These conditions can override the effects of a weak inhibitor. The cell adhesion assay was performed as described by Wayner et al., *J. Cell. Biol.*, 113:919–929 (1991) and Felding-Habermann et al.,*J. Biol. Chem.*, 267:5070–5077 (1992), the disclosures of which are hereby incorporated by reference.

a) Assays with RGD-containing Fabs

The assay was performed as described above for ELISA with the exception that increasing concentrations of soluble anti-VNR antibodies were added to compete the binding of the RGD-specific VNR receptors on the cell surface to the RGD-containing Fab (also referred to as Fab-displayed RGD) coated on the plate.

For experiments where the binding of cells to the Fab-displayed RGD or cyclized RGD (RGDC2) was inhibited by antibodies to $\alpha_v/\beta_3$, the cells used in the assays were M21 human melanoma cells as they express $\alpha_v/\beta_3$ VNR. For experiments where the binding of the cells to the Fab-displaying RGD or cyclized RGD (RGDC2) was inhibited by antibodies to $\alpha_v/\beta_5$, the cells used in the assays were UCLA-P3 lung carcinoma cells as they express $\alpha_v/\beta_5$ VNR. Other cells expressing the VNRs are contemplated for use in the characterization of selected Fab-displayed synthetic binding sites depending on the target molecule. The competing antibodies ranged in concentration from $10^{-9}$ M up to $10^{-6}$ M in concentration admixed in the presence of the soluble RGD binding site containing Fabs.

In the above inhibition of cell adhesion assay, maximal inhibition of binding was achieved at a concentration of $10^{-6}$ M of competing anti-$\alpha_v/\beta_3$ while an anti-HIV was ineffective.

When Fab 9 that contained an RGD binding site was used in cell adhesion assays, it blocked the melanoma cell adhesion to immobilized vitronectin with an $IC_{50}$ of 4 nM in contrast to the framework antibody pMT12 that had no effect on cell adhesion. More importantly, Fab 9 did not interfere with adhesion to fibronectin, an event largely mediated through $\beta 1$ integrins. This finding provides further evidence that Fab 9 is specific to beta 3 integrins. In similar assays, Fab 9 was compared to vitronectin in the ability to support cellular adhesion. Both proteins supported the binding of cells saturating at approximately 5 ug/ml of Fab or vitronectin. Vitronectin was only slightly more effective at promoting the adhesion of melanoma cells.

Additional competition ELISA assays were performed to confirm the specificity of the Fab-displayed RGD binding site. In these assays, the purified receptors $\alpha_v/\beta_5$ and $\alpha_v/\beta_3$ were separately coated on the plate at a concentration of 1 mM. One nM of the soluble Fab-displayed RGD-binding site shown to be specific for $\alpha_v/\beta_3$ by ELISA as shown above was admixed with iodinated soluble vitronectin (Telios Pharmaceuticals) and then added to the receptor-coated wells. The $\alpha_v/\beta_3$-specific Fab-displayed RGD binding site completely inhibited the binding of labelled vitronectin to the wells while the Fab-displayed RGD binding site specific for $\alpha_v/\beta_5$ did not completely inhibit the binding of labelled vitronectin even at $10^{-6}$ M concentration. Thus, the Fab-displayed RGD binding site proteins of this invention exhibit heightened specificity towards specific VNRs depending on their subunit.

In a separate competition assay, the binding of radiolabeled Fabs, for example Fab 9, to $\alpha_b/\beta_3$ and gpIIb/IIIa was competed by RGD-containing peptides and not by the RGE-containing inactive analog. Moreover, the binding of Fab 9 to $\alpha_v/\beta_3$ and gpIIb/IIIa was shown to be divalent cation-dependent as assessed by the binding of radiolabeled Fab 9 to $\alpha_v/\beta_3$ in the purified receptor binding assay performed as described above. Immobilized $\alpha_v/\beta_3$ was first depleted of endogenously bound divalent cations by treatment with EDTA. The receptor was then replenished with 0.5 mM of either calcium, manganese, or magnesium. Each of these ions was able to support Fab 9 binding to the receptor. Nearly identical results were obtained in similar assays performed with gpIIb/IIIa receptor. Collectively, the results obtained from assays performed with Fab 9, having the RGD binding site as listed in SEQ ID NO 4, show that Fab 9 binds the ligand binding pocket of $\alpha_v/\beta_3$ and gpIIb/IIIa with high affinity and specificity.

Other assays were performed to demonstrate specificity of the Fab-displayed RGD binding site proteins of this invention. A gpIIb/IIIa sandwich ELISA assay was performed on 10 ug/ml (100 ul) of fibrinogen-coated plates. After blocking the plate as described above, the RGD-expressing, Fab, Mab 19, was admixed with purified gpIIb/IIIa receptor. After allowing the RGD-expressing Fab and receptor admixture to immunoreact with the fibrinogen, the wells were washed and the amount of bound gpIIb/IIIa was determined using an anti-IIIa antibody. The results of this assay showed that the Mab 19 expressing an RGDC2 binding site blocked the binding of gpIIb/IIIa to fibrinogen in a dose-dependent manner where maximal inhibition was seen with 5 uM of Fab. No effect was seen with a control anti-gp120 Fab.

b) Assays with Fabs Having the Gp120 Binding Site

Competitive ELISA using soluble CD4 to compete the binding of the Fabs displaying the CD4 sequence recognized by gp120 are then analyzed by competition ELISA to determine the affinity of the selected heterodimers. The ELISA is performed as described above on microtiter wells separately coated with 5 ug/ml of gp120 (American Biotechnologies) in 0.1 M bicarbonate buffer at pH 8.6. Increasing concentrations of soluble or free CD4 (American Biotechnologies) ranging in concentration from $10^{-11}$ M up to $10^{-7}$ M diluted in 0.5% BSA/0.025% TWEEN 20/PBS are admixed with the soluble Fabs displaying the CD4 sequence, the dilutions of which are determined in titration experiments that resulted in substantial reduction of OD values after a 2-fold dilution. The plates are maintained for 90–120 minutes at 37 C and carefully washed ten times with 0.05% TWEEN 20/PBS before admixture of alkaline phosphatase-labelled goat anti-human IgG F(ab')2 at a dilution of 1:500 followed by maintenance for 1 hour at 37 C. Development was performed as described for ELISA.

3) Competition Assays with Peptides Derived from RGD-containing Fab Antibodies

Additional competition assays were performed with a peptide sequence derived from Fab 9. With the methods of this invention, engineering semi-synthetic antibodies by manipulating HCDR3 offered a unique vehicle for the expression and analysis of random peptide sequences. These sequences can be incorporated into the antigen binding site, where conformational constraints may provide peptide motifs with additional structure. Small peptides derived from CDR sequences of antibodies raised via immunization have been shown to emulate whole antibodies both in terms of binding activity and in the ability to block protein function as described by Levi et al., *Proc, Natl. Acad. Sci., USA*, 90:4374–4378 (1993) and Welling et al., *J. Chromatoar*., 548:235–242 (1988). However, the binding affinity of such peptides is generally 2–3 orders of magnitude below the parent antibody from which they are derived.

To determine if the CDR was an appropriate vehicle for displaying and identifying inhibitory peptide motifs, the ability of synthetic peptides derived from the sequence of Fab 9 to block ligand binding to $\alpha_v\beta_3$, $\alpha_v\beta_5$ and $\alpha_{IIb}\beta_3$ was measured. One peptide synthesized as described below for use in this assay contained a RGD motif positioned on the apex of the CDR3 loop but lacked the remaining flanking regions of the CDR3 and rest of the heavy chain. The sequence of the peptide is listed in SEQ ID NO 12. A peptide having the same sequence but flanked by glycine residues to prevent cyclization was also prepared and has the amino acid residue sequence in SEQ ID NO 68. A longer peptide, having the amino acid residue sequence in SEQ ID NO 4 containing all of the amino acids in SEQ ID NO 12 along with flanking amino acid residues, was also prepared. These assays were performed in order to assess the ability of this particular peptide to inhibit the binding of a high affinity ligand to a receptor, namely the binding of vitronectin to $\alpha_v/\beta_3$ or $\alpha_v/\beta_5$ and fibrinogen to gpIIb/IIIa.

The RGD motif originally inserted into the CDR contained two flanking cysteine residues to provide the opportunity for constraining the flexibility of the RGD loop by the formation of a disulfide bond. Since it was not evident whether this disulfide bond actually formed in the antibody's CDR, the potential conformations of the adhesion motif were emulated in synthetic peptides by generating both cyclic and linear forms of each peptide cyclization was achieved and confirmed as described herein.

Peptides derived from HCDR3 sequences were synthesized on Rink's amide resin (0.5 mmol/gm, NovaBiochem) with an Advanced Chemtech 350 multiple peptide synthesizer using Fmoc synthesis as described by Fields et al., *Int. J. Peptide Protein Res*., 35:161–214 (1990). Amino acids were coupled with diisopropylcarbodiimide and 1-hydroxybenzotriazole monohydrate. The side chain Fmoc amino acids were protected by Pmc for arginine, trityl for Cys and butyl for Ser, Thr Asp and Tyr. Each peptide was blocked at the N-terminus by acetylation and at the C-terminus by amidation. Peptides were cleaved from the resin with 10% trifluoroacetic acid/dichloromethane and protecting groups were removed with 5% water/5% anisole/2.5% ethanedithiol/7.5% phenol in trifluoroactetic acid (45). Peptides were precipitated with diethyl ether and purified on a C-18 column (Vydac 201TP1022, 2.2×25 cm) with a 0–100% water/acetonitrile gradient containing 1% trifluoroacetic acid. Cyclizations of cysteine peptides (1 mg/ml) were carried to completion in 20% DMSO/$H_2O$ at pH 4.0 in 1 day as described by Tam et al., *J. Am. Chem. Soc*., 113:6657–6662 (1991). Products from this reaction were purified via HPLC. Fast atom bombardment mass spectroscopy confirmed the molecular weight of the linear and cyclic peptides. The cyclic disulfide peptides were negative for free thiol with Ellman's reagent.

The synthetic peptides from Fab 9 were tested for the ability to antagonize $\alpha_v\beta_3$ and $\alpha_{IIb}\beta_3$ and $\alpha_v\beta_5$ in purified ligand-receptor binding assays performed as described in Example 5b. The results of assays with Fab 9 are shown in FIG. 4A. In FIG. 4A, the linear form of this peptide, designated Lin-9 and listed in SEQ ID NO 68, was tested for the ability to block $^{125}$I-vitronectin binding to $\alpha_v\beta_3$ (open triangles), $\alpha_v\beta_5$ (closed circles) and $^{125}$I-fibrinogen binding to $\alpha_{IIb}\beta_3$ (closed triangles).

Results of competition assays with the Fab 9-derived peptide in SEQ ID NO 68 (FIG. 4A) showed that it completely inhibited the binding of vitronectin to both $\alpha_v/\beta_3$ and gpIIb/IIIa reaching maximal inhibition with $10^{-5}$ M peptide. No inhibition of binding of vitronectin to $\alpha_v/\beta_5$ was obtained. Thus, the peptide derived from Fab 9 exhibited the same inhibitory specificity as the antibody itself inhibiting only one type of vitronectin receptor and gpIIb/IIIa. Similar results were obtained with the circularized Fab 9-derived peptide. These results indicate a preferred motif and arrangement of RGD within a peptide in order to bind to and block high affinity ligand binding over that observed with the simple RGD motif without flanking sequences.

Figure 4A:
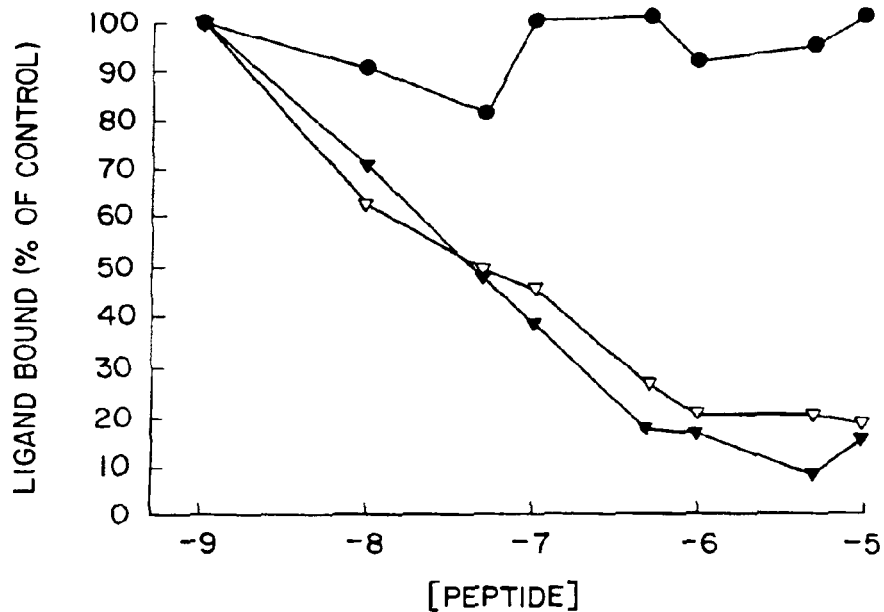
Figure 4B:
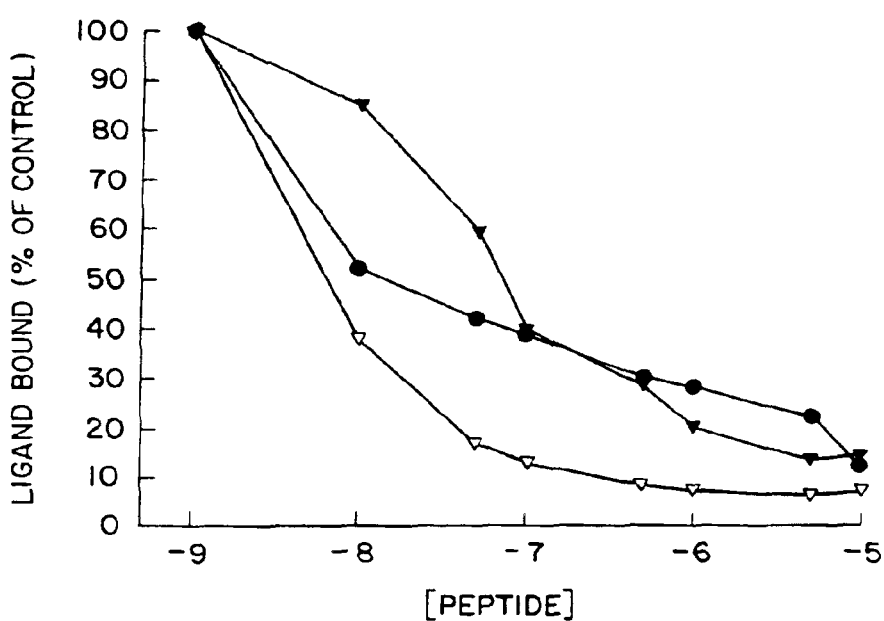

In examining the peptides for activity, two criteria for judging their efficacy, affinity and specificity were used. The proto-typical RGD motif found in fibronectin, GRGDSP (SEQ ID NO 66), was used as a positive control in inhibition assays because it antagonized all three integrins. The assay results are shown in FIG. 4B. In FIG. 4B, the same concentration range of peptide GRGDSP (SEQ ID NO 66) was tested in an identical assay. All data are expressed as the % of control binding in the absence of inhibitor. Data are expressed as the average of triplicate data points. This is representative of four experiments in which nearly identical results were obtained in each repetition.

It is important to note that GRGDSP did antagonize $\alpha_v\beta_5$. In fact, of the three integrins tested, $\alpha_v\beta_5$ had the highest apparent affinity for this peptide. Interestingly, the heavy chain CDR3 peptide derived from Fab 9 inhibited ligand binding to $\alpha_v\beta_3$ and $\alpha_{IIb}\beta_3$, but did not antagonize $\alpha_v\beta_5$ as shown in FIG. 4A. Thus, the linear Fab 9 peptide, designated Lin-9, is the first RGD-containing peptide with specificity for $\alpha_v\beta_3$ over $\alpha_v\beta_5$. Thus, the synthetic peptide derived from this CDR3 emulated the activity of the whole synthetic antibody and satisfied the test of maintaining specificity for a precise integrin target.

Moreover, the Fab 9-derived peptide exhibited specificity in contrast to inhibition experiments with a GRGDSP peptide (SEQ ID NO 66) as shown in FIG. 4B. The GRGDSP peptide did not exhibit any receptor specificity in that it inhibited the binding of all high affinity ligands tested to their respective receptor, vitronectin to both $\alpha_v/\beta_3$ and $\alpha_v\beta_5$ and fibrinogen to gpIIb/IIIa. Thus, the Fab 9-derived peptide retained receptor specificity only inhibiting the binding to only one vitronectin receptor, $\alpha_v/\beta_3$, despite the removal of the flanking regions of the heavy chain variable domain.

Importantly, no significant differences were observed in the efficacy of the cyclic and linear peptides in any inhibition studies, indicating that cyclization was not a determinant in binding affinity. In addition, no difference was observed between linear peptide forms containing terminal cysteines versus terminal glycines, eliminating the possibility that peptide cyclization during the time course of the inhibition assay had an effect on the efficacy of the peptide.

4) Platelet Aggregation Assays

Platelet aggregation assays were performed as described in U.S. Pat. No. 5,114,842. In platelet aggregation assays using the Fab-displayed RGDC2 binding site protein labeled Mab 19 as listed below in Example 4B, 6.6 uM of the purified soluble RGDC2-expressing Fab inhibited the aggregation of platelets in a time-dependent manner as indicated in a decrease in the amount of light transmitted as compared to control human Fabs. When the concentration of the RGDC2-binding site Fab was decreased by half, the amount of platelet aggregation increased similarly and thus the amount of light transmitted increased. When compared in simultaneously performed assays using murine Fabs, in particular with an antibody designated LIBS-1 previously shown to effectively inhibit platelet aggregation, the RGDC2-binding site Fab of this invention was equally effective at inhibiting platelet aggregation. Thus, the methods of this invention allow for the production of novel human Fab molecules that express synthetic binding sites such as RGD peptide as well as the cyclized RGD peptide and that exhibit desired therapeutic characteristics as demonstrated by the ability of the Mab 19 to inhibit platelet aggregation.

B. Sequence Determination of the Binding Site Proteins

Nucleic acid sequencing was performed on double-stranded DNA using Sequenase 1.0 (USB, Cleveland, Ohio) encoding the specific soluble Fab-displayed synthetic binding site proteins of this invention characterized above. The derived amino acid residue sequences of the specific Fab-displayed synthetic binding site proteins for receptors including VNR and gpIIb/IIIa were listed earlier in the Section entitled "Binding Site Polypeptides".

Examination of the sequences revealed homologies within the group and with other known ligands. The SFG-RGD sequence of Fab 9 (in SEQ ID NO 4 from amino acid positions 3 to 8) is found in lamB, in kistrin, and in a number of other snake venoms. Interestingly, one noted feature is the strict conservation of RGD-XR (SEQ ID NO 65) which is not found in any known ligand. In addition, the resultant derived amino acid residue sequences of both the minimum binding site CDR3 as well as the motif switched CDR3 monoclonal antibodies of this invention exhibit some deviations from the expected sequence from the oligonucleotides used in the PCR reactions for incorporating the binding sites. The minor non-perturbing nucleotide substitutions resulting in the encoding of a non-expected amino acid residue is probably the result of non-fidelity of the PCR amplification.

5. Characterization of Soluble Non-RGD-Containing Motif Optimized Binding Site Proteins A. Engineering Antibody Specificity by Motif Optimization and ELISA Characterization In order to identify non-RGD sequences that could antagonize receptor function and to determine whether antibodies could be designed that discriminate between the two $\beta_3$-integrins, "motif optimization" was performed as described in Example 1D. This involved the construction of an additional phage library as described in Example 2.

Since Fab 9 as described in Example 4 had the highest affinity of the first series of RGD-containing antibodies, the residues corresponding to 1–4 and 9–11 of the integrin binding motif in this antibody (as shown in FIG. 1) were maintained in the new phage library. However, residues at positions 5–8, corresponding to RGDI of Fab 9, were randomized by using degenerate oligonucleotide pools (also referred to as oligonucleotide doping) and PCR as described. The complexity of this library ensured a 99% probability that all of the possible amino acid sequences were represented in the randomized four residue motif.

This phage library was screened as described in Example 3A for antibodies that could distinguish $\alpha_v\beta_3$ from $\alpha_{IIb}\beta_3$. Two selections were performed, one for $\alpha_v\beta_3$ and one for $\alpha_{IIb}\beta_3$. The selection process involved the incubation of the phage library with 20 ug/ml of competing integrin in solution, and subsequent panning on the immobilized target integrin. For example, to select antibodies with specificity for $\alpha_{IIb}\beta_3$, integrin $\alpha_v\beta_3$ was incubated with the bacteriophage library in solution prior to panning on immobilized $\alpha_{IIb}\beta_3$. Three rounds of this selection process were performed for each target receptor and the resulting phage were initially tested for specificity by ELISA as described in Example 4.

B. Ligand-Receptor Binding Assays and Inhibition of Binding Assays

Antibodies that displayed a preference for the target integrin in ELISA were screened more rigorously by measuring their ability to antagonize $\alpha_v\beta_3$ and $\alpha_{IIb}\beta_3$ receptor activity in purified ligand-receptor binding assays. The method for these binding studies has been described by Barbas et al., *Proc. Natl. Acad. Sci., USA*, 90:10003–10007 (1993) and Smith et al., *J. Biol. Chem.*, 265:11008–11013 (1990), the disclosures of which are hereby incorporated by reference.

Briefly, selected purified integrins were separately immobilized in Titertek microtiter wells at a coating concentration of 50 ng per well. After incubation for 18 hr at 4° C., non-specific binding sites on the plate were blocked with 10 mg/ml of bovine serum albumin in Tris-buffered saline. For inhibition studies, a range of antibody was tested for the ability to block the binding of $^{125}$I-vitronectin to $\alpha_v\beta_3$ and $^{125}$I-fibrinogen to $\alpha_{IIb}\beta_3$. The choice to use two different ligands in comparing the inhibitory activity of antibodies was a compromise based on a complicated series of circumstances. Ideally the same ligand would have been used for inhibition studies, but fibrinogen does not bind $\alpha_v\beta_3$ when $Ca^{2+}$ is present. In contrast, $Ca^{2+}$ is essential for the rapid binding of fibrinogen to $\alpha_{IIb}\beta_3$. Similar complications arise when vitronectin is considered because it does not bind identically to the two integrins. Therefore, the optimal ligand was selected for each integrin. This corresponds to vitronectin for $\alpha_v\beta_3$ and fibrinogen for $\alpha_{IIb}\beta_3$. Radiolabeled ligands were used at concentrations of 1 nM and binding was challenged with unlabeled antibody.

Following a three hour incubation free ligand was removed by washing and bound ligand was detected by gamma counting. The data from this analysis were highly reproducible with the error between data points typically below 11%. Data are expressed as the average of triplicate data points. All experiments were repeated at least four times.

The ability of two motif optimized Fabs, MTF-2 and MTF-10 to block ligand binding is shown in FIGS. 2A and 2B, respectively. Ligand binding to $\alpha_v\beta_3$ as shown by the line marked with the filled-in circles was measured with $^{125}$I-vitronectin and ligand binding to $\alpha_{IIb}\beta_3$ as shown by the line marked with the open circles was assessed with $^{125}$I-fibrinogen. All data are expressed as the % of control binding in the absence of inhibitor. Non-specific binding was determined by competition with RGD peptides and was normally less than 10% of the total bound counts.

Figure 3A:
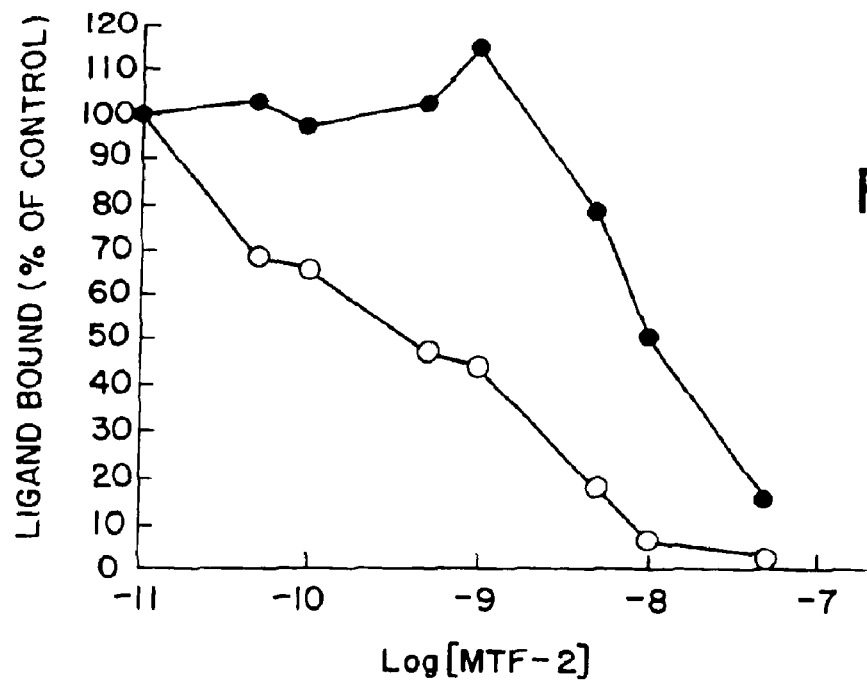
Figure 3B:
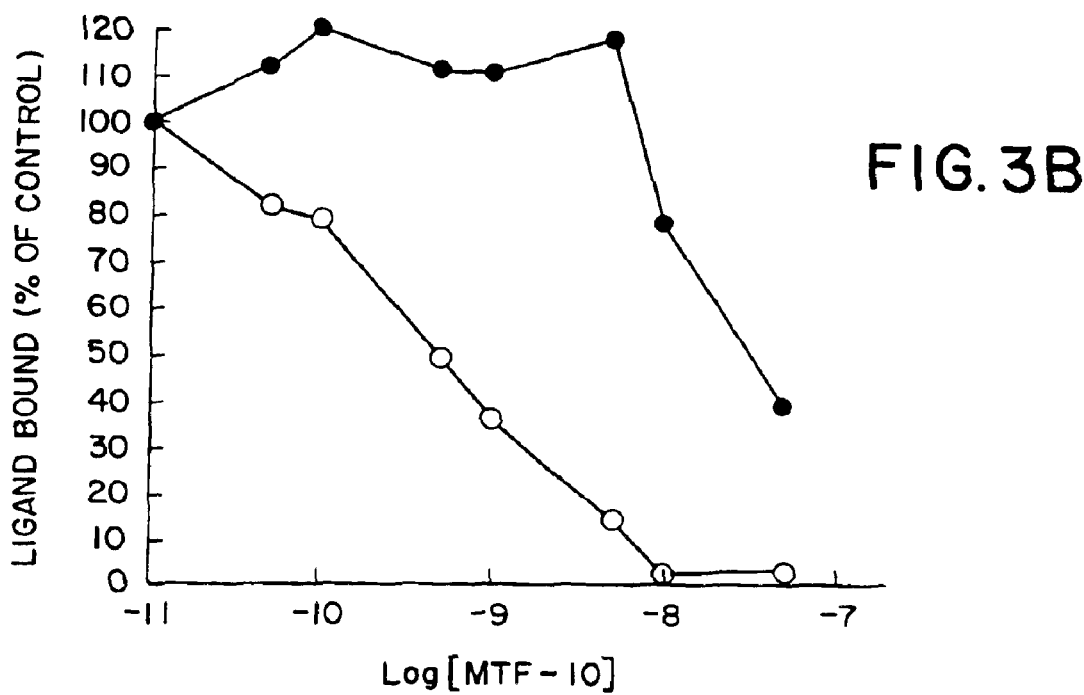

The $IC_{50}$ of MTF-2 was 20-fold lower for $\alpha_{IIb}\beta_3$ than for $\alpha_v\beta_3$ (FIG. 3A). MTF-10 exhibited a 50-fold greater ability to antagonize $\alpha_{IIb}\beta_3$ (FIG. 3B). In particular, the MTF-10 Fab that contained the new binding amino acid motif, GKGDN, as shown in SEQ ID NO 25 from position 6 to 10, at a concentration of $1\times10^{-8}$ M maximally inhibited the binding of vitronectin to IIb/IIIa. In addition, MTF-10 inhibited 60% of the binding of vitronectin to $\alpha_v\beta_3$ when the antibody was used at a concentration of approximately $1\times10^{-7}$ M.

In the same assay NTF-32 displayed a 15-fold preference for $\alpha_{IIb}\beta_3$. All of the MTF antibodies exhibited a higher $IC_{50}$ than the parent Fab 9, indicating that by gaining specificity for $\alpha_{IIb}\beta_3$, some affinity for the integrin was sacrificed.

Thus, by altering a RGD motif by the motif switching methods of this invention, antibodies lacking RGD able to exhibit specificity to integrin receptors were shown to bind high affinity ligands through RGD-mediated binding interaction.

Interestingly, with this motif optimization no antibodies were identified that displayed dramatic binding specificity for $\alpha_v\beta_3$. This indicates that within the context of the Fab 9 scaffold, it is unlikely that the adhesion motifs can be manipulated to gain substantial specificity for $\alpha_v\beta_3$ over $\alpha_{IIb}\beta_3$. This is not surprising because RGD-based ligands that bind to $\alpha_v\beta_3$ are not known and do not bind $\alpha_{IIb}\beta_3$.

C. Amino Acid Sequence Determination

Nucleic acid sequencing was performed on double-stranded DNA using Sequenase 1.0 (USB, Cleveland, Ohio) encoding the specific soluble non-RGD Fab-displayed motif optimized proteins of this invention characterized above. The derived amino acid residue sequences of these specific Fab-displayed proteins for receptors including VNR and gpIIb/IIIa were listed earlier in the Section entitled "Binding Site Polypeptides".

While the RGD-engineered CDR3 monoclonal antibodies all contained RGD within the CDR3 at Kabat positions 100 a–c at the placement of the apex of the extended hair-pin loop of the CDR3 heavy chain, the motif optimized sequences exhibited a number of amino acid substitutions in the RGDI (SEQ NO ID 53) mutated region of Fab 9. The CDR3 listed in SEQ ID NO 4 was re-selected following motif switching mutagenesis one time by screening on gpIIb/IIIa and three times by screening on the VnR receptor, $\alpha_v/\beta_3$.

Thus, this RGD-containing CDR3 amino acid residue sequence represents a more common member of the library that binds to both gpIIb/IIIa and the β3-containing VnR receptor but not to the β5-containing VnR receptor.

Four motif optimized antibodies were obtained that bound preferentially to $\alpha_{IIb}\beta_3$ (gpIIb/IIIa).

These are termed MTF-2, MTF-10, MTF-32 and MTF-40 respectively designated MTFIIb/IIIa-2 (SEQ ID NO 26), MTFIIb/IIIa-10 (SEQ ID NO 25), MTFIIb/IIIa-32 (SEQ ID No 32) and MTFIIb/IIIa-40 (SEQ ID NO 34) as listed herein with their corresponding SEQ ID NOs. The amino acid residue sequences as listed contain the heavy chain CDR3 bordered by framework 3 on the amino terminus and framework 4 on the carboxy terminus as shown in FIG. 1.

None of these MTF antibodies contained the RGD motif, although in three of four cases the R and D were conserved. No functional substitutions for D were observed in any of the selected clones. In MTF-10, the arginine was replaced by lysine, a substitution that has been found in other ligands with specificity for $\alpha_{IIb}\beta_3$, including the snake venom barbourin. Interestingly, the binding pocket of $\beta_3$-integrins can apparently tolerate rather dramatic substitutions at the "G" position because residues which have substantial side chains were accepted in this position. MTF's 2, 10 and 32 had lower $IC_{50}$'s for $\alpha_{IIb}\beta_3$ than $\alpha_v\beta_3$ in purified ligand receptor binding assays.

D. Affinity Measurement and Analysis

A comparison of absolute antibody affinities was then performed with surface plasmon resonance, which is a highly accurate means of assessing ligand affinities in real time. See, Altshuh et al., *Biochem.*, 31:6298–6304 (1992); Chaiken et al., *Anal. Biochem.*, 201:197–210 (1992); Eddowes, *Biosensors*, 3:1–15 (1987); Fagerstam et al., *J. Chromatoar.*, 597:397–410 (1992); Johnsson et al., *Anal. Biochem.*, 198:268–277 (1991); Karlsson et al., *J. Immunol. Methods*, 145:229–240 (1991); and VanCott et al., *J. Immunol. Methods*, 146:163–176 (1992), the disclosures of which are hereby incorporated by reference. SPR is a phenomena that occurs when incoming photons interact with electrons in a biosensor chip. SPR can be used to detect binding between a reactant immobilized on a gold chip and an interacting molecule in solution. The reflective index of the biosensor chip changes as a result of the binding between ligand in solution and the immobilized receptor. This technology has been adapted to study ligand binding to integrins.

SPR was performed using the BIAcore plasmon resonance instrument from Pharmacia (Pharmacia LKB, Piscataway, N.J.). Integrins were immobilized on the biosensor chip with N-hydroxysuccininimide and N-ethyl-N'-(3-diethylaminopropyl)carbodiimide according to the methods outlined by Pharmacia. The sensor surface was first activated with NHS and EDC. Integrins were coupled by injecting 30 uL of a 100 ug/ml sample of purified integrin onto the sensor chip surface. Ethanolamine was used to block unreacted moieties on the sensor chip surface.

Initial studies were done to measure vitronectin binding to $\alpha_v\beta_3$ and fibrinogen binding to $\alpha_{IIb}\beta_3$. Both binding phenomena were inhibited by RGD peptides and were divalent metal ion-dependent. In fact, the association rate constants measured with plasmon resonance were comparable to that which was recently reported with radioligand binding studies. For example, the association rate constant for fibrinogen binding to $\alpha_{IIb}\beta_3$ was $8.5 \times 10^5$ $M^{-1}s^{-1}$ using solid-phase radioligand binding assays, and $6 \times 10^5 M^{-1}s^{-1}$ using SPR. The fibrinogen bound to $\alpha_{IIb}\beta_3$ on the BIAcore sensor chip also exhibited transition to a non-dissociable state. Between 60 and 70% of the bound fibrinogen did not freely dissociate and had to be removed with more stringent regeneration conditions. All of these data validate plasmon resonance as a means of measuring ligand binding to integrins.

The association and dissociation rate constants ($k_1$ and $k_{-1}$) for semi-synthetic antibodies were obtained from BIAcore measurements as follows. To derive $k_{-1}$, a pulse containing ligand was passed through the sensor chip. At the end of the association phase the flow was changed to buffer without ligand and the change in response unit (RU) was measured as a function of time. The dissociation rate constant $k_{-1}$ is derived from equation 1.

$$k_{-1} = (\ln RU_0/RU_t)/t - t_0 \quad \text{Equation 1}$$

$RU_0$ is the initial response unit due to binding of antibody and $RU_t$ is the response unit remaining following dissociation. Time is designated as t.

To obtain the association rate constant $k_1$, an antibody was passed through the sensor chip containing unoccupied integrin and the response unit as a result of binding is again measured as a function of time. The association rate constant, $k_1$, is calculated as shown in equation 2.

$$k_1 = [((dRU/dt)/RU) - k_{-1}]/L \quad \text{Equation 2}$$

L is the concentration of ligand. Measurements of dRU/dt are obtained at several ligand concentrations. The overall $k_D$ of each binding event is derived by simple division shown in equation 3.

$$k_D = k_{-1}/k_1 \quad \text{Equation 3}$$

Duplicate measurements of $k_{-1}$ yielded identical values in all cases. In the case of $k_1$, the error was typically less than 13% across several ligand concentrations.

The results of the surface plasmon resonance affinity analysis for $\alpha_v\beta_3$ and $\alpha_{IIb}\beta_3$ are shown in Table 1. The association ($k_1$ or $k_{on}$) and dissociation ($k_{-1}$ or $k_{off}$) rate constants between synthetic antibodies and the two $\beta_3$-integrins was determined in real time with surface plasmon resonance. Data collection and analysis were performed with purified integrins and Fab fragments as described herein. Measurements were made in either 2 mM $Ca^{2+}$ or 0.2 mM $Mn^{2+}$, both of which have been found to saturate the ligand binding response of the $\beta_3$-integrins.

TABLE 1

| Cation | Receptor | Antibody | $K_{on}$ ($M^{-1}s^{-1}$) | $K_{off}$ ($s^{-1}$) | $K_d$ (M) |
|---|---|---|---|---|---|
| $Ca^{2+}$ (2 mM) | $\alpha_{IIb}\beta_3$ | Fab-9 | $1.3 \times 10^5$ | $7.0 \times 10^{-4}$ | $5.0 \times 10^{-9}$ |
| | | MTF-2 | $7.8 \times 10^4$ | $1.3 \times 10^{-3}$ | $1.7 \times 10^{-8}$ |
| | | MTF-10 | $1.7 \times 10^5$ | $1.2 \times 10^{-3}$ | $7.0 \times 10^{-9}$ |
| | | MTF-32 | $6.8 \times 10^5$ | $2.0 \times 10^{-3}$ | $2.9 \times 10^{-9}$ |
| | | MTF-40 | $7.7 \times 10^5$ | $8.4 \times 10^{-4}$ | $1.1 \times 10^{-9}$ |
| | $\alpha_v\beta_3$ | Fab-9 | $1.4 \times 10^6$ | $2.3 \times 10^{-3}$ | $1.6 \times 10^{-9}$ |
| | | MTF-2 | $1.4 \times 10^4$ | $1.8 \times 10^{-3}$ | $1.3 \times 10^{-7}$ |
| | | MTF-10 | $3.4 \times 10^3$ | $1.7 \times 10^{-3}$ | $5.0 \times 10^{-7}$ |
| | | MTF-32 | $1.5 \times 10^5$ | $1.0 \times 10^{-3}$ | $6.7 \times 10^{-9}$ |
| | | MTF-40 | $1.0 \times 10^5$ | $1.1 \times 10^{-3}$ | $1.1 \times 10^{-8}$ |
| $Mn^{2+}$ (0.2 mM) | $\alpha_{IIb}\beta_3$ | Fab-9 | $4.0 \times 10^3$ | $6.6 \times 10^{-4}$ | $1.6 \times 10^{-7}$ |
| | | MTF-2 | $1.8 \times 10^4$ | $1.7 \times 10^{-4}$ | $1.0 \times 10^{-8}$ |
| | | MTF-10 | $4.3 \times 10^4$ | $3.6 \times 10^{-4}$ | $8.3 \times 10^{-9}$ |
| | | MTF-32 | $1.1 \times 10^5$ | $1.2 \times 10^{-4}$ | $1.0 \times 10^{-9}$ |
| | | MTF-40 | $4.1 \times 10^4$ | $1.5 \times 10^{-4}$ | $3.6 \times 10^{-9}$ |
| | $\alpha_v\beta_3$ | Fab-9 | $2.4 \times 10^5$ | $6.5 \times 10^{-5}$ | $2.8 \times 10^{-10}$ |
| | | MTF-2 | $3.8 \times 10^4$ | $1.0 \times 10^{-3}$ | $2.6 \times 10^{-8}$ |
| | | MTF-10 | $3.6 \times 10^4$ | $1.8 \times 10^{-3}$ | $5.0 \times 10^{-8}$ |
| | | MTF-32 | $1.3 \times 10^5$ | $8.7 \times 10^{-4}$ | $6.7 \times 10^{-9}$ |
| | | MTF-40 | $1.1 \times 10^5$ | $9.6 \times 10^{-4}$ | $8.8 \times 10^{-9}$ |

These measurements demonstrated that the affinities of the MTF antibodies are higher for $\alpha_{IIb}\beta_3$ than $\alpha_v\beta_3$. MTF-10 displayed the highest level of specificity, as its affinity for $\alpha_{IIb}\beta_3$ was 100-fold greater than for $\alpha_v\beta_3$ (Table 1).

One high-affinity antibody, MTF-40, survived the selection process for $\alpha_{IIb}\beta_3$, but did not display dramatic specificity in the purified ligand-receptor binding assays. The sequence of the binding motif in this antibody is RNDS (SEQ ID NO 34 from position 7–10), another non-RGD sequence. Plasmon resonance analysis of the affinity for this Fab showed that in $Ca^{2+}$, it had a 10-fold higher affinity for $\alpha_{IIb}\beta_3$ than $\alpha_v\beta_3$. Importantly, in physiologic [$Ca^{2+}$], this antibody also displayed the highest $k_d$ for $\alpha_{IIb}\beta_3$ of any of the antibodies as measured by surface plasmon resonance ($1.1 \times 10^{-9}$M). It is likely that the preference of this antibody for $\alpha_{IIb}\beta_3$ was not detected in the inhibition assays because it retained very high affinity for $\alpha_v\beta_3$. Because the association rate of the native ligands is so slow, the ligand binding assay is not sensitive enough to detect small differences in binding affinity if the affinity of the antibody is very high. A similar scenario is evident for the parent Fab 9, which has an obvious preference for $\alpha_v\beta_3$ when binding is measured directly with plasmon resonance (Table 1), yet this antibody blocked ligand binding to both integrins identically as described by Barbas et al., *Proc. Natl. Acad. Sci. USA*, 90:10003–10007 (1993).

1) The Binding of Recombinant Fab's to Integrins is Dissociable.

It is well established that the ligands for $\beta_3$-integrins bind in a non-dissociable manner. This has been observed in purified systems and on whole cells. See, Muller et al., *J. Biol. Chem.*, 266:3579–3585 (1991) and Orlando et al., *J. Biol. Chem.*, 266:19543–19550 (1991), the disclosures of which are hereby incorporated by reference. However, ligand mimicking peptides with the RGD sequence freely dissociate from these receptors. Consequently, it was important to determine how the semi-synthetic RGD-containing and non-RGD-containing motif optimized antibodies bound these integrins.

The binding of Fab 9 is shown as an example in this analysis, but its binding behavior was essentially identical to that of the MTF antibodies. The ability of [125]I-Fab 9 to dissociate from purified $\alpha_v\beta_3$ was compared to that of $^{125}$I-vitronectin in purified ligand-receptor binding assays performed as described in Example 5B. Both ligands were incubated with purified $\alpha_v\beta_3$ for four hours. Then buffer containing radioligands was replaced with binding buffer lacking ligand to allow dissociation. An effort was also made to promote dissociation by adding 10 uM GRGDSP (SEQ ID NO 66) after the binding step. This concentration of RGD peptide is 100-fold above the $IC_{50}$ of this peptide when it is simultaneously added with $^{125}$I-vitronectin and $\alpha_v\beta_3$. Following a two hour incubation to allow dissociation, buffer was removed and the amount of $^{125}$I-ligand remaining bound to integrin was measured. The remaining bound ligand was compared to the amount of ligand bound at the beginning of the dissociation step.

From these assays, it was determined that 90% of the bound Fab 9 freely dissociated from $\alpha_v\beta_3$. No competing RGD peptide was necessary to promote dissociation. In contrast greater than 65% of the bound vitronectin remained associated with $\alpha_v\beta_3$. Competition with RGD peptide after the binding event had little effect on dissociation. Similar data were obtained for $\alpha_{IIb}\beta_3$ and also for the other synthetic antibodies. Unlike the native adhesive ligands for the $\beta_3$-integrins, the synthetic antibodies against the ligand binding site freely dissociated from integrin.

2) Measuring Ligand Association and Dissociation Constants with Synthetic Antibodies The dissociable nature of antibody binding to the ligand binding pocket allowed for the first measurement of molecular association and dissociation rates for this site. The association rates of natural ligands for both $\beta_3$-integrins have been previously established, but data regarding dissociation was not obtained because of the stabilized binding between adhesive proteins and integrins.

To accurately quantify association and dissociation rates between the semi-synthetic Fab antibodies of this invention and the $\beta_3$-integrins, surface plasmon resonance was as described above. To validate this approach for integrins, preliminary binding studies were done between fibrinogen and $\alpha_{IIb}\beta_3$ and between vitronectin and $\alpha_v\beta_3$ as described above.

The binding of the MTF antibodies and Fab 9 were compared on both $\alpha_v\beta_3$ and $\alpha_{IIb}\beta_3$. The association and dissociation constants and the $k_D$'s of each antibody for both integrins are listed in Table 1 shown above. In prior studies it was determined that ligand binding to either integrin could be maximally supported by either 2 mM $Ca^{2+}$ or 200 uM $Mn^{2+}$, and that these ions had different effects on ligand association (Smith et al., *J. Biol. Chem.*, 266:11429–11432 (1991). Consequently, the association and dissociation rate constants for antibodies were determined under both conditions. Because the MTF antibodies lacked RGD, these data conclusively show that absolute adherence to this motif is not necessary for high-affinity binding to $\beta_3$-integrins. Even though the MTF antibodies all showed substantial preference for $\alpha_{IIb}\beta_3$, they did have reasonable affinity for $\alpha_v\beta_3$. In fact, the association rate constants of the MTF antibodies for $\alpha_v\beta_3$ are between $10^3$ and $10^5 M^{-1}s^{-1}$, a range identical to that found for the native RGD containing ligands. Therefore, if presented in the proper context, protein sequences other than RGD can bind both $\beta_3$-integrins.

3) Divalent Ions Regulate $k_1$ for Synthetic Antibodies

Divalent cations regulate the association of natural ligands with both $\alpha_v\beta_3$ and $\alpha_{IIb}\beta_3$. The binding of the synthetic antibodies against the ligand binding site were also markedly influenced by the type of divalent ion present. Since these antibodies freely dissociated from integrin they provided the first opportunity to measure the influence of divalent metals on both association and dissociation.

To provide an easy means of examining the influence of different divalent ions on antibody binding, the ratio of $k_1$ ($k_{on}$) in $Mn^{2+}$ to $k_1$ in $Ca^{2+}$ was calculated. The same calculation was performed for $k_{-1}$ ($k_{off}$). The results are shown in Table 2. The values used for these calculations were derived from the affinity measurements with plasmon resonance which are listed in Table 1. Smith et al., *J. Biol. Chem.*, 265:11008–11013 (1990) found that integrin $\alpha_{IIb}\beta_3$ always bound ligands poorly in buffer containing only $Mn^{2+}$, consequently the ratio's of $k_1$ for this integrin are always much lower than 1. Ratios of one indicate equivalent association in both ions. Ratios above one indicate faster association in $Mn^{2+}$.

TABLE 2

| Synthetic Antibody | $\alpha_v\beta_3$ $k_{on}$ Mn/Ca | $\alpha_v\beta_3$ $k_{off}$ Mn/Ca | $\alpha_{IIb}\beta_3$ $k_{on}$ Mn/Ca | $\alpha_{IIb}\beta_3$ $k_{off}$ Mn/Ca |
|---|---|---|---|---|
| Fab-9 | 0.17 | 0.02 | 0.03 | 0.94 |
| MTF-2 | 2.71 | 0.55 | 0.23 | 0.13 |
| MTF-10 | 10.5 | 1.05 | 0.25 | 0.30 |
| MTF-32 | 0.86 | 0.87 | 0.16 | 0.06 |
| MTF-40 | 1.10 | 0.87 | 0.05 | 0.17 |

As shown in Table 2, there was a wide variation in the effect of divalent ions on association rate constants. The parent antibody, Fab 9, had a substantially faster on-rate for a in $Ca^{2+}$ than in $Mn^{2+}$. Conversion of the RGDI (SEQ ID NO 4 from position 7–10) sequence of Fab 9 to the RTDQ (SEQ ID NO 26 positions 7–10) sequence in MTF-2 completely switched the cation preference for binding to $Mn^{2+}$. The antibody with the largest difference in association rate constants was MTF-10, which has a KGDN (SEQ ID NO 25 from position 7–10) sequence. The association rate constant for this antibody was 10-fold higher in $Mn^{2+}$ than in $Ca^{2+}$. This was a drastic reversal of the ion preference shown by the parent antibody, indicating that sequence changes within the four core residues of the integrin recognition motif can dramatically affect a ligand's behavior with respect to divalent ions.

Integrin $\alpha_{IIb}\beta_3$ binds all of its natural ligands faster in $Ca^{2+}$ than in $Mn^{2+}$. This trend is also evident with the semi-synthetic RGD-containing and non-RGD-containing motif optimized antibodies of this invention. Regardless of the antibody tested, the ratio of association rate constants in $Mn^{2+}$ versus $Ca^{2+}$ is always substantially below 1. However, sequence changes in residues 5–8 can alter this ratio as much as five-fold. MTF-40 has a $Mn^{2+}/Ca^{2+}$ preference of 0.05, but for NTF-2 the ratio is 0.23. The dissociation rate constants also varied with the type of divalent ion present, but there was no obvious correlation between the influence of ions on $k_1$ and $k_{-1}$ for a given antibody. For example, when binding $\alpha_v\beta_3$ MTF-32 had nearly identical ratios for $k_1$ and $k_{-1}$, 0.86 and 0.87. In contrast, the ratios for MTF-10 on $\alpha_v\beta_3$ were 10 and 1. Consequently, divalent ions can influence the ligand on-rate without necessarily influencing its off-rate.

These results indicate that prior to the transition to a stable complex between integrins and their natural ligands, ligand association and dissociation can be regulated independently. Depending on the time required for transition to a stable complex, the independent regulation of binding and dissociation could be important for regulating cellular extension on the extracellular matrix.

4) Antibody Association Rate Constants Validate the Antibody Selection Technique Panning as described in Example 2B is becoming a standard technique for identifying high affinity binders from within phage libraries, yet little systematic study has been reported regarding the efficiency of the panning approach. The scheme for selecting specific antibodies against $\alpha_{IIb}\beta_3$ involved competing with $\alpha_v\beta_3$ in solution and panning the non-bound antibodies on immobilized $\alpha_{IIb}\beta_3$. The panning step was set at two hours, and the non-bound phage were removed with a one hour wash period.

To assess the success of the competitive selection process designed for identifying antibodies with specificity for $\alpha_{IIb}\beta_3$, the ratio of the association rate constant for $\alpha_v\beta_3$ to the association rate constant for $\alpha_{IIb}\beta_3$ was calculated. The values for this derivation were obtained from plasmon resonance measurements listed in Table 2. Ratio's of 1 indicate the antibody has an identical ability to associate with both receptors. Ratio's of less than 1 indicate a preference for $\alpha_{IIb\beta3}$. All antibodies from the MTF series have lower ratio's than the parent antibody, Fab 9.

TABLE 3

| Antibody | $k_{on}$ in $Ca^{2+}$ $\alpha_v\beta_3/\alpha_{IIb}\beta_3$ | $k_{on}$ in $Mn^{2+}$ $\alpha_v\beta_3/\alpha_{IIb}\beta_3$ |
| --- | --- | --- |
| Fab-9 | 10.7 | 60 |
| MTF-2 | 0.17 | 2.1 |
| MTF-10 | 0.02 | 0.83 |
| MTF-32 | 0.22 | 1.1 |
| MTF-40 | 0.12 | 2.6 |

This comparison reveals that the motif optimization and selection was highly successful. The parent antibody, Fab 9, displayed on-rates that favored $\alpha_v\beta_3$. In buffer containing $Ca^{2+}$, the $k_1$ ratio for this antibody was 10, indicating preference for $\alpha_v\beta_3$. All of the MTF antibodies, which were selected on $\alpha_{IIb}\beta_3$, had ratios of less than 1, indicating a preference for $\alpha_{IIb}\beta_3$. Although the absolute values of ratios of $k_1$, were different in $Mn^{2+}$, the same trend was evident. Inspection of the overall $k_D$'s for the MTF antibodies (Table 1) shows that the overall antibody binding affinity was also generally higher for $\alpha_{IIb}\beta_3$ than $\alpha_v\beta_3$. These results indicate that the competitive selection process properly identified antibodies with specificity for $\alpha_{IIb}\beta_3$.

E. Comparison of Fab 9 and MTF-10 in Platelet Aggregation and Cell Adhesion

All of the initial selection and characterization of the semi-synthetic Fab antibodies of this invention relied largely upon the use of purified integrins. Since the MTF-antibodies blocked the function of $\alpha_{IIb}\beta_3$ and have potential therapeutic use in the prevention of thrombosis, the ability of recombinant Fabs to block platelet aggregation was measured as described in Example 4. Washed platelets ($1\times10^8$) were placed in Tyrode's buffer containing 2 mM $Ca^{2+}$ and 100 ug/ml of fibrinogen and aggregation was stimulated by addition of 20 uM ADP. Aggregation was measured as light transmission through the platelet suspension using a Scienceo aggregometer.

As described in Example 4A4), Fab 9 blocked one-half of the aggregation at a concentration of near 5 nM. This antibody completely blocked aggregation at an antibody concentration of 20 nM. Only slightly more MTF-10 was required for inhibiting aggregation, with half-maximal inhibition at 20 nM Fab and complete inhibition at 100 nM. The aggregation data were also in accordance with the affinities of these two antibodies as measured by plasmon resonance. The other MTF antibodies were similar to MTF-10 in their ability to interfere with platelet aggregation. These findings show that the semi-synthetic antibodies of this invention can abrogate platelet aggregation and substantiate their potential as anti-thrombotic agents.

Analysis of MTF-10 in purified systems indicated that it should have a substantially reduced ability to bind $\alpha_v\beta_3$ on the cell surface. This assay, performed as described in Example 4, was performed with whole cell adhesion assays using M21 melanoma cells because they adhere to RGD-ligands primarily via $\alpha_v\beta_3$. M21 cells were allowed to adhere to a concentration range from 1 to 10 ug/ml of immobilized Fab 9 and MTF-10.

The cells were able to adhere to the RGD-containing Fab, but were unable to bind to MTF-10 which has a KGDN (SEQ ID NO 25 from position 7–10) sequence instead of RGDI (SEQ ID NO 4 from position 7–10). Antibody MTF-10 did support the adhesion of chinese hamster ovary cells expressing recombinant human $\alpha_{IIb}\beta_3$.

F. Preparation of Synthetic Peptides Derived from Fab Antibody HCDR3 Protein Sequences The ability of peptides derived from MTF-32 and MTF-40 to block ligand binding to the two $\beta_3$-integrins was measured. Peptides derived from the sequence of MTF-10, which has a KGD sequence, were not tested because peptides containing this motif have previously been shown bind and inhibit $\alpha_{IIb}\beta_3$. See Ginsberg et al., *J. Biol, Chem.*, 260:3931–3936 (1985).

Since antibodies MTF-32 and MTF-40 had a higher affinity for $\alpha_{IIb}\beta_3$ in plasmon resonance analysis (Table 1), and because these antibodies lacked RGD, peptides derived from these CDR's were also tested for their ability to block ligand binding to $\alpha_v\beta_3$ and $\alpha_{IIb}\beta_3$. Both cyclic and linear versions of peptides derived from MTF-32 and MTF-40 were synthesized as described for Fab 9 in Example 4A3). The data presented herein is analyzed in view of the results of similar peptide competition assays with Fab 9 as described in Example 4A3).

Figure 4C:
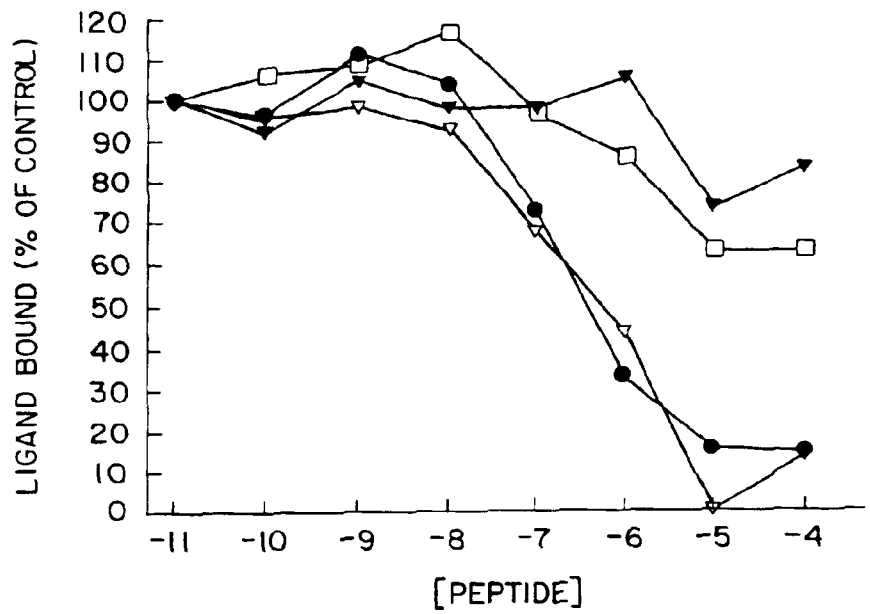

In FIG. 4C, peptides derived from HCDR3 of MTF-40, peptide CSFGRNDSRNC (SEQ ID NO 69) and peptide GCSFGRNDSRNCY (SEQ ID NO 70) were synthesized. The cyclic form is indicated in the figure with open squares and open triangles while the linear form is shown as closed circles and closed triangles. The ability of these peptides to block ligand binding to $\alpha_v\beta_3$ (closed triangles and open squares) and $\alpha_{IIb}\beta_3$ (closed circles and open triangles) was compared. All data are expressed as the percent of control binding in the absence of inhibitor. Data points are the average of triplicate values. This experiment is representative of three repetitions in which nearly identical results were obtained.

Figure 4D:
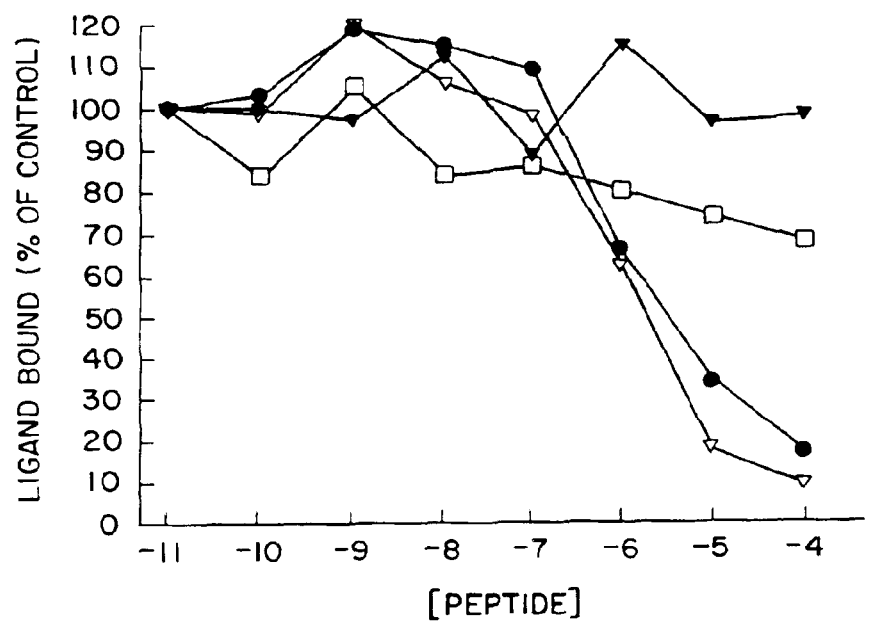

In FIG. 4D, similar measurements were made for peptides derived from HCDR3 of NTF-32, circular peptide CSFGRTDQRNC (SEQ ID NO 71) and linear peptide GCSFGRTDQRNCY (SEQ ID NO 72). Linear (closed triangles and closed circles) and cyclic (open triangles and open squares) peptides were tested for the ability to block ligand binding to $\alpha_v\beta_3$ (closed triangles and open squares) and $\alpha_{IIb}\beta_3$ (closed circles and open triangles). Again the data are the average of triplicate points and the experiment is representative of three repetitions with similar results.

Both linear and circular peptides 32 and 40 blocked fibrinogen binding to $\alpha_{IIb}\beta_3$, but did not interfere with ligand binding to $\alpha_v\beta_3$ over the range of peptide concentrations tested (from $1\times10^{-4}$ to $1\times10^{-11}$ M) as shown in FIGS. 4C and 4D. Higher concentrations of peptide were not evaluated because several non-specific peptides began to disrupt ligand binding in this assay at concentrations of $5\times10^{-4}$ M. For integrin $\alpha_{IIb}\beta_3$, the $IC_{50}$ of peptide 40 is $5\times10^{-7}$M and that of peptide 32 is $2+10^{-6}$M. The activity of the peptides was not enhanced by cyclization. Although the affinity of these peptides for $\alpha_{IIb}\beta_3$ is low compared to GRGDSP (SEQ ID NO 66) (FIG. 4B), they do maintain the binding specificity exhibited by the parent antibodies.

G. Summary

With the methods of this invention, integrin ligands, and antagonists, that maintain a high degree of specificity were designed. Semi-synthetic Fab antibodies were re-designed as integrin ligands by manipulating the antigen binding site. The placement of an integrin ligand motif into the complementarity determining region of a human antibody's heavy chain, and optimization of this motif by selecting high affinity antibodies was accomplished with the phage-display libraries. Interestingly, important differences were observed in the way that the synthetic antibodies and native ligands bind to integrins. Native adhesive ligands for the integrins typically have very low association rate constants, but ultimately bind in a non-dissociable manner. In contrast, this invention has provided synthetic antibodies that bound the $\beta_3$ integrins rapidly, with at least one interaction of greater than $1 \times 10^6$ $M^{-1}s^{-1}$. This rate is 600-fold faster than the association of vitronectin for $\alpha_v\beta_3$. However, unlike vitronectin, all of the antibody ligands bound in a completely dissociable manner. The inability of the semi-synthetic antibodies to bind tightly, i.e., in a non-dissociable manner, indicates that the native ligands have ancillary contact surfaces aside from RGD that contribute to the stabilized binding state. These hypothesized secondary contact points are also a likely means of obtaining another level of specificity between integrins and their natural ligands.

In most cases, therapeutic application of antagonists of $\beta_3$-integrins will require some measure of specificity for either $\alpha_v\beta_3$ or $\alpha_{IIb}\beta_3$. Semi-synthetic antibodies that could distinguish these two integrins were prepared with the methods of this invention and thus the methods provide for affinity enhancement for $\alpha_{IIb}\beta_3$. Three of the antibodies in the motif optimized (MTF) series showed preference for $\alpha_{IIb}\beta_3$. MTF-10 showed a 100-fold higher $k_D$ for $\alpha_{IIb}\beta_3$ than $\alpha_{IIb}\beta_3$.

Interestingly, the same selection strategy to find antibodies with preference for $\alpha_v\beta_3$ was used but without success. Fab 9, which was originally identified by panning on pure $\alpha_v\beta_3$, did show preference for this integrin in plasmon resonance binding studies, antibodies with greater specificity were not obtained by optimizing the motif in Fab 9. The complexity of the library screened was sufficient to ensure that all potential amino acid sequences were present in the motif optimization, leading to the conclusion that the within the context of the adhesion motif shown in FIG. 1, the set of all sequences that bound $\alpha_v\beta_3$ also bound $\alpha_{IIb}\beta_3$. Interestingly, no natural ligands have been identified that bind $\alpha_v\beta_3$ substantially better than $\alpha_{IIb}\beta_3$.

Although peptidomimetics and cyclic peptides have been reported to have a high degree of specificity for $\alpha_{IIb}\beta_3$ as described by Isoai et al., *Cancer Lett.*, 65:259–264 (1992), compounds that have good preference for $\alpha_v\beta_3$ have not been identified. Some snake venoms have also been reported with preference for $\alpha_v\beta_3$, but the best example, cerastin, had only a 20-fold lower $IC_{50}$ for $\alpha_v\beta_3$ than $\alpha_{IIb}\beta_3$. Collectively, these data indicate that it will be substantially more challenging to obtain an RGD-based antagonist with a large degree of selection for $\alpha_v\beta_3$.

Since all of the potential natural amino acid sequences with the MTF selection strategy has been exhausted with the methods of this invention, it is likely that $\alpha_v\beta_3$-specific antagonists will require access to functional moieties not present in the 20 amino acids, and will have to be organically synthesized. This does not exclude the possibility that antibodies can be further engineered to gain selection for $\alpha_v\beta_3$. For example, the HCDR3 of Fab 9 can be recombined with libraries of light chains in order to build in other contact sites specific for $\alpha_v\beta_3$. Alternatively, five other CDR's are present in the antibody and could be genetically manipulated to achieve the same end.

The integrin ligand binding pocket could also accommodate more proteins than originally thought. The RGD motif is certainly not an absolute requirement for occupation of the ligand binding site of the $\beta_3$-integrins. By starting with the optimal presentation of the ligand motif in Fab 9 (FIG. 1), and then randomizing the RGDX positions, numerous non-RGD sequences were identified that bound and antagonized both $\beta_3$-integrins. None of these sequences were observed by the selection of linear or disulfide constrained phage libraries on integrins as described by O'Neil et al., *Proteins*, 14:509–515 (1992). Such libraries provided only the previously observed RGD and KGD motifs. In fact, in addition to the MTF series of antibodies, four other antibodies lacking RGD that bound both $\alpha_v\beta_3$ and $\alpha_{IIb}\beta_3$ were identified. Three of these antibodies displayed $IC_{50}$ values 20 to 50-fold higher than Fab 9 in ligand binding in purified assays. The CDR sequences of these antibodies at positions 5–8 (FIG. 1) were RWDA (SEQ ID NO 73), RADR (SEQ ID NO 74) and KRDM (SEQ ID NO 75). One antibody with sequence RVDD (SEQ ID NO 76) had an $IC_{50}$ value comparable to that of Fab 9 but did not distinguish the two $\beta_3$-integrins.

In conjunction with the sequences of the MTF antibodies as shown in Section B, these data indicate that adhesion motif position #6 (FIG. 1) which corresponds to the "G" position in the RGD, is highly permissive. G was found to be substituted by A,D,N,R,Q,S,T and W. A full stearic spectrum of side chains was tolerated in this position. Importantly, the antibodies lacking RGD had association rates that rivaled the fastest association partner for a $\beta_3$-integrin, fibrinogen. Therefore, the potential ligands for the $\beta_3$-integrins should be expanded to include proteins with RXD motifs. It is possible that further divergence from the RGD sequence at other positions could also be tolerated because MTF-10, which has a KGD at positions 5–7 (FIG. 1), still bound $\alpha_v\beta_3$ at a rate comparable to vitronectin, the natural ligand for this integrin. Extending the definition of $\beta_3$ ligands to sequences of (K/R)XD should be considered. This would vastly increase the number of potential ligands for integrins. This is illustrated by a computer search of the Protein Identification Resource Database using the RTDQ (SEQ ID NO 32 from position 7–10) sequence of antibody MTF-32. Of 56,849 sequences in the database, 3,026 contained RTDQ. Similar numbers were obtained for RNDS (SEQ ID NO 34 from position 7–10), the active sequence within MTF-40. Consequently, the pool of potential $\beta_3$ ligands is much larger than originally believed.

The sequences we identified at motif positions 5–8 were also distinct from two antibodies raised by immunization that bind the ligand binding site of $\alpha_{IIb}\beta_3$ as described by Taub et al., *J. Biol. Chem.*, 264:259–265 (1989) and Tomiyama et al., *Blood*, 79:2302–2312 (1992), the disclosures of which are hereby incorporated by reference. These are OPG2 and PAC-1, both of which have an RYD motif in CDR3. The methods used herein did not result in any antibodies with this sequence. It is likely that PAC-1 and OPG2 which have reported high specificity for $\alpha_{IIb}\beta_3$ also derive binding affinity from secondary contacts with integrin that are contributed by other CDR's in the antibody.

Much recent effort has been placed on screening for ligand motifs using random peptide libraries in conjunction with phage-display technology as referred to in the Background. The methods of this invention differed substantially in that the CDR of an antibody was used as a vehicle for presentation of the peptide motif. Therefore, whether synthetic peptides derived from the selected sequences would behave faithfully as high fidelity antagonists was not known. In fact, the HCDR3-derived peptides of this invention did block integrin function. More importantly though, these peptides mimicked the target specificity of the parent antibody. Even though both $\beta_3$-integrins and the highly related integrin $\alpha_v\beta_3$ bound to the proto-typical RGD sequence, GRGDSP (SEQ ID NO 66), the RGD peptide derived from Fab 9 bound only the $\beta_3$-integrins. Similar target specificity was observed for peptides derived from MTF-32 and MTF-40. Like the parent antibodies, peptides 32 and 40 showed specificity for $\alpha_{IIb}\beta_3$ over $\alpha_v\beta_3$. It is unclear whether the selection of the proper flanking residues in the antibody CDR contribute more contacts with integrin, or whether these flanking residues have conformationally constrained the angle that defines the orientation of the side chains of the R and D, a parameter known to influence receptor binding affinity. Since the cyclic peptides provided no advantage over the linear peptide sequences in terms of affinity or selectivity, the optimal flanking residues may add additional contact points for the integrin. It is also reasonable to assume that the antibody scaffold with its interacting loops displays the HCDR3 in a manner which is not easily mimicked by simple cyclization.

Thus, this invention demonstrates the potential for using CDR's as a design template for obtaining inhibitory CDR-derived peptides. The findings presented here indicate that antigen binding peptides derived from the antibody's CDR sequence could be optimized with phage-display.

A major advantage to building human antibodies that bind the integrin ligand binding site is that they could have immense therapeutic application, particularly because they should circumvent a host immune response. The two $\beta_3$ integrins have been implicated in numerous diseases. An antagonist of the platelet integrin would arrest platelet aggregation, and could find wide application in treating thrombotic episodes. In fact, antagonists of $\alpha_{IIb}\beta_3$ have been effective at blocking platelet function in vivo. The findings presented here certainly show that a semi-synthetic approach to generating anti-integrin antibodies is valuable. MTF-10, which has substantially higher affinity for $\alpha_{IIb}\beta_3$ over $\alpha_v\beta_3$ (100-fold) is a good candidate for testing anti-platelet activity in in vivo models of thrombosis. The fact that some of the semi-synthetic antibodies antagonized both $\beta_3$-integrins with high affinity may be extremely useful in combating certain types of metastasis. It is now thought that melanoma is often carried through the vasculature by adhesion to circulating platelets. This cell-cell bridge is thought to involve $\alpha_v\beta_3$ on the tumor cell and $\alpha_{IIb}\beta_3$ on the platelet. Blocking both ends of this adhesion event with the semi-synthetic antibodies described here would seem to present a superb therapeutic strategy.

6. Preparation of Synthetic Binding Sites Within the Light Chain CDR3 Domain of a Phagemid Fab Display Protein Produced by a Dicistronic Expression Vector In addition to creating synthetic binding sites within the heavy chain of CDR3,in a phagemid-expressed Fab, similar sites were produced in the light chain of CDR3. For this aspect of this invention, the phagemid expression vector, pC3AP313, containing heavy and light chain sequences for encoding a human antibody that immunoreacted with tetanus toxin, was used as a template for PCR. The vector was prepared as described in Example 1 while the PCR protocol was performed as described below using overlap PCR.

For overlap PCR, each set of PCR reactions were performed in a 100 ul reaction containing 1 ug of each of oligonucleotide primers listed below in a particular pairing, 8 ul 2.5 mM dNTP's (dATP, dCTP, dGTP, dTTP), 1 ul TAQ POLYMERASE, 10 ng of template p7EIII, and 10 ul of 10× PCR buffer purchased commercially (Promega Biotech). The amplification cycles were performed as described in Example 1A. The resultant PCR amplification products were then gel purified as described in Example 1A and used in an overlap extension PCR reaction with the products of the second PCR reaction, both as described below, to recombine the two products into reconstructed heavy chains containing mutagenized CDR3.

To amplify the 5' end of the light chain from framework 1 to the end of framework 3 of pC3AP313, the following primer pairs were used. The 5' coding oligonucleotide primer, KEF, having the nucleotide sequence 5' GAAT-TCTAAACTAGCTAGTCG3' (SEQ ID NO 59), hybridized to the noncoding strand of the light chain corresponding to the region 5' of and including the beginning of framework 1. The 3' noncoding oligonucleotide primer, KV12B, having the nucleotide sequence 5' ATACTGCTGACAGTAATA-CAC3' (SEQ ID NO 60), hybridized to the coding strand of the light chain corresponding to the 3' end of the framework 3 region. The oligonucleotide primers were synthesized by Operon as described in Example 1A.

The PCR reaction was performed in a 100 ul reaction as described above in Example 1A with the exception that 10 ng of template pC3AP313 was used. The amplification cycles were performed as described in Example 1A. The resultant PCR amplification products were then gel purified as described in Example 1A and used in an overlap extension PCR reaction with the products of the second PCR reaction, both as described below, to recombine the two products into reconstructed light chains containing mutagenized CDR3.

The second PCR reaction resulted in the amplification of the light chain from the 3' end of framework region 3 extending to the end of CH1 region. To amplify this region for encoding a 4 random amino acid residue sequence in the CDR3, the following primer pairs were used. The 5' coding oligonucleotide primer pool, designated KV5R, had the nucleotide sequence represented by the formula, 5' TAT-TACTGTCAGCAGTATNNKNNKNNKNN-KACTTTCGGCGGAGGGACCAAGG TGGAG3' (SEQ ID NO 61), where N can be A, C, G, or T and K is either G or T. The 3' noncoding primer, T7B, hybridized to the coding strand at the 3' end of CH1 having the sequence 5' AATAC-GACTCACTATAGGGCG3' (SEQ ID NO 62). The 5' end of the primer pool is complementary to the 3' end of framework 3 represented by the complementary nucleotide sequence of the oligonucleotide primer KV12B and the 3' end of the primer pool is complementary to the 5' end of framework 4. The region between the two specified ends of the primer pool is represented by a 12-mer NNK degeneracy. The second PCR reaction was performed on the pC3AP313 in a 100 ul reaction as described above containing 1 ug of each of oligonucleotide primers. The resultant PCR products encode a diverse population of mutagenized light chain CDR3 regions of 4 amino acid residues in length with a conserved aspartic acid residue in the fourth amino acid residue position in the CDR3. The products were then gel purified as described above.

One hundred nanograms of gel purified products from the first and second PCR reactions were then admixed with 1 ug each of KEF and T7B oligonucleotide primers as a primer pair in a final PCR reaction to form a complete light chain fragment by overlap extension. The PCR reaction admixture also contained 10 ul 10× PCR buffer, 1 ul TAQ POLYMERASE and 8 ul 2.5 mM dNTP's as described above. The PCR reaction -was performed as described in Example 1A.

To obtain sufficient quantities of amplification product, 15 identical PCR reactions were performed. The resulting light chain fragments beginning at framework 1 and extending to the end of CH1 and having a randomly mutagenized CDR3 region for encoding 4 amino acid residues. The light chain fragment amplification products from the 15 reactions were first pooled and then gel purified as described above prior to their incorporation into the pc3AP313 surface display phagemid expression vector to form a library as described in Example 2.

To create synthetic binding site sequences for encoding CDR3 regions having length of 5, 6 and 10 amino acid residues, the following primers were used separately in the second PCR reaction in combination with the 3' primer, T7B: 1) for encoding a 5 amino acid sequence, the KV5R primer had the formula 5' TATTACTGTCAGCAGTATNN-KNNKNNKNNKNNKACTTTCGGCGGAGGGACCA AGGTGGAG3' (SEQ ID NO 61), where N is A, C, G or T and K is G or T; for encoding a 6 amino acid sequence, the KV6R primer had the formula 5' GATTTTGCAGTGTAT-TACTGTCAGCAGTATNNKNNKNNKNN-KNNKNNKACTT TCGGCGGAGGGACCAAGGTG-GAG3' (SEQ ID NO 63),where N is A, C, G or T and K is G or T; and for encoding a 10 amino acid sequence, the KV10OR primer had the formula 5' GATTTTGCAGTG-TATTACTGTNNKNNKNNKNNKNNKNN-KNNKNNKNNKNNKT TCGGCGGAGGGACCAAG-GTGGAG3' (SEQ ID NO 64), where N is A, C, G or T and K is G or T.

The CDR3 light chain synthetic binding sites produced in the various PCR reactions are then introduced into libraries for screening. They can be used independently or in concert with similar binding site sequences created in the heavy chain CDR3 domain. The use of the two synthetic binding site protein-encoding sequences enhances the ability of obtaining synthetic binding site proteins displayed on human Fabs that exhibit unexpected affinities and avidities to preselected target molecules. Thus, the synthetic binding site compositions in the heavy and light chain CDR3 domains of this invention allow for the production of reactive binding molecules not normally attainable that have therapeutic and diagnostic uses.

7. Deposit of Materials

The following cell lines and plasmids have been deposited on Feb. 2, 1993, with the American Type Culture Collection, 10801 University Blvd., Manassas, Va., USA (ATCC):

| Material | ATCC Accession No. |
| --- | --- |
| E. coli harboring plasmid pMT12 | ATCC 69079 |
| Plasmid pC3AP313 | ATCC 75408 |
| Plasmid p7EIII | ATCC 75409 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The deposits will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain or plasmid is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines and plasmids deposited, since the deposited embodiment is intended as a single illustration of one aspect of the invention and any cell lines or plasmid vectors that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. A method for producing a polypeptide having a binding site that binds a preselected antigen, the method comprising the steps of:
   i) amplifying a complementarity determining region (CDR) encoding portion of a template immunoglobulin variable domain gene selected from the group consisting of a template immunoglobulin heavy chain variable domain gene and a template immunoglobulin light chain variable domain gene, wherein said template immunoglobulin heavy or light chain genes each have a framework encoding region and said CDR encoding portion and encode respective heavy and light chain variable domain polypeptides having a preselected antigen binding specificity to a first antigen, and wherein said amplifying is by a primer extension reaction using a primer extension reaction oligonucleotide or its complement, for mutagenizing a preselected nucleotide in said CDR encoding portion, thereby forming a library of amplified CDR-mutagenized encoding immunoglobulin gene fragments, said primer extension reaction oligonucleotide having a 3' and 5' termini and comprising:
   a) a nucleotide sequence at the 3' terminus that hybridizes to a first framework encoding region of said selected template immunoglobulin variable domain gene, said first framework encoding region being located adjacent and 5' to said CDR encoding portion;
   b) a nucleotide sequence at the 5' terminus that hybridizes to a second framework encoding region of said selected template immunoglobulin variable domain gene, said second framework encoding region being located adjacent and 3' to said CDR encoding portion; and
   c) a nucleotide sequence between said 5' and 3' termini according to the formula:

—X—[MNN]$_a$—Y—[MNN]$_b$—X—, where the sum of a and b is from 5 to 50, X is a trinucleotide encoding cysteine or a native amino acid residue coded by the immunoglobulin gene, N is independently any nucleotide, M is adenine (A) or cytosine (C), Y is a nucleotide sequence that encodes a preselected polypeptide sequence of from 3 to 50 amino acid residues, Y includes the tripeptide RGD, and said 5' and 3' terminal nucleotide sequences have a length of about 6 to 50 nucleotides in length;

ii) inserting individual members of the library of amplified CDR encoding portions formed in step (i) into a dicistronic phagemid expression vector comprising immunoglobulin heavy and light chain variable domain genes that lack the immunoglobulin gene portion corresponding to the fragment to be inserted, wherein upon insertion said vector is capable of expressing heavy and light chain variable domain polypeptides encoded by said vector, thereby forming a library of dicistronic expression vectors containing amplified CDR-mutagenized immunoglobulin gene fragments;

iii) expressing said immunoglobulin heavy and light chain genes in the library of dicistronic expression vectors formed in step (ii) in a host cell whereby said encoded heavy and light chain variable domain polypeptides assemble on the surface of a phage to form a phage-displayed immunoglobulin heterodimer, thereby producing a library of CDR-mutagenized phage-displayed immunoglobulin heterodimers; and iv) immunoreacting members of the library of CDR-mutagenized phage-displayed immunoglobulin heterodimers formed in step (iii) on a preselected second antigen, said second antigen being different than said first antigen, to allow for selection of a CDR-mutagenized phage-displayed immunoglobulin heterodimer containing a polypeptide having a binding site capable of binding said preselected second antigen; wherein said binding site is an RGD-dependent binding site and wherein said oligonucleotide has the formula:
5' CTCCTCCTCCTCCTCGACGTCCATATAATAATT[MNN]$_a$ATCGCCACG[MNN]$_b$TGGCCCCAC TCTCGCACAATAATA3' (SEQ ID NO 49).

2. A method for producing a polypeptide having a binding site that binds a preselected antigen, the method comprising the steps of:

i) amplifying a complementarity determining region (CDR) encoding portion of a template immunoglobulin variable domain gene selected from the group consisting of a template immunoglobulin heavy chain variable domain gene and a template immunoglobulin light chain variable domain gene, wherein said template immunoglobulin heavy or light chain genes each have a framework encoding region and said CDR encoding portion and encode respective heavy and light chain variable domain polypeptides having a preselected antigen binding specificity to a first antigen, and wherein said amplifying is by a primer extension reaction using a primer extension reaction oligonucleotide or its complement, for mutagenizing a preselected nucleotide in said CDR encoding portion, thereby forming a library of amplified CDR-mutagenized encoding immunoglobulin gene fragments, said primer extension reaction oligonucleotide having a 3' and 5' termini and comprising:

a) a nucleotide sequence at the 3' terminus that hybridizes to a first framework encoding region of said selected template immunoglobulin variable domain gene, said first framework encoding region being located adjacent and 5' to said CDR encoding portion;

b) a nucleotide sequence at the 5' terminus that hybridizes to a second framework encoding region of said selected template immunoglobulin variable domain gene, said second framework encoding region being located adjacent and 3' to said CDR encoding portion; and c) a nucleotide sequence between said 5' and 3' termini according to the formula:

—X—[MNN]$_a$—Y—[MNN]$_b$—X—, where the sum of a and b is from 5 to 50, X is a trinucleotide encoding cysteine or a native amino acid residue coded by the immunoglobulin gene, N is independently any nucleotide, M is adenine (A) or cytosine (C), Y is a nucleotide sequence that encodes a preselected polypeptide sequence of from 3 to 50 amino acid residues, Y includes the tripeptide RGD, and said 5' and 3' terminal nucleotide sequences have a length of about 6 to 50 nucleotides in length;

ii) inserting individual members of the library of amplified CDR encoding portions formed in step (i) into a dicistronic phagemid expression vector comprising immunoglobulin heavy and light chain variable domain genes that lack the immunoglobulin gene portion corresponding to the fragment to be inserted, wherein upon insertion said vector is capable of expressing heavy and light chain variable domain polypeptides encoded by said vector, thereby forming a library of dicistronic expression vectors containing amplified CDR-mutagenized immunoglobulin gene fragments;

iii) expressing said immunoglobulin heavy and light chain genes in the library of dicistronic expression vectors formed in step (ii) in a host cell whereby said encoded heavy and light chain variable domain polypeptides assemble on the surface of a phage to form a phage-displayed immunoglobulin heterodimer, thereby producing a library of CDR-mutagenized phage-displayed immunoglobulin heterodimers; and iv) immunoreacting members of the library of CDR-mutagenized phage-displayed immunoglobulin heterodimers formed in step (iii) on a preselected second antigen, said second antigen being different than said first antigen, to allow for selection of a CDR-mutagenized phage-displayed immunoglobulin heterodimer containing a polypeptide having a binding site capable of binding said preselected second antigen; wherein said binding site is an RGD-dependent binding site; and wherein said oligonucleotide has the formula:
5' CTCCTCCTCCTCCTCGACGTCCATATAATAGCA[MNN]$_a$ATCGCCACG[MNN]$_b$GCACCCCAC TCTCGCACAATAATA3' (SEQ ID NO 50).

3. A method for producing a polypeptide having a binding site that binds a preselected antigen, the method comprising the steps of:

i) amplifying a complementarity determining region (CDR) encoding portion of a template immunoglobulin variable domain gene selected from the group consisting of a template immunoglobulin heavy chain variable domain gene and a template immunoglobulin light chain variable domain gene, wherein said template immunoglobulin heavy or light chain genes each have a framework encoding region and said CDR encoding portion and encode respective heavy and light chain variable domain polypeptides having a preselected antigen binding specificity to a first antigen, and wherein said amplifying is by a primer extension reaction using a primer extension reaction oligonucleotide, or its complement, for mutagenizing a preselected nucleotide in said CDR encoding portion, thereby forming a library of amplified CDR-mutagenized encoding immunoglobulin gene fragments, said primer extension reaction oligonucleotide having a 3', and 5' termini and comprising:

a) a nucleotide sequence at the 3' terminus that hybridizes to a first framework region of said selected template immunoglobulin variable domain gene, said first framework region being located adjacent and 5' to said CDR encoding portion;

b) a nucleotide sequence at the 5' terminus that hybridizes to a second framework encoding region of said selected template immunoglobulin variable domain gene, said second framework encoding region being located adjacent and 3' to said CDR encoding portion; and c) nucleotide sequence between said 5' and 3' termini according to the formula:

-L-[MNN]$_4$—P— where L and P are each one to ten trinucleotides encoding preselected CDR sequences, N is independently any nucleotide, M is adenine (A) or cytosine (C) or analogs thereof;

ii) inserting individual members of the library of amplified CDR encoding portions formed in step (i) into a dicistronic phagemid expression vector comprising immunoglobulin heavy and light chain variable domain genes that lack the immunoglobulin gene portion corresponding to the fragment to be inserted, wherein upon insertion said vector is capable of expressing heavy and light chain variable domain polypeptides encoded by said vector, thereby forming a library of dicistronic expression vectors containing amplified CDR-mutagenized immunoglobulin gene fragments;

iii) expressing said immunoglobulin heavy and light chain genes in the library of dicistronic expression vectors formed in step (ii) in a host cell whereby said encoded heavy and light chain variable domain polypeptides assemble on the surface of a phage to form a phage-displayed immunoglobulin heterodimer, thereby producing a library of CDR-mutagenized phage-displayed immunoglobulin heterodimers; and iv) immunoreacting members of the library of CDR-mutagenized phage-displayed immunoglobulin heterodimers formed in step (iii) on a preselected second antigen, said second antigen being different than said first antigen, to allow for selection of a CDR-mutagenized phage-displayed immunoglobulin heterodimer containing a polypeptide having a binding site capable of binding said preselected second antigen; wherein said oligonucleotide has the formula:

5' CTCCTCCTCCTCCTCGACGTCCATATAATAGCAAT TCCT[MNN]$_4$ CCCAAACGAGCACCCCAC TCTCGCA-CAATAATA3' (SEQ ID NO 52).

* * * * *